(12) United States Patent
Boucher et al.

(10) Patent No.: US 7,721,740 B2
(45) Date of Patent: May 25, 2010

(54) DEVICES, SYSTEMS, AND METHODS USING MAGNETIC FORCE SYSTEMS IN OR ON TISSUE

(75) Inventors: Ryan P. Boucher, San Francisco, CA (US); Edward M. Gillis, San Jose, CA (US); Joe Paraschac, San Jose, CA (US); Scott A. McGill, San Ramon, CA (US); Charles R. Rampersaud, San Francisco, CA (US); Craig A. Purdy, Sunnyvale, CA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 1050 days.

(21) Appl. No.: 11/397,744

(22) Filed: Apr. 4, 2006

(65) Prior Publication Data
US 2007/0000497 A1   Jan. 4, 2007

Related U.S. Application Data

(63) Continuation-in-part of application No. 10/806,372, filed on Mar. 22, 2004, now Pat. No. 7,441,559, which is a continuation-in-part of application No. 10/718,254, filed on Nov. 20, 2003, now Pat. No. 7,360,542, which is a continuation-in-part of application No. 10/656,861, filed on Sep. 6, 2003, now Pat. No. 7,188,627, which is a continuation-in-part of application No. 10/236,455, filed on Sep. 6, 2002.

(60) Provisional application No. 60/441,639, filed on Jan. 22, 2003, provisional application No. 60/456,164, filed on Mar. 20, 2003, provisional application No. 60/739,519, filed on Nov. 23, 2005, provisional application No. 60/754,839, filed on Dec. 29, 2005.

(51) Int. Cl.
*A61F 5/56* (2006.01)

(52) U.S. Cl. .................. 128/848; 602/902; 128/859
(58) Field of Classification Search ................ 128/848, 128/859, 860–861; 602/902; 433/6
See application file for complete search history.

(56) References Cited

U.S. PATENT DOCUMENTS

| | | | |
|---|---|---|---|
| 4,304,227 A | 12/1981 | Samelson | |
| 4,978,323 A | 12/1990 | Freedman | |
| 5,019,372 A | 5/1991 | Folkman et al. | |
| 5,176,618 A | 1/1993 | Freedman | |
| 5,220,918 A | 6/1993 | Heide et al. | |
| 5,373,859 A | 12/1994 | Forney | |
| 5,465,734 A | 11/1995 | Alvarez et al. | |
| 5,649,540 A | 7/1997 | Alvarez et al. | |
| 5,792,067 A | 8/1998 | Karell | |
| RE36,120 E | 3/1999 | Karell | |

(Continued)

FOREIGN PATENT DOCUMENTS

DE    4307262    3/1993

*Primary Examiner*—Michael A. Brown

(57) ABSTRACT

Systems and methods include magnetic structures for placement in or on tissues in an airway. The magnetic structures carry sources of magnetism, which generate magnetic fields having directions. The magnetic fields interact to provide magnetic forces that provide a desired therapeutic effect, e.g., maintaining separation between the soft palate and/or tongue and the posterior pharyngeal wall. The systems and methods size and configure the directions of the magnetic fields to provide stability, which makes possible the achievement of the desired therapeutic effect in a straightforward and elegant manner.

29 Claims, 33 Drawing Sheets

U.S. PATENT DOCUMENTS

| | | | |
|---|---|---|---|
| 5,884,628 A * | 3/1999 | Hilsen | 128/848 |
| 5,979,456 A | 11/1999 | Magovern | |
| 5,988,171 A | 11/1999 | Sohn et al. | |
| 6,231,496 B1 | 5/2001 | Wilk et al. | |
| 6,244,865 B1 | 6/2001 | Nelson et al. | |
| 6,250,307 B1 | 6/2001 | Conrad et al. | |
| 6,390,096 B1 | 5/2002 | Conrad et al. | |
| 6,401,717 B1 | 6/2002 | Conrad et al. | |
| 6,408,851 B1 | 6/2002 | Karell | |
| 6,415,796 B1 | 7/2002 | Conrad et al. | |
| 6,450,169 B1 | 9/2002 | Conrad et al. | |
| 6,490,885 B1 | 12/2002 | Wilkinson | |
| 6,523,541 B2 | 2/2003 | Knudson et al. | |
| 6,523,542 B2 | 2/2003 | Knudson et al. | |
| 6,636,767 B1 | 10/2003 | Knudson et al. | |
| 6,742,524 B2 | 6/2004 | Knudson et al. | |
| 6,955,172 B2 | 10/2005 | Nelson et al. | |
| 7,073,505 B2 | 7/2006 | Nelson et al. | |
| 7,077,143 B2 | 7/2006 | Knudson et al. | |
| 7,077,144 B2 | 7/2006 | Knudson et al. | |
| 7,188,627 B2 | 3/2007 | Nelson et al. | |
| 2001/0047805 A1 | 12/2001 | Scarberry et al. | |
| 2002/0066702 A1 | 6/2002 | Liu | |
| 2004/0112390 A1 * | 6/2004 | Brooks et al. | 128/863 |
| 2005/0092332 A1 | 5/2005 | Conrad et al. | |

* cited by examiner

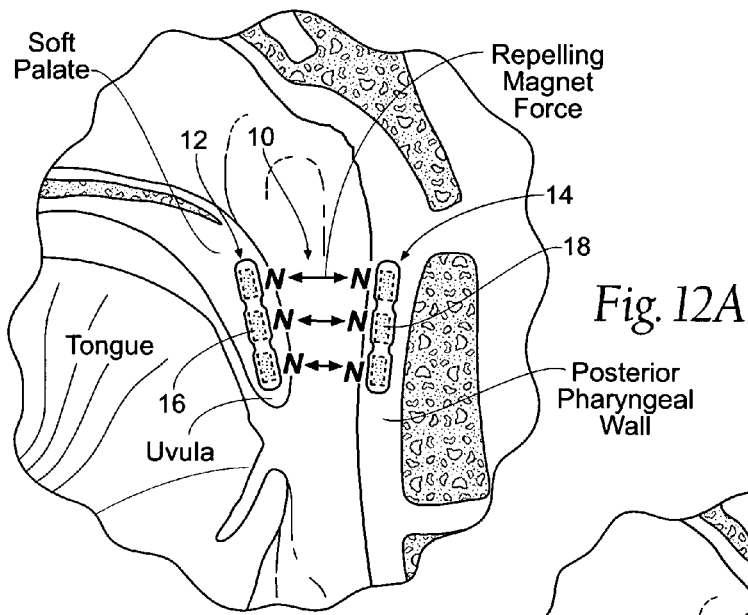
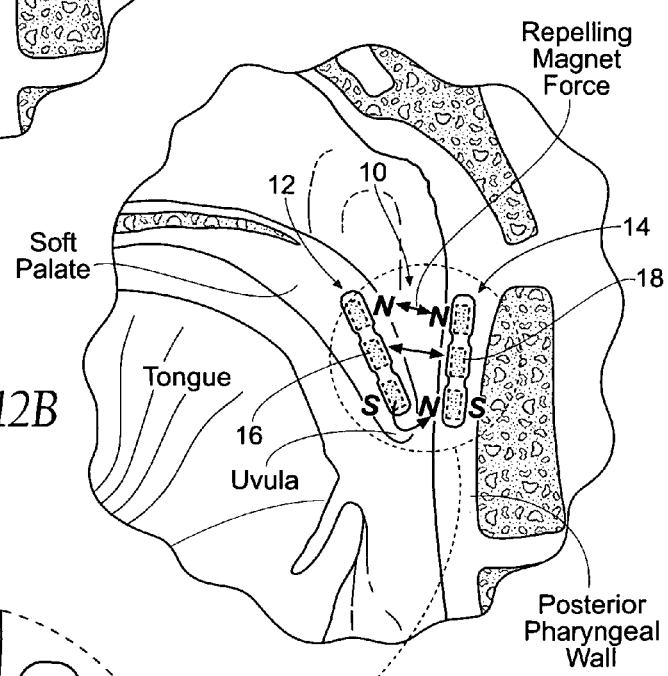
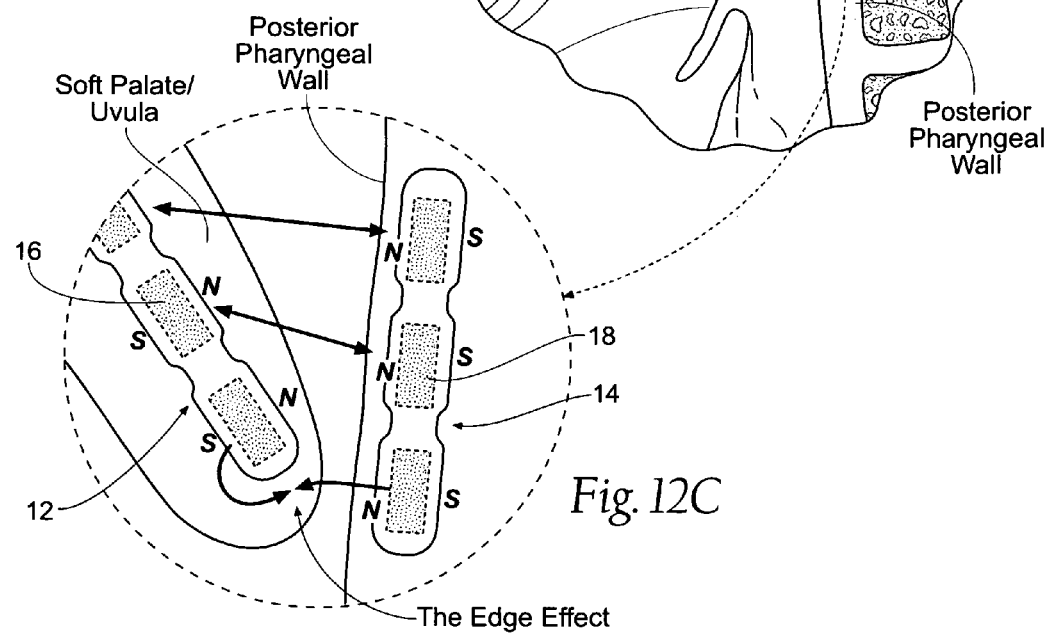

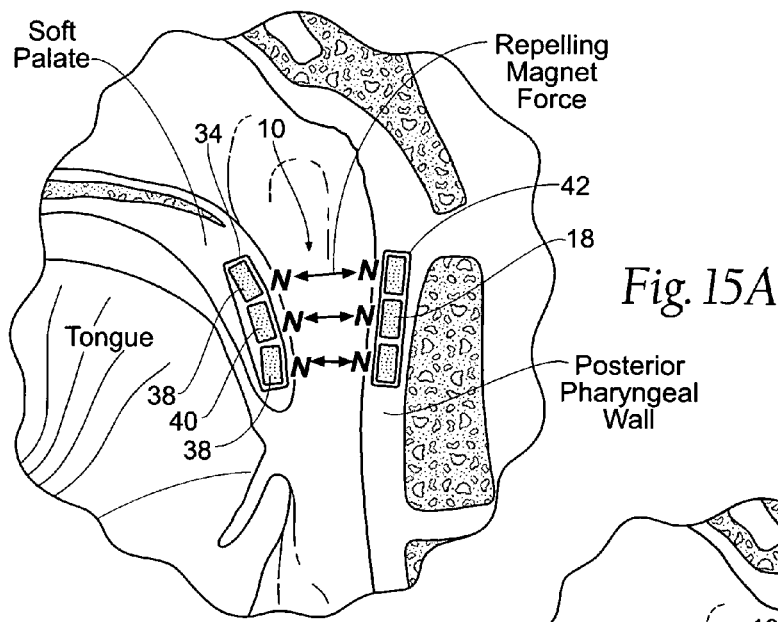
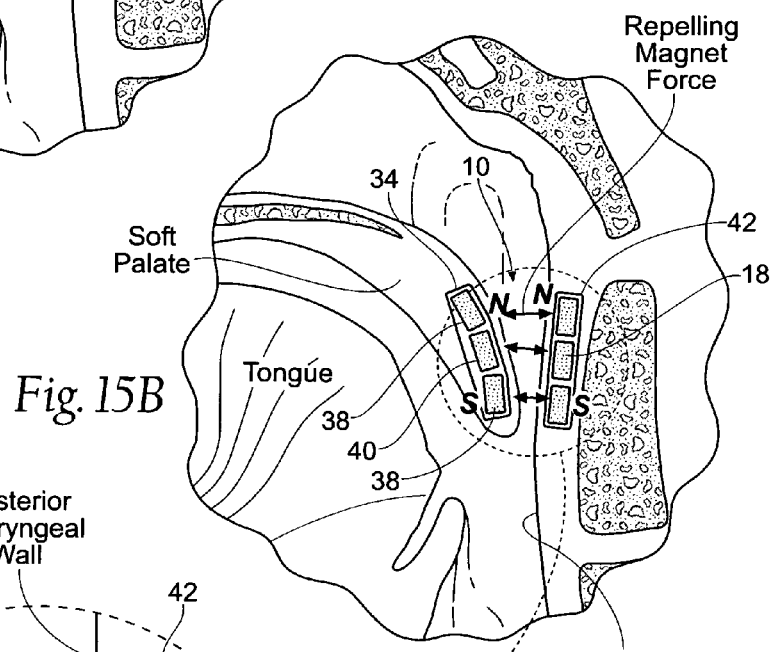
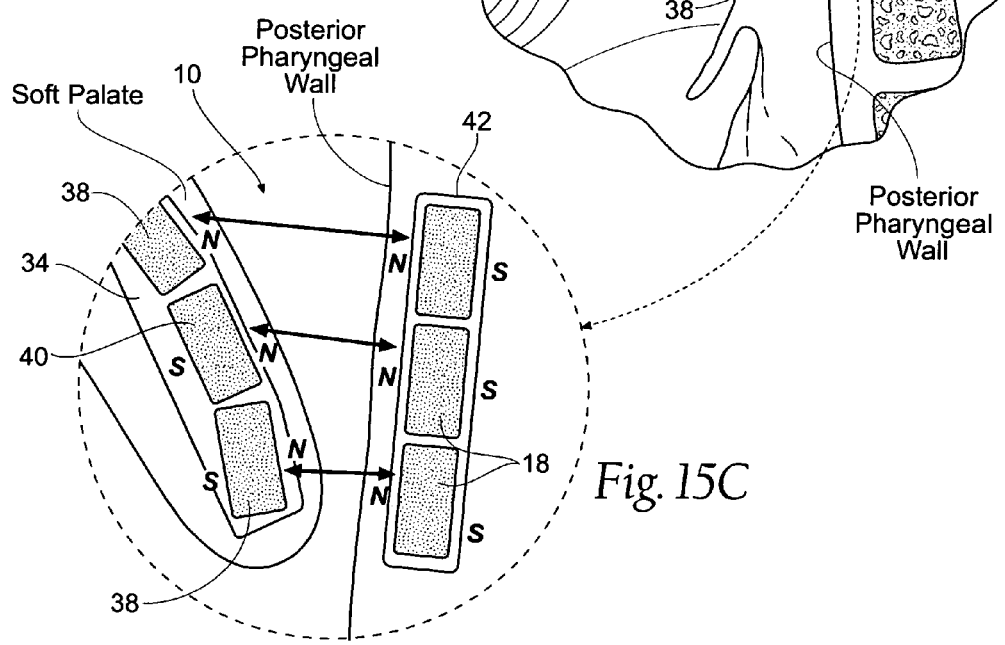
Fig. 15A
Fig. 15B
Fig. 15C

DEVICES, SYSTEMS, AND METHODS USING MAGNETIC FORCE SYSTEMS IN OR ON TISSUE

RELATED APPLICATIONS

This application is a continuation-in-part of U.S. patent application Ser. No. 10/806,372, filed Mar. 22, 2004 now U.S. Pat. No. 7,441,559 entitled "Devices, Systems, and Methods to Fixate Tissue Within the Regions of the Body, Such as the Pharyngeal Conduit," which is a continuation-in-part of U.S. patent application Ser. No. 10/718,254, filed Nov. 20, 2003 now U.S. Pat. No. 7,360,542 entitled "Devices, Systems, and Methods to Fixate Tissue Within the Regions of the Body, Such as the Pharyngeal Conduit," which is a continuation-in-part of U.S. patent application Ser. No. 10/656,861, filed Sep. 6, 2003 now U.S. Pat. No. 7,188,627 entitled "Magnetic Force Devices, Systems, and Methods for Resisting Tissue Collapse within the Pharyngeal Conduit, which further claims the benefit of U.S. Provisional Patent Application Ser. No. 60/441,639, filed Jan. 22, 2003 and U.S. Provisional Patent Application Ser. No. 60/456,164, filed Mar. 20, 2003, and which is a continuation-in-part of co-pending U.S. patent application Ser. No. 10/236,455, filed Sep. 6, 2002 and entitled "System and Method for Moving and/or Restraining Tissue in the Upper Respiratory System." This application also claims the benefit of U.S. Provisional Patent Application Ser. No. 60/739,519, filed Nov. 23, 2005 and U.S. Provisional Patent Application Ser. No. 60/754,839, filed Dec. 29, 2005.

FIELD OF THE INVENTION

The invention is directed to devices, systems, and methods for the treatment of sleep disordered breathing including snoring and obstructive sleep apnea.

BACKGROUND OF THE INVENTION

I. Characteristics of Sleep Apnea

First described in 1965, sleep apnea is a breathing disorder characterized by brief interruptions (10 seconds or more) of breathing during sleep. Sleep apnea is a common but serious, potentially life-threatening condition, affecting as many as 18 million Americans. Snoring can also occur independent of or during a sleep apneic event.

There are two types of sleep apnea: central and obstructive. Central sleep apnea, which is relatively rare, occurs when the brain fails to send the appropriate signal to the breathing muscles to initiate respirations, e.g., as a result of brain stem injury or damage. Mechanical ventilation is the only treatment available to ensure continued breathing.

Obstructive sleep apnea (OSA) is far more common. Normally, the muscles of the upper part of the throat keep the airway open to permit air flow into the lungs. When the muscles of the soft palate and the uvula (the small fleshy tissue hanging from the center of the back of the throat) relax and sag, the relaxed tissues may vibrate as air flows past the tissues during breathing, resulting in snoring. Snoring affects about half of men and 25 percent of women—most of whom are age 50 or older.

In more serious cases, the airway becomes blocked, making breathing labored and noisy, or even stopping it altogether. In a given night, the number of involuntary breathing pauses or "apneic events" may be as high as 20 to 30 or more per hour. These breathing pauses are almost always accompanied by snoring between apnea episodes, although not everyone who snores has the condition. Sleep apnea can also be characterized by choking sensations.

Lack of air intake into the lungs results in lower levels of oxygen and increased levels of carbon dioxide in the blood. The altered levels of oxygen and carbon dioxide alert the brain to resume breathing and cause arousal. The frequent interruptions of deep, restorative sleep often lead to early morning headaches, excessive daytime sleepiness, depression, irritability, and learning and memory difficulties.

The medical community has become aware of the increased incidence of heart attacks, hypertension and strokes in people with moderate or severe obstructive sleep apnea. It is estimated that up to 50 percent of sleep apnea patients have high blood pressure.

Upon an apneic event, the sleeping person is unable to continue normal respiratory function and the level of oxygen saturation in the blood is reduced. The brain will sense the condition and cause the sleeper to struggle and gasp for air. Breathing will then resume, often followed by continued apneic events. There are potentially damaging effects to the heart and blood vessels due to abrupt compensatory swings in blood pressure. Upon each event, the sleeping person will be partially aroused from sleep, resulting in a greatly reduced quality of sleep and associated daytime fatigue.

Although some apneic events are normal in all persons and mammals, the frequency of blockages will determine the seriousness of the disease and opportunity for health damage. When the incidence of blockage is frequent, corrective action should be taken.

II. The Anatomy of the Upper Airway

As FIG. 1 shows, the upper airway consists of a conduit that begins at the nasal valve, situated in the tip of the nose, and extends to the larynx, which is also called the voice box because it houses the vocal cords. The pharynx (which, in Greek, means "throat") is a cone-shaped passageway in the upper airway that leads from the oral and nasal cavities in the head to the esophagus and larynx. The pharynx serves both respiratory and digestive functions. Both circular and longitudinal muscles are present in the walls of this organ, which are called the pharyngeal walls. The circular muscles form constrictions that help push food to the esophagus and prevent air from being swallowed, while the longitudinal muscles lift the walls of the pharynx during swallowing.

The pharynx consists of three main divisions. The anterior portion is the nasal pharynx, the back section of the nasal cavity. The nasal pharynx connects to the second region, the oral pharynx, by means of a passage called an isthmus. The oral pharynx begins at the back of the mouth cavity and continues down the throat to the epiglottis, a flap of tissue that covers the air passage to the lungs and that channels food to the esophagus. The isthmus connecting the oral and nasal regions allows humans to breathe through either the nose or the mouth. The third region is the laryngeal pharynx, which begins at the epiglottis and leads down to the esophagus. Its function is to regulate the passage of air to the lungs and food to the esophagus. Air from the nasal cavity flows into the larynx, and food from the oral cavity is routed to the esophagus directly behind the larynx. The epiglottis, a cartilaginous, leaf-shaped flap, functions as a lid to the larynx and, during the act of swallowing, controls the traffic of air and food.

The mouth cavity marks the start of the digestive tube. Oval in shape, it consists of two parts: the vestibule and the mouth cavity proper.

The vestibule is the smaller outer portion, delimited externally by the lips and cheeks and internally by the gums and teeth. It connects with the body surface through the rima or orifice of the mouth. The vestibule receives the secretion of the parotid salivary glands and connects when the jaws are closed with the mouth cavity proper by an aperture on both sides behind the wisdom teeth, and by narrow clefts between opposing teeth.

The mouth cavity proper contains the tongue and is delimited laterally and in the front by the alveolar arches with the teeth therein contained. It receives the secretion from the submaxillary and sublingual salivary glands. The mouth cavity proper connects with the pharynx by a constricted aperture called isthmus faucium.

The palate forms the arched roof of the oral or mouth cavity (the mouth) and the floor of the nasal cavities (the nose). It separates the oral cavity from the nasal cavities and the nasal pharynx. The palate consists of two regions—the hard palate anteriorly and the soft palate posteriorly.

The hard palate is vaulted and defines the space filled by the tongue when it is at rest. The hard palate has a hard bony skeleton, hence its name.

The soft palate has no bony skeleton, hence its name. The soft palate is suspended from the posterior border of the hard palate. It extends posteriorly and inferiorly as a curved free margin from which hangs a conical process, called the uvula. Muscles arise from the base of the cranium and descend into the soft palate. The muscles allow the soft palate to be elevated during swallowing into contact with the posterior pharyngeal wall. The muscles also allow the soft palate to be drawn inferiorly during swallowing into contact with the posterior part of the tongue.

The soft palate is thereby very dynamic and movable. When a person swallows, the soft palate initially is tensed to allow the tongue to press against it, to squeeze the bolus of food to the back of the mouth. The soft palate is then elevated posteriorly and superiorly against the pharyngeal wall, acting as a valve to prevent passage of food into the nasal cavity.

III. Sleep and the Anatomy of the Upper Airway

Although all tissue along this conduit is dynamic and responsive to the respiratory cycle, only the pharynx is totally collapsible. The pharyngeal structures and individual anatomic components within this region include the pharyngeal walls, the base of the tongue, the soft palate with uvula, and the epiglottis.

The cross sectional area of the upper airway varies with the phases of the respiratory cycle. At the initiation of inspiration (Phase I), the airway begins to dilate and then to remain relatively constant through the remainder of inspiration (Phase II). At the onset of expiration (Phase III) the airway begins to enlarge, reaching maximum diameter and then diminishing in size so that at the end of expiration (Phase IV), it is at its narrowest, corresponding to the time when the upper airway dilator muscles are least active, and positive intraluminal pressure is lowest. The upper airway, therefore, has the greatest potential for collapse and closure at end-expiration. [ref: Schwab R J, Goldberg A N. Upper airway assessment: radiographic and other imaging techniques. Otolaryngol Clin North Am 1998; 31: 931-968]

Sleep is characterized by a reduction in upper airway dilator muscle activity. For the individual who snores or has obstructive sleep apnea (OSA) and perhaps the other disorders which comprise much of the group of entities called obstructive sleep-disordered breathing (SDB), it is believed that this change in muscle function causes pharyngeal narrowing and collapse. Two possible etiologies for this phenomenon in OSA patients have been theorized. One is that these individuals reduce the airway dilator muscle tone more than non-apneics during sleep (the neural theory). The other is that all individuals experience the same reduction in dilator activity in sleep, but that the apneic has a pharynx that is structurally less stable (the anatomic theory). Both theories may in fact be contributors to OSA, but current studies seem to support that OSA patients have an intrinsically structurally narrowed and more collapsible pharynx [ref: Isono S. Remmers J, Tanaka A Sho Y, Sato J, Nishino T. Anatomy of pharynx in patients with obstructive sleep apnea and in normal subjects. J Appl Physiol 1997: 82:1319-1326.] Although this phenomenon is often accentuated at specific sites, such as the velopharyngeal level [Isono], studies of closing pressures [Isono] supports dynamic fast MRI imaging that shows narrowing and collapse usually occurs along the entire length of the pharynx. [ref: Shellock F G, Schatz C J, Julien P, Silverman J M, Steinberg F, Foo T K F, Hopp M L, Westbrook P R. Occlusion and narrowing of the pharyngeal airway in obstructive sleep apnea: evaluation by ultrafast spoiled GRASS MR imaging. Am J of Roentgenology 1992: 158: 1019-1024.].

IV. Treatment Options

To date, the only modality that addresses collapse along the entire upper airway is mechanical positive pressure breathing devices, including continuous positive airway pressure (CPAP) machines. All other modalities, such as various surgical procedures and oral appliances, by their nature, address specific sectors of the airway (such as palate, tongue base and hyoid levels), but leave portions of pharyngeal wall untreated. This may account for the considerably higher success rate of CPAP over surgery and appliances in controlling OSA. Although CPAP, which in essence acts as an airway splint for the respiratory cycle, is highly successful, it has some very significant shortcomings. It can be cumbersome to wear and travel with, difficult to accept on a social level, and not tolerated by many (for reasons such as claustrophobia, facial and nasal mask pressure sores, airway irritation). These factors have lead to a relatively poor long-term compliance rate. One study has shown that 65% of patients abandon their CPAP treatment within 6 months.

Other current treatments for OSA include genioglossal advancement (GA) and maxillomandibular advancement (MA). These are highly invasive surgical procedures with long recovery time, and therefore have relatively low patient appeal.

The need remains for simple, cost-effective devices, systems, and methods for reducing or preventing sleep disordered breathing events and/or snoring.

SUMMARY OF THE INVENTION

The present invention provides systems and methods for the treatment of sleep disordered breathing including obstructive sleep apnea and snoring.

One aspect of the invention provides systems and methods that include magnetic structures for placement in or on tissues in an airway. The magnetic structures carry sources of magnetism, which generate magnetic fields having directions. The magnetic fields interact to provide magnetic forces that provide a desired therapeutic effect, e.g., maintaining separation between the soft palate and/or tongue and the posterior pharyngeal wall. The systems and methods size and configure the directions of the magnetic fields to provide stability, which makes possible the achievement of the desired therapeutic effect in a straightforward and elegant manner.

Other technical features shall be apparent based upon the accompanying description, drawings, and claims.

BRIEF DESCRIPTION OF THE DRAWINGS

FIG. 12A is an anatomic side section view of magnetic implants generally aligned along the airway formed between the soft palate and posterior pharyngeal wall to create a repelling magnetic force field.

FIGS. 12B and 12C are anatomic side section views of the implants shown in FIG. 12A, that show, when the soft palate moves, e.g., during swallowing, the movement can significantly alter the orientation and alignment between the magnetic implants from one moment to another.

FIGS. 15A, 15B, and 15C are anatomic side section views of the implant shown in FIG. 13 implanted in a soft palate in alignment with a magnetic implant in a pharyngeal wall, showing that, as the soft palate moves, e.g., during swallowing, the repelling orientation and alignment between the magnetic implants is maintained.

DESCRIPTION OF THE PREFERRED EMBODIMENTS

This Specification discloses various magnetic implants and devices, systems, and methods to maintain a patent airway. For example, the various aspects of the invention have application in procedures requiring the restriction of tissue collapse in and/or around the body, such as a passageway within the body. The devices, systems, and methods that embody features of the invention are also adaptable for use with devices, systems, and methods that are not restricted to tissue based applications.

The devices, systems, and methods are particularly well suited for treating sleep disordered breathing, including sleep apnea. For this reason, the devices, systems, and methods will be described in this context. Still, it should be appreciated that the disclosed devices, systems, and methods are applicable for use in treating other dysfunctions elsewhere in the body, which are not necessarily sleep disorder related.

I. The Palate

A. Anatomy

Figure 1:
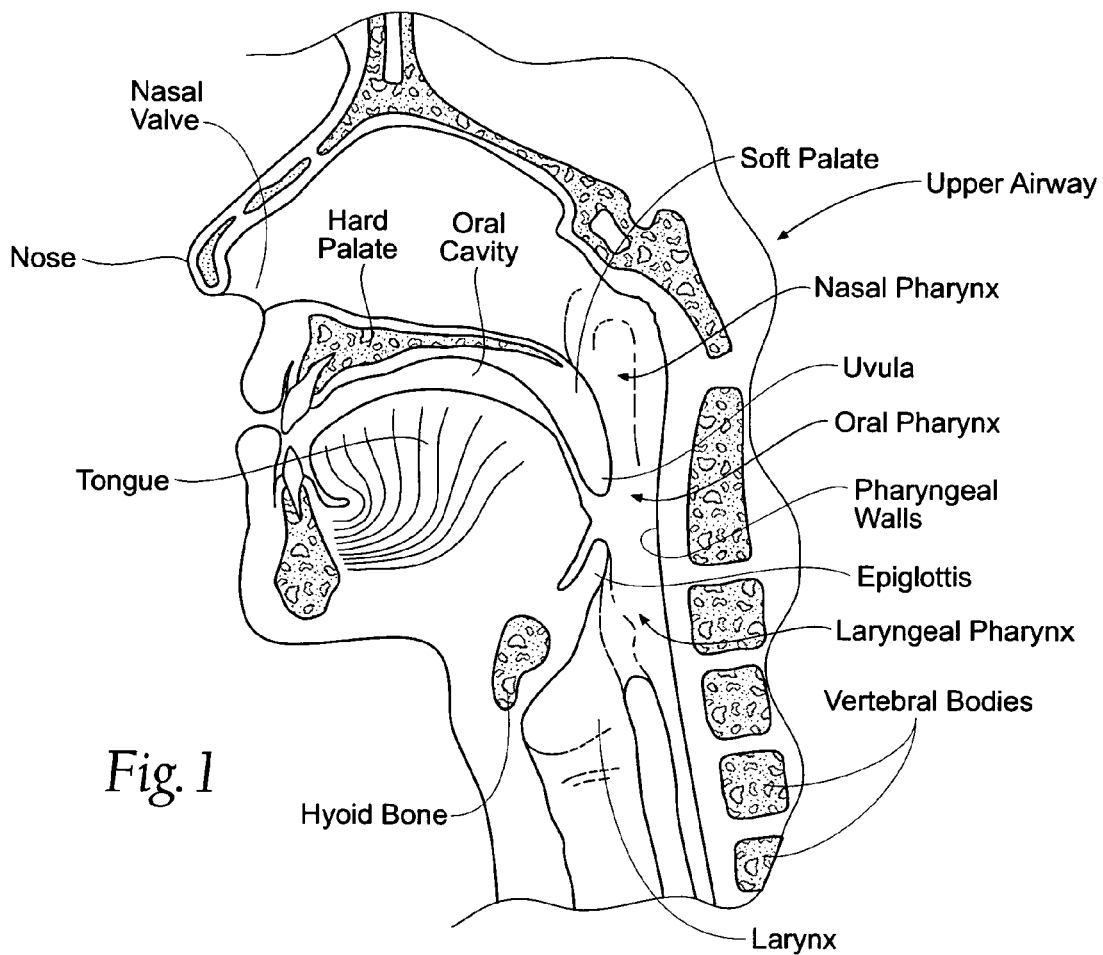
FIG. 1 is an anatomic side section view of the upper airway of a human, showing the nasal and oral cavities, tongue, hard palate, soft palate, oral pharynx, chin and neck.
Figure 2:
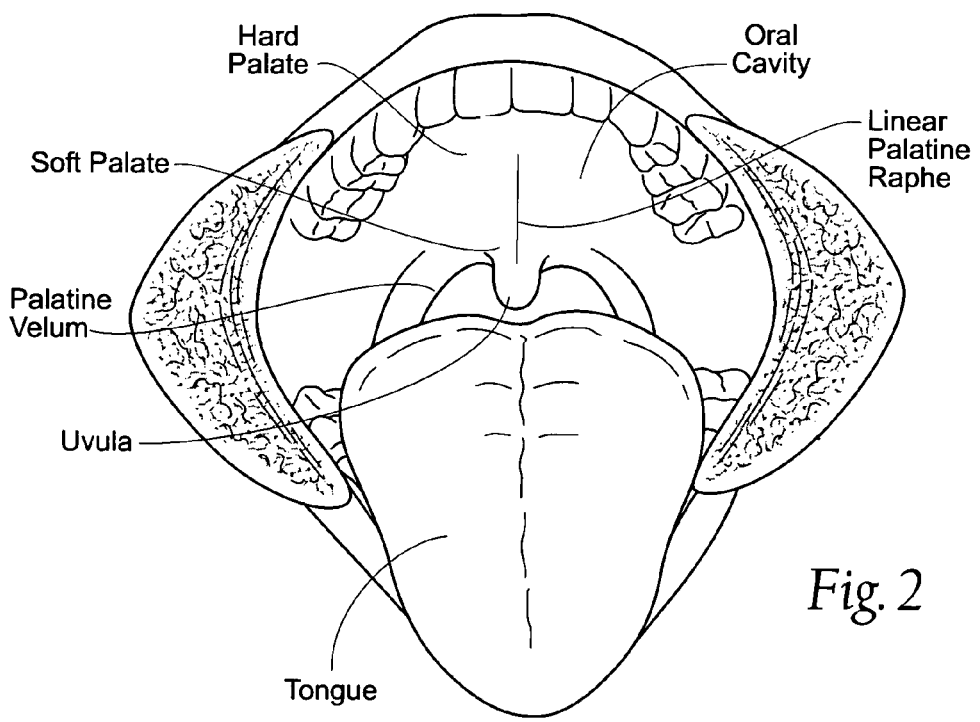
FIG. 2 is an anatomical anterior view of the oral cavity, where the tongue has been pulled towards the front to show the roof of the mouth comprising the hard palate (in the front) and the soft palate (in the back).

FIG. 2 shows an anatomical view of the oral cavity, where the tongue has been pulled towards the front. FIG. 2 shows the roof of the mouth, i.e., the palate, as previously described and as also shown in FIG. 1. FIG. 2 shows the two parts of the palate (which have also been previously described: namely, the hard palate (in the front) and the soft palate (in the back).

The hard palate is bounded in the front and laterally by the alveolar arches and gums and in the back by the soft palate. A dense structure made up by the periosteum and the mucous membrane of the mouth covers the hard palate. The linear raphé lies along the middle line of the hard palate.

The soft palate is a movable fold, suspended from the posterior border of the hard palate and forms an incomplete dividing line (septum) between the mouth and the pharynx. The soft palate comprises a mucous membrane that envelops muscular fibers, an aponeurosis, vessels, nerves, adenoid tissue, and mucous glands.

When the soft palate is relaxed and hanging, the anterior surface is concave and follows the same line as the roof of the mouth. The posterior surface of the soft palate is convex and is a continuance of the mucous membrane that covers the bottom part of the nasal cavities. The upper boundary of the soft palate attaches to the hard palate; the sides become part of the pharynx; and the lower boundary is free. The lower boundary which hangs down, separating the mouth and the pharynx is known as the palatine velum. In the middle of the lower boundary, the small, fleshy cone-shaped protuberance is called the uvula. The arches are located laterally and downwardly from the uvula. These arches are called the glossopalatine arch (the anterior arch) and the pharyngopalatine arch (the posterior arch). The palatine aponeurosis is a thin, firm fiber-filled lamella which gives support to the muscles and makes the soft palate strong.

As previously described, during the process of eating and swallowing, the uvula prevents the food from entering the nasopharynx and the muscles of the soft palate push the food down into the pharynx.

B. The Soft Palate and Sleep Apnea

Sleep apnea takes many forms. Closure of the airway can occur at any number of anatomical structures along the airway, including any combination of the tongue, soft palate, epiglottis, and pharyngeal walls.

Figure 3:
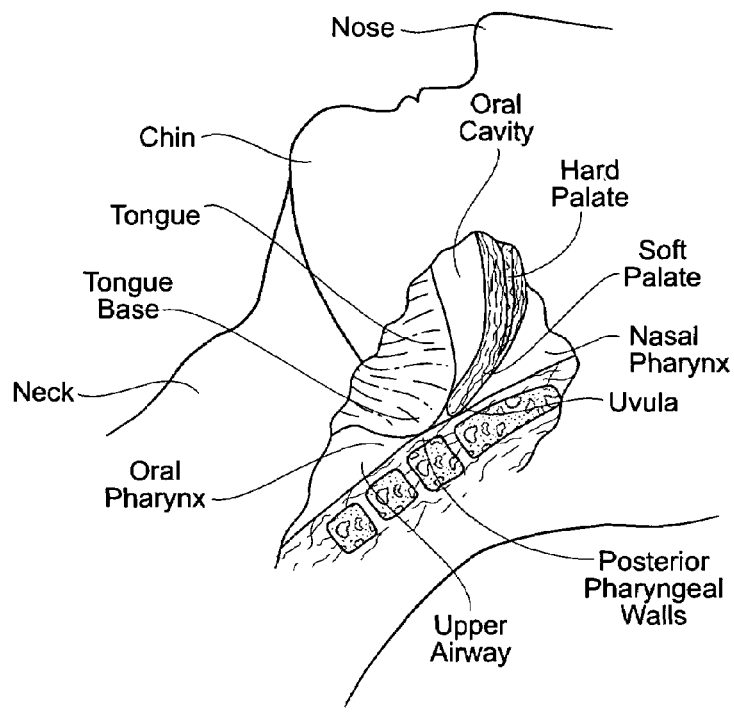
FIG. 3 is an anatomical side view, with sections partly broken away and in section, of a human suffering from one form of sleep apnea involving the soft palate, showing how the tongue base, the soft palate, and the uvula lean against the pharyngeal wall, effectively closing off the airway, resulting in an apneic event.

FIG. 1 is an anatomical side view of the upper airway system in a normal patient, showing the nasal and oral cavities, tongue, hard palate, soft palate, oral pharynx, chin and neck. FIG. 3 shows an anatomical side view of a patient suffering from one form of sleep apnea involving the soft palate. As shown in FIG. 3, the tongue base, the soft palate, and the uvula lean against the pharyngeal wall, effectively closing off the airway. An apneic event can occur as a result.

II. Magnetic Force Systems

A. Overview

Figure 4:
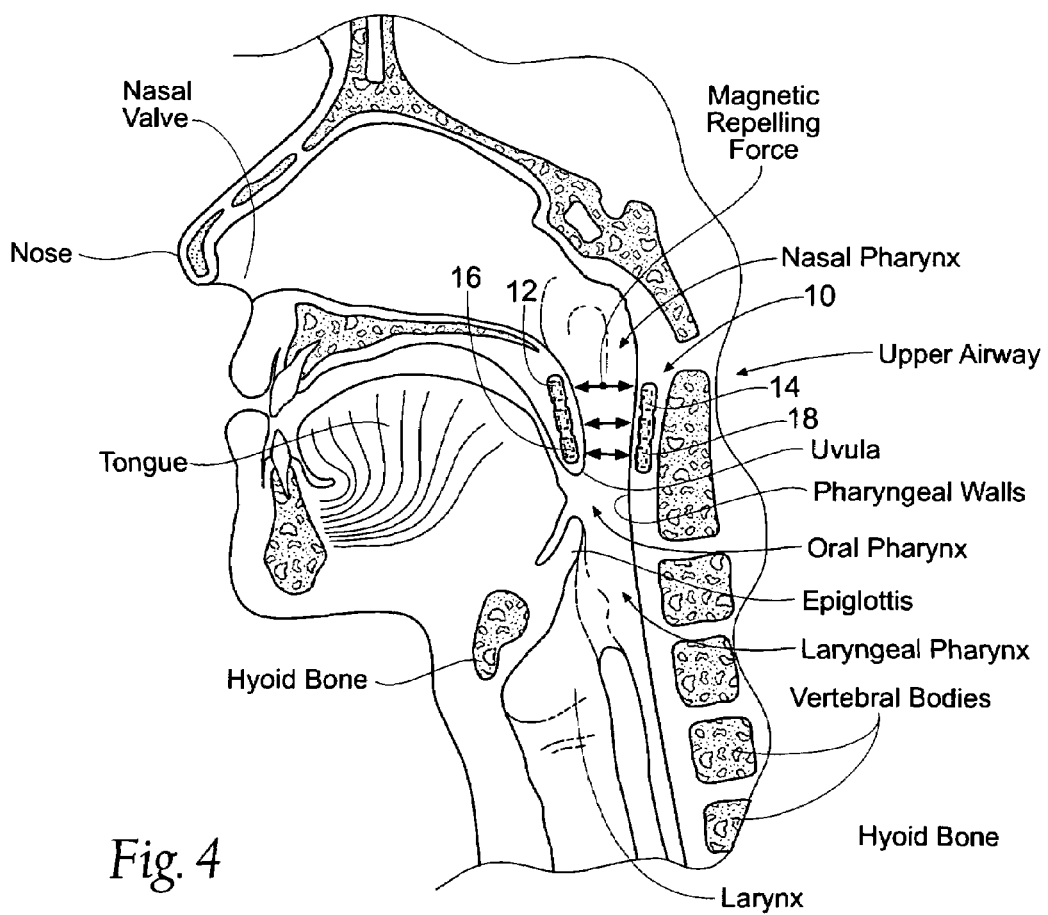
FIG. 4 shows in a diagrammatic way a magnetic force system that resists occurrence of the tissue condition shown in FIG. 3, involving the collapse of the soft palate and uvula against the pharyngeal wall.

FIG. 4 shows in a diagrammatic way a magnetic force system 10 that resists occurrence of the tissue condition shown in FIG. 3, involving the collapse of the soft palate and uvula against the pharyngeal wall. The magnetic force system 10 creates a magnetic force field in that location of the airway, which maintains the soft palate and uvula in a position spaced away from the posterior pharyngeal wall, as FIG. 4 shows. The magnetic force field resists posterior movement of the soft palate and uvula during sleep, keeping the airway between the soft palate and uvula open. An apneic episode is avoided.

The magnetic force system 10 can be variously constructed. In FIG. 4, the force system 10 includes two components 12 and 14. The first component 12 comprises one or more magnetic structures placed in or on tissue in the soft palate or uvula. The second component 14 comprises one or more magnetic structures placed in or on the posterior pharyngeal wall generally aligned with the soft palate. The magnetic structures or magnetic components 12 and 14 interact by developing a magnetic force between them, i.e., across the airway, which is indicated by arrows in FIG. 4. The magnetic force can comprise a repelling force (i.e., a force in essentially an anterior-posterior direction between the soft palate and posterior pharyngeal wall), and/or a torquing force (i.e., a force or moment of a force that tends to rotate the soft palate about an axis), and/or a decentering force (i.e., a force in essentially a medial or side-to-side direction that tends to offset the soft palate left or right), or a combination of two or more of these forces. The magnetic force between the two magnetic structures or magnetic components 12 and 14 resists the posterior movement of the soft palate or uvula toward the posterior pharyngeal wall, or, stated differently, the magnetic force maintains separation between the soft palate and the posterior pharyngeal wall, thereby preventing the occurrence of the airway-occluding tissue condition shown in FIG. 3. As FIG. 4 shows, the magnetic force between the first and second magnetic structures or magnetic components 12 and 14 keeps the airway open (i.e., patent) during sleep.

B. The Magnetic Structures

In its most basic form, the magnetic structures or magnetic components 12 and 14 of the magnetic force system 10 each comprise at least one magnetic material, respectively 16 and 18. The magnetic materials 16 and 18 are placed in or on the targeted tissue regions in a generally magnetically aligned relationship across the airway between the soft palate and the pharyngeal wall. The magnetic materials 16 and 18 of the magnetic force system 10 are placed to magnetically interact and resist the collapse of tissue in the airway between the soft palate and the pharyngeal wall during sleep.

1. Orientation of Like Poles

Each magnetic material 16 and 18 comprises a "hard" ferromagnetic material, which is also commonly referred to as a permanent magnet. A permanent magnet is characterized as a material showing resistance to external demagnetizing forces once being magnetized. That is, a high external magnetic field is required in order to remove the residual magnetism of a permanent magnet. Stated differently, a permanent magnet has very high intrinsic coercivity, which is a measure of its resistance to demagnetization.

A permanent magnet possesses poles of opposite polarity. The poles are regions of a magnet (usually at the end of the magnets) where the external magnetic field is strongest. Relative to Earth's magnetic poles, if the magnet is free to turn, one pole will point to the magnetic north pole of the Earth, and is thus called a north pole of the magnet, which is indicated by N in the drawings or otherwise called a N-pole. The opposite pole is called a south pole of the magnet, which is indicated by S in the drawings or otherwise called a S-pole.

According to physical laws, poles of like polarity (N-N or S-S) repel each other with a magnetic force. Conversely, poles of unlike polarity (N-S or S-N) attract each other with a magnetic force. Thus, structures incorporating permanent magnets will repel each other when like poles of the structures are oriented to face each other, and likewise attract each other when opposite poles of the structures are oriented to face each other. The magnitude of the force of magnetic attraction or repulsion depends on the strength of the magnets and the distance between the poles.

Examples of known permanent magnet materials include alloys of Neodymium-Iron-Boron (NdFeB), alloys of Aluminum-Nickel-Cobalt (AlNiCo), and Samarium Cobalt (SmCo). An electromagnet (current flowing through a coil of wire) can be substituted for a permanent magnet.

In the magnetic force system 10 shown in FIG. 4, the magnetic materials 16 and 18 are oriented such that like poles generally face each other across the airway (N-N or S-S). Thus, the first and second magnetic structures or magnetic components 12 and 14 are referred to as having the same polarity. The magnetic structures or magnetic components 12 and 14 will magnetically interact by the generation of a magnetic force between them. The nature of the magnetic force will generally be called in shorthand for purposes of description a "repelling" magnetic force, because of the interaction of magnetic poles of the same polarity. However, it should be appreciated that the magnetic force can include a torquing force (i.e., a force or moment of a force that tends to rotate the soft palate about an axis), and/or a decentering force (i.e., a force in essentially a medial or side-to-side direction that tends to offset the soft palate left or right), or a combination of two or more repelling, torquing, and decentralizing forces. One or more of these magnetic forces collectively prevent the soft palate from moving in a posterior direction and closing or restricting the pharyngeal conduit or airway.

2. Configuration of the Magnetic Structures

As described, the magnetic materials 16 and 18 are placed in or on tissue. The term placed "in or on" is intended to mean that the magnetic materials 16 and 18 can be placed either on surface tissue or implanted within tissue. For longevity and comfort, the materials 16 and 18 are desirably implanted within tissue. In the illustrated embodiment, the magnetic material 16 is implanted within a region of the soft palate or uvula. The magnetic material 18 is implanted in a posterior region of the pharyngeal wall.

Figure 5:
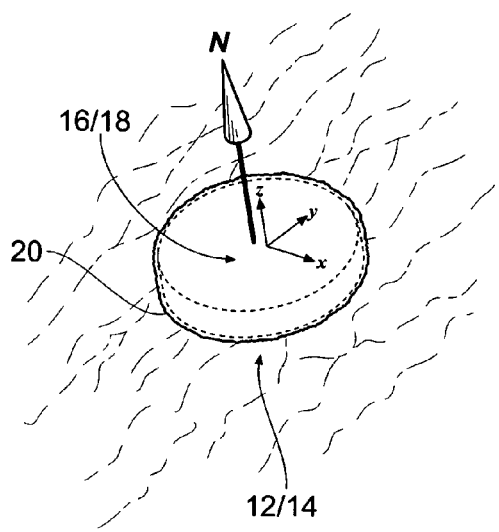
FIG. 5 is a perspective view of a permanent magnetic material sized and configured for implantation as part of the system shown in FIG. 4.

The implanted permanent magnetic materials 16 and 18 can each be configured in various ways and take various shapes, e.g., cylindrical, square, rectangular, or other polygons. A given magnetic material 16 or 18 of a given magnetic structure or magnetic component 12 or 14 can comprise a single or discrete source of magnetism having a given desired polar orientation. For example, a given magnetic material 16 or 18 can comprise a single permanent magnet, as shown in FIG. 5. Bonded permanent magnets may also be used. Bonded magnets can be flexible or rigid, and consist of powdered NdFeB, Ferrite or SmCo permanent magnet materials bonded in a flexible or rigid substrate of e.g., silicone, rubber, nitrile, polyethylene, epoxy, polyvinyl chloride, or nylon. The forming of the bonded magnet can be achieved by extrusion, compression molding, injection molding, calendering, or printing. Bonded magnets enable unique flexible designs, and durable high tolerance shapes that are otherwise difficult to achieve. In FIG. 5, the orientation of N-magnetic field is generally normal to the planar surface of the magnetic material 16 or 18, which is generally along the geometric z-axis (the geometric x-axis and y-axis laying within the plane of the magnetic material 16 or 18, as FIG. 5 shows).

Figure 6:
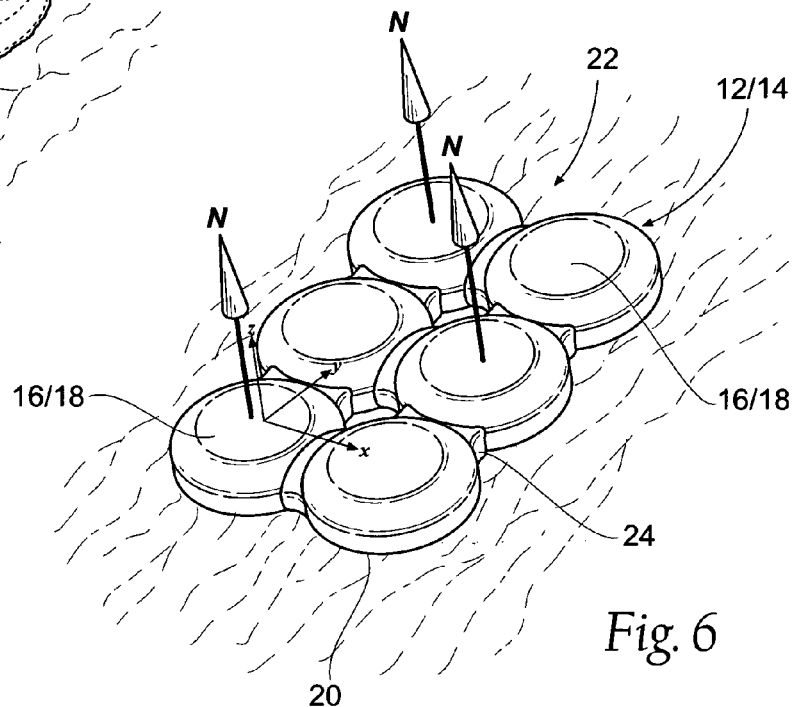
FIG. 6 is a perspective view of an array of permanent magnetic materials in a carrier that is sized and configured for implantation as part of the system shown in FIG. 4.

Alternatively, a plurality of permanent magnetic material 16 or 18 can be positioned for implantation in a flexible or compliant array 22 carried as a unit on a support carrier 24, or otherwise directly linked together, as shown in FIG. 6. The carrier 24 can comprise, for example, a woven, formed, or molded structure made, e.g., from a polymer or fiber or fabric or non-ferrous metallic material. Like the magnetic materials 16/18 themselves, the arrays 22 can be variously shaped, sized, and configured for implantation in the intended tissue region.

In the arrangement shown in FIG. 6, the magnetic materials 16/18 are placed on the carrier 24 with the N and S poles facing generally in the same direction (which, in this embodiment, is generally along the z-axis). In FIG. 6, the N-pole orientation is shown by the arrows, and the S-pole is therefore oriented in an opposite direction. In this way, an array 22 of like permanent magnets 16/18 having the same magnetic orientation (i.e., polarity) can be assembled for implantation as a unit on the carrier 24.

In either arrangement (individually as shown in FIG. 5 or on an array as shown in FIG. 6), the magnetic material 16 or 18 is desirably coated, plated, encapsulated, or deposited prior placement in or on tissue with a selected protective material 20. The protective material 20 is selected to provide a corrosion resistant and biocompatible interface, to prevent interaction between the magnetic material 16/18 and tissues/fluids of the body. The protective material 20 is also desirably selected to form a durable tissue interface, to provide longevity to the system component, and thereby provide resistance to structural fatigue and/or failure. Selected to provide these desired physical and physiologic benefits, the protective material 20 and its application to the material 16/18 is also desirably selected to avoid imparting added stiffness to the magnetic structure or magnetic component 12 or 14 itself.

The protective material 20 can be selected among various types of materials known to provide the desired biocompatibility, resistance to corrosion, and durability. For example, the protective material 20 can comprise titanium material plated, deposited, or otherwise coated upon the magnetic material 16/18. As another example, the protective material 20 can comprise a parylene coating. As other examples, the protective material 20 can comprise a silicone polymer, a non-toxic epoxy, a medical grade polyurethane, or a U.V. curable medical acrylic co-polymer. The protective material 20 may be made up of various layers, each contributing to the protective and/or biocompatibility characteristics of the protective material. The protective material 20 may also incorporate anticoagulants and/or antibiotics and/or tissue in-growth promotion.

C. Representative Systems of Magnetic Structures

Figure 7A:
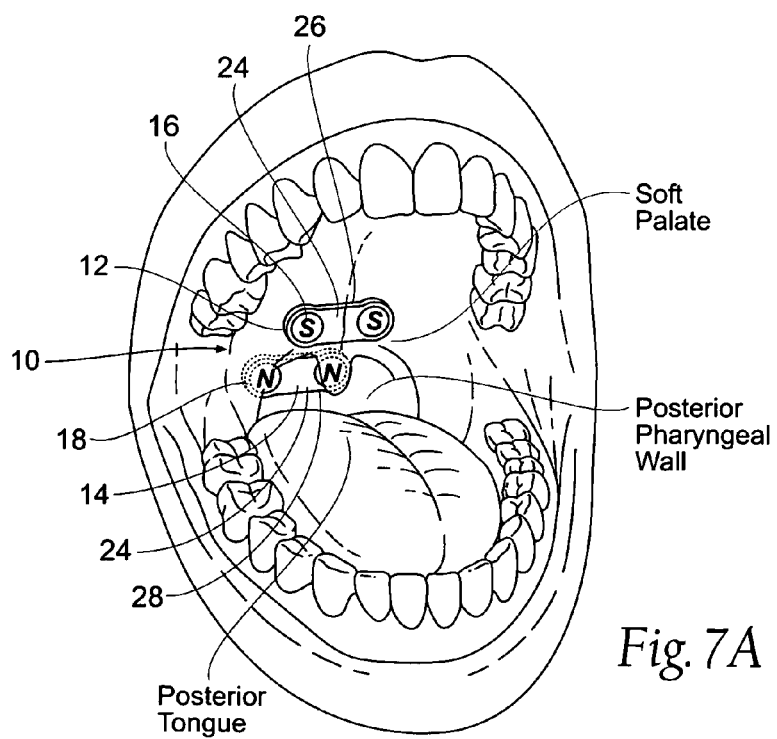
FIGS. 7A and 7B are, respectively, an anatomic anterior view and side section view of a representative magnetic force system of a type shown in FIG. 4, comprising magnetic materials in a soft palate and a pharyngeal wall arranged in a repelling orientation.
Figure 7B:
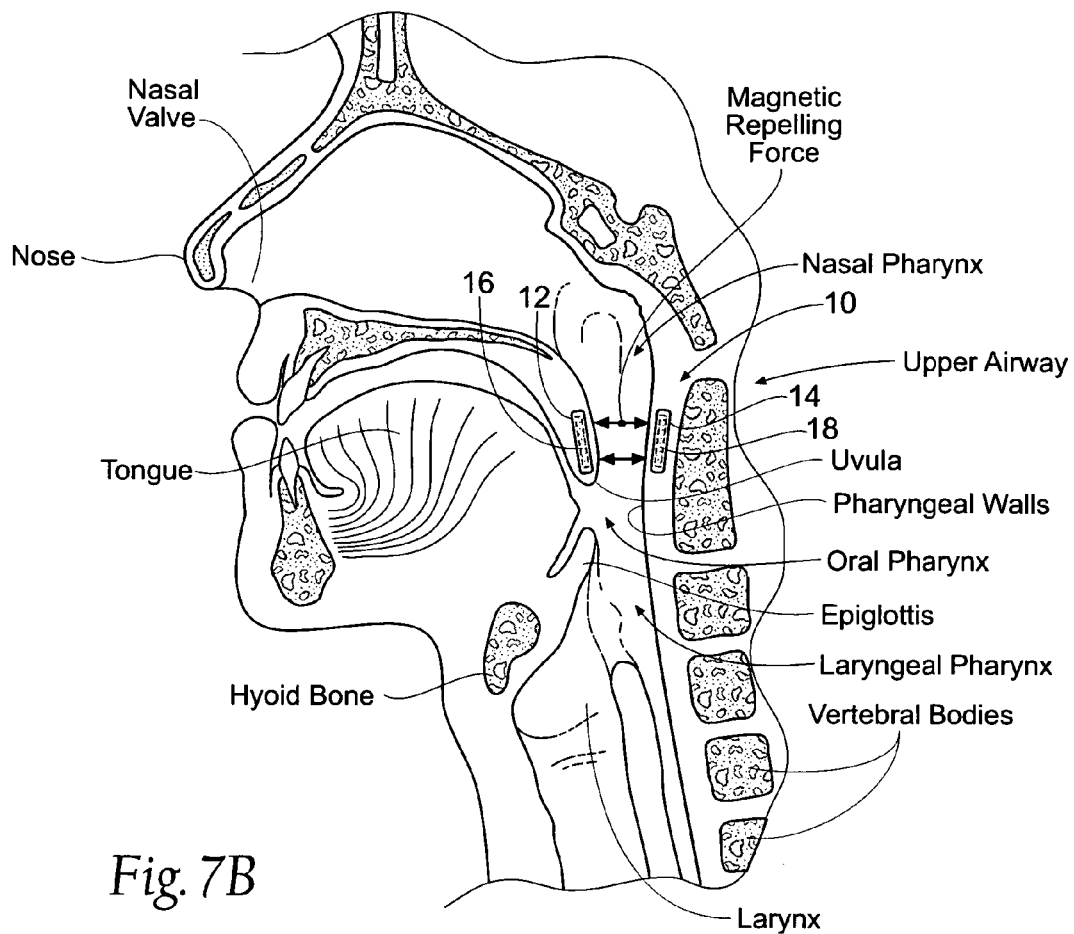

FIGS. 7A and 7B show a representative magnetic force system 10 comprising the magnetic materials 16 and 18 arranged in a repelling orientation, as previously described. In FIGS. 7A and 7B, the magnetic force system 10 includes a first magnetic structure or magnetic component 12 comprising a first magnetic array 26 implanted in the soft palate (or in the uvula). The magnetic force system 10 also includes a second magnetic structure or magnetic component 14 comprising a second magnetic array 28 implanted in a posterior pharyngeal wall.

As shown in FIGS. 7A and 7B, the arrays 26 and 28 each comprise a carrier 24, on which the magnetic materials 16 and 18 are arranged. As best shown in FIG. 7A, the carrier 24 is shaped along a longitudinal axis to have a length that is longer than its width. The longitudinally-shaped arrays 26 and 28 are implanted transverse the axis of the airway; that is, the longitudinal axis of each array 26 and 28 extends side-to-side or transversally across the mid-line of the soft palate and pharyngeal wall, respectively.

At opposite end regions of each array 26 and 28, the array 26 and 28 includes the magnetic material, respectively 16 and 18. On each array 26 and 28, the N-S poles of the magnetic materials 16 and 18 are oriented in the same direction, normal to the longitudinal axis (i.e., along the z-axis). When implanted, as FIGS. 7A and 7B show, like poles of the magnetic material 16 of the first magnetic structure or magnetic component 12 are oriented to generally align with like poles of the magnetic material 18 of the second magnetic structure or magnetic component 14 across the airway, that is, either N-N or S-S poles are generally aligned across the airway. In FIGS. 7A and 7B, the N-N poles are generally aligned. As a result, the soft palate magnetic structure or magnetic component 12 interacts by repelling the magnetic pharyngeal wall magnetic structure or magnetic component 14. The tissue in which the magnetic structure or magnetic components 12 and 14 are placed is therefore kept separated across the airway.

Figure 8A:
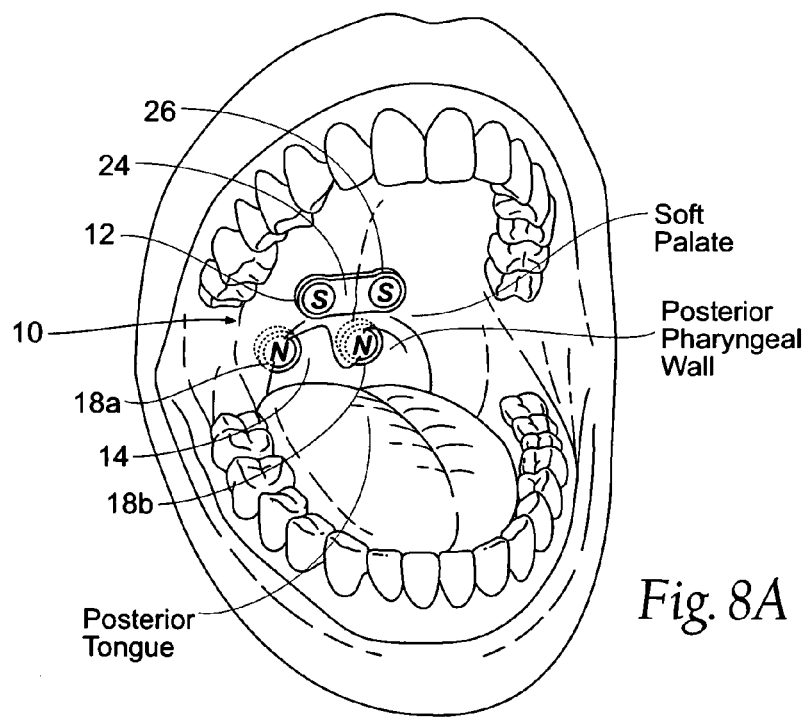
FIGS. 8A, 8B, and 8C are anatomic anterior views of other representative magnetic force systems generally of a type shown in FIG. 4, comprising magnetic materials in a soft palate and a pharyngeal wall arranged in a repelling orientation.

FIG. 8A shows a representative alternative embodiment. In this embodiment, the first magnetic structure or magnetic component 12 in the soft palate comprises a first magnetic array 26 arranged on a longitudinal carrier 24, like that shown in FIGS. 7A and 7B. In FIG. 8A, however, the second magnetic structure or magnetic component 14 in the posterior pharyngeal wall comprises separate magnetic materials 18a and 18b, not linked by a carrier 24, but individually implanted on each side of the midline of the pharyngeal wall. This arrangement of separate magnetic components 18a and 18b potentially immobilizes less surface area in the pharyngeal wall than a carrier-mounted arrangement, which may be beneficial for some apneic patients. As in FIGS. 7A and 7B, the N-S poles of the magnetic material 16 and 18a/b are oriented normal to the x-axis and y-axis of the array 26 (i.e., along the z-axis), and also along the z-axis of the materials 18a/b (in the manner shown in FIGS. 5 and 6).

When implanted, as FIG. 8A shows, the individual magnetic materials 18a and 18b are implanted so that their N-S poles are generally aligned with like N-S poles of the magnetic material 16 of the first magnetic structure or magnetic component 12 across the airway, that is, either N-N or S-S poles are generally aligned across the airway. In FIG. 8A, the N-N poles are generally aligned. As a result, as in FIGS. 7A and 7B, the soft palate magnetic structure or magnetic component 12 interacts by repelling the magnetic pharyngeal wall magnetic structure or magnetic component 14.

Figure 8B:
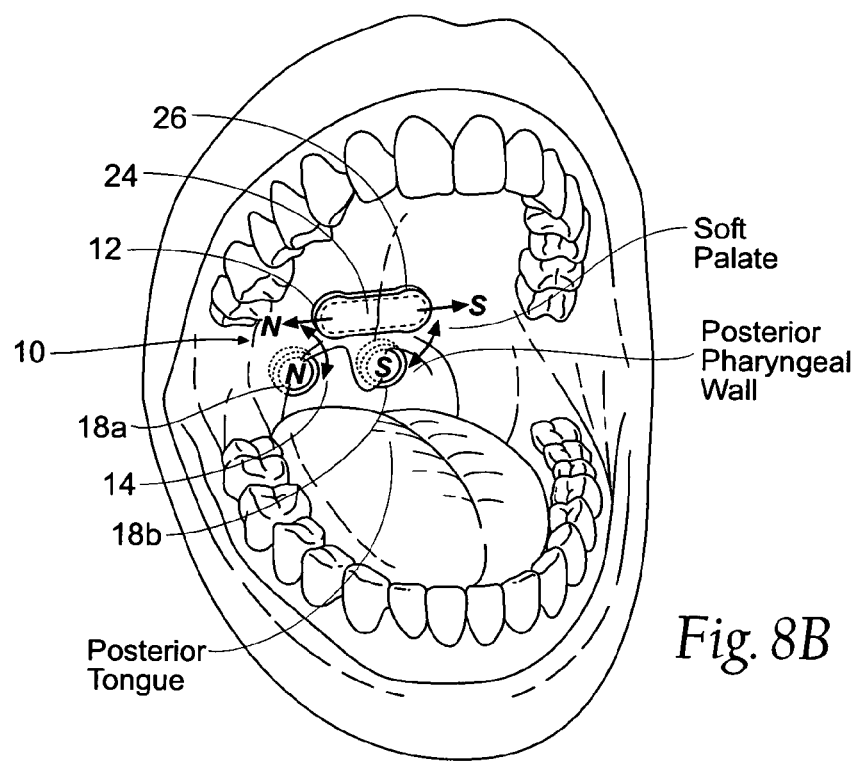

FIG. 8B shows another alternative embodiment. In this embodiment, the first magnetic structure or component 12 in the soft palate comprises a first magnetic array 26 arranged on a longitudinal carrier 24, like that shown in FIGS. 7A and 7B. As in FIG. 8A, in FIG. 8B, the second magnetic structure or magnetic component 14 in the posterior pharyngeal wall comprises separate magnetic materials 18a and 18b, not linked by a carrier 24, but individually implanted on each side of the midline of the pharyngeal wall. As before stated, this arrangement of separate magnetic components 18a and 18b potentially immobilizes less surface area in the pharyngeal wall than a carrier-mounted arrangement, which may be beneficial for some apneic patients. In the embodiment shown in FIG. 8B, the N-S poles of the magnetic material 18a/b are oriented normal to the longitudinal axis of the materials 18a/b (along the z-axis). However, in the embodiment shown in FIG. 8B, the N-S poles of the array 26 are oriented along the longitudinal x-axis, transverse to the midline of the palate. Still, the N-pole of magnetic material 18a repels the N-pole of array 26 implanted in the soft palate; correspondingly, the S-pole of magnetic material 18b repels the S-pole of array 26. In FIG. 8B, the N-N poles and the S-S poles are generally aligned, even though the magnetic fields of the pharyngeal wall materials 18a/b extend in different geometric directions than the magnetic fields of the soft palate array 26. As a result, as in FIGS. 7A and 7B, the soft palate magnetic structure or magnetic component 12 interacts by repelling the pharyngeal wall magnetic structure or magnetic component 14.

Figure 8C:
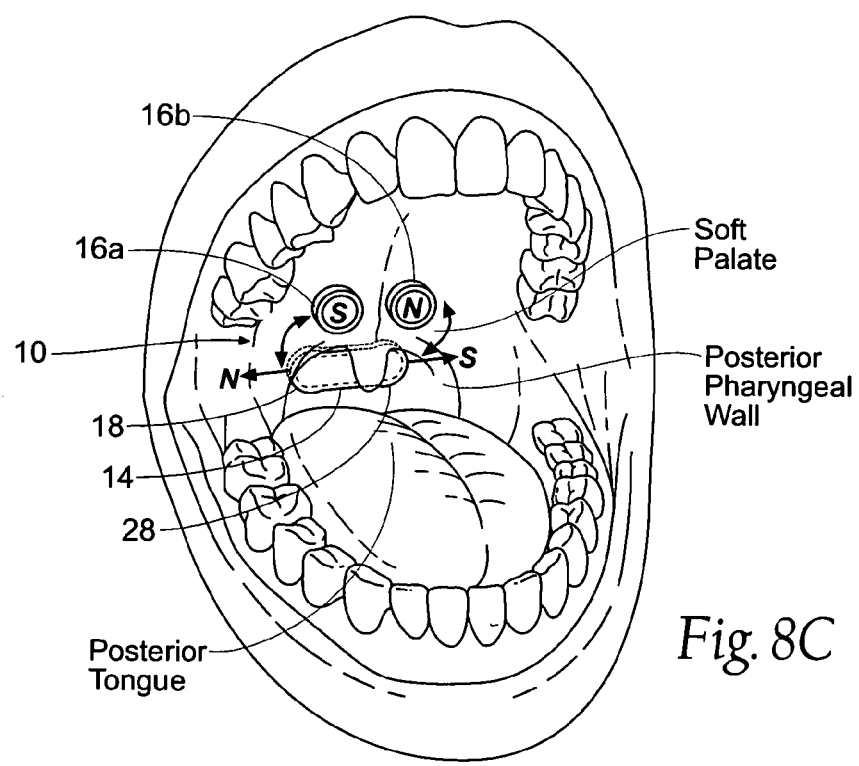

FIG. 8C shows another alternative embodiment. In this embodiment, the first magnetic structure or magnetic component 12 in the soft palate comprises separate magnetic materials 16a and 16b individually implanted on each side of the midline of the soft palate. In FIG. BC, the second magnetic structure or magnetic component 14 in the posterior pharyngeal wall comprises a unitary magnetic array 28 arranged on a longitudinal carrier 24, like that shown in FIGS. 7A and 7B. This arrangement of separate magnetic components 16a and 16b potentially immobilizes less surface area in the soft palate than a carrier-mounted arrangement, which may meet the specific needs of some apneic patients.

As in FIGS. 7A and 7B, the N-S poles of the magnetic material 16a/b are oriented normal to the longitudinal axis of the array 28 (along the z-axis). However, the N-S poles of the array 28 are oriented along the longitudinal x-axis of the array 28, transverse to the midline of the pharyngeal wall. Still, the N-pole of magnetic material 16a repels the N-pole of array 28 implanted in the pharyngeal wall; correspondingly, the S-pole of magnetic material 16b repels the S-pole of array 28. In FIG. 8C, the N-N poles are generally aligned even though the magnetic fields of the pharyngeal wall array 28 extend in different geometric directions than the magnetic fields of the soft palate materials 16a/b. As a result, as in FIGS. 7A and 7B, the pharyngeal wall magnetic structure or magnetic component 14 interacts by repelling the soft palate magnetic structure or magnetic component 12.

Figures 9A, 9B:
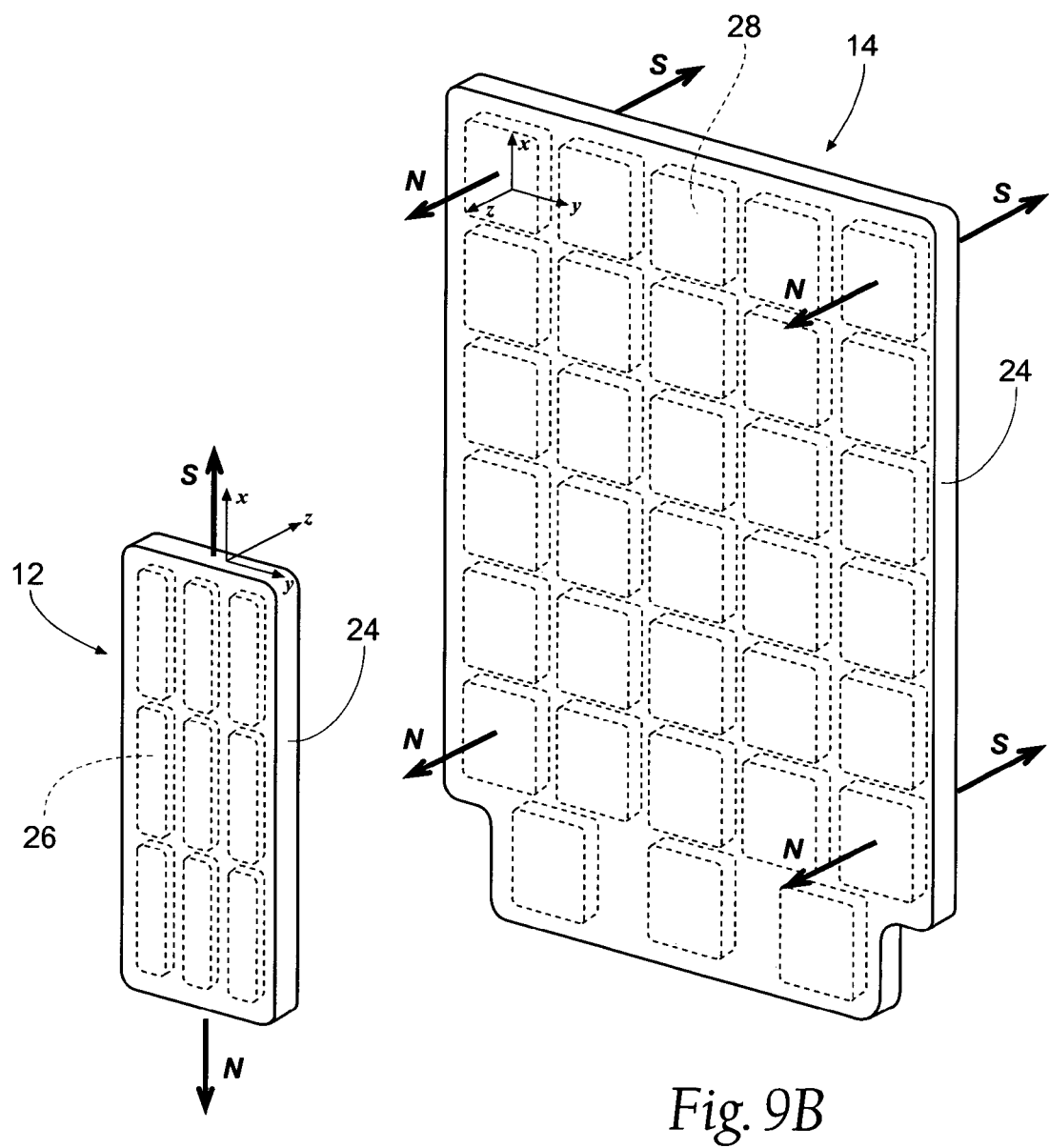
FIGS. 9A to 9D are, respectively, a front perspective view of a magnetic implant sized and configured for implantation in a soft palate, a front perspective view of a magnetic implant sized and configured for implantation in a posterior pharyngeal wall, and an anatomic anterior view and side section view of the implants shown in FIGS. 9A and 9B comprising a representative magnetic force system of a type shown in FIG. 4, comprising magnetic materials in a soft palate and a pharyngeal wall arranged in a repelling orientation.
Figure 9C:
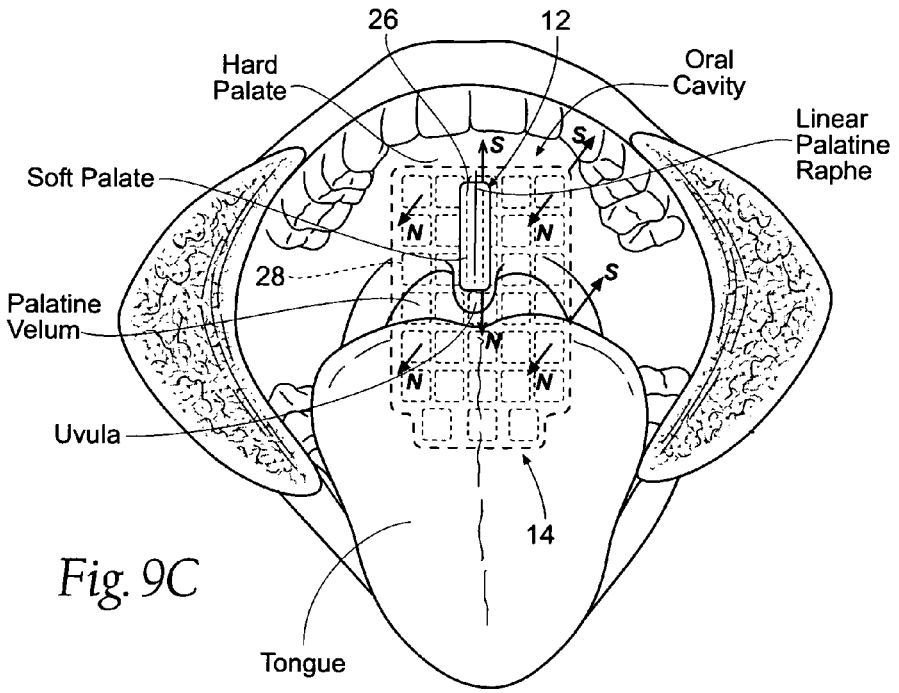

FIGS. 9A to 9D show a representative alternative embodiment. In this embodiment, the first magnetic structure or magnetic component 12 (see FIG. 9A) is sized and configured for implantation in the soft palate (see FIG. 9C). The magnetic structure or magnetic component 12 comprises a first magnetic array 26 arranged on a longitudinal carrier 24, as FIG. 9A shows. When implanted (as FIG. 9C shows), the longitudinal axis of the array 26 extends along the mid-line of the palate. As further shown in FIGS. 9C and 9D, the magnetic field of the first magnetic structure or magnetic component 12 points north at the posterior (soft palate) end of the array 26 and south at the anterior (hard palate) end of the array. In other words, the direction of the magnetic fields is along the longitudinal x-axis, as FIG. 9A shows.

Figure 9D:
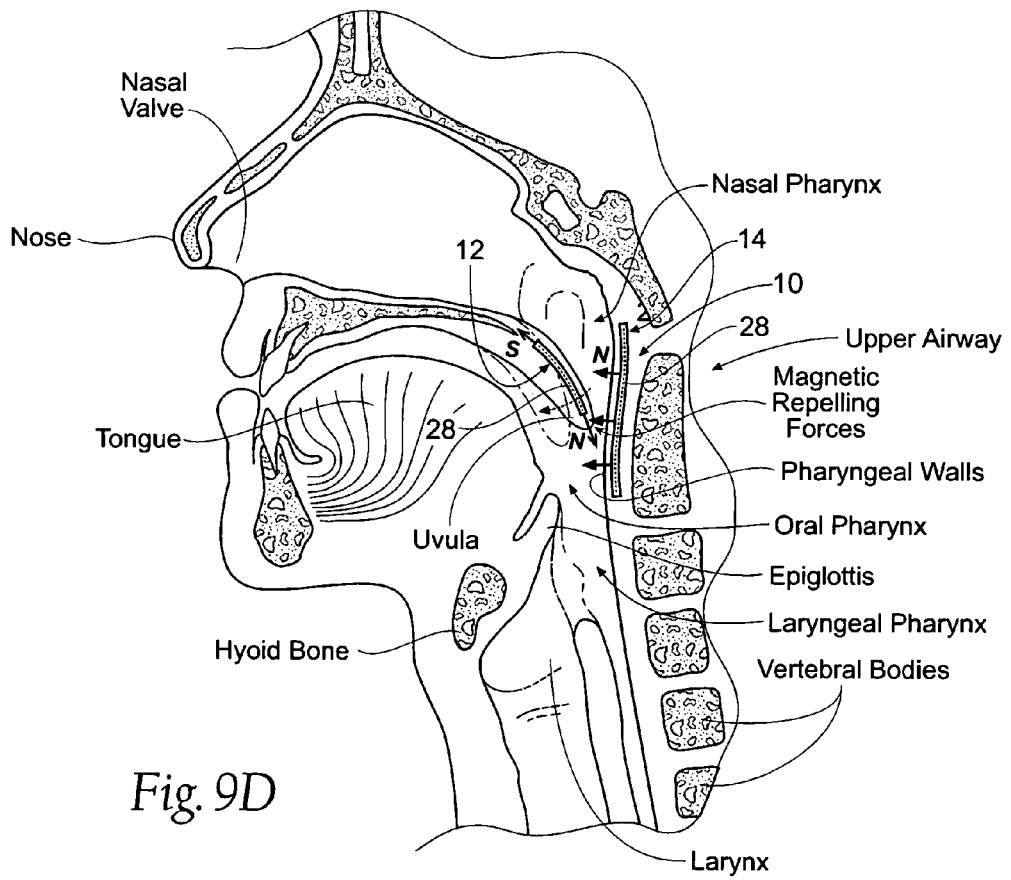

In this arrangement, the second magnetic structure or magnetic component 14 (see FIG. 9B) comprises a second magnetic array 28 sized and configured for implantation in the posterior pharyngeal wall (see FIGS. 9C and 9D). The magnetic array 28 arranged on a generally flat rectangular carrier 24 having a long axis (the x-axis), as FIG. 9B shows. When implanted (as FIGS. 9C and 9D show), the long axis of the array 26 extends along the superior-inferior axis of the posterior pharyngeal wall. As further shown in FIGS. 9C and 9D, the magnetic field of the second magnetic structure or magnetic component 14 points normal to the long axis of the carrier 24 (along the z-axis) (in the manner shown in FIG. 6). When implanted, the magnetic field points north in the anterior direction (towards the tongue and soft palate) and south in the posterior direction (toward the back of the neck) normal to the longitudinal (superior-inferior) axis of the posterior pharyngeal wall.

As FIGS. 9C and 9D show, the individual magnetic materials 18 of the second array 28 are implanted so that their N-S poles (extending normal to the long axis of the array 28) are generally aligned with like N-S poles of the magnetic material 16 of the first array 26 across the airway, that is, either N-N or S-S poles are generally aligned across the airway. In FIGS. 9C and 9D, the N-N poles are generally aligned. As a result, as in FIGS. 7A and 7B, the soft palate magnetic structure or magnetic component 12 interacts by repelling the magnetic pharyngeal wall magnetic structure or magnetic component 14.

As best shown in FIG. 9D, as the soft palate collapses against the pharyngeal wall during sleep, the posterior N-pointing end of magnetic structure or magnetic component 12 (facing the soft palate) is repelled by the north pole of the pharyngeal wall implant (which faces the airway), toward the tissue orientation shown in phantom lines in FIG. 9D. A patent airway is thereby maintained.

FIGS. 10A to 10D show another representative alternative embodiment. In this embodiment, the first magnetic structure or magnetic component 12 (see FIG. 10A) is sized and configured for implantation in the soft palate (see FIG. 10C). The magnetic structure or magnetic component 12 comprises a first magnetic array 26 arranged on a longitudinal carrier 24, like that shown in FIG. 7A. When implanted (see FIG. 10C), the longitudinal axis of the array 26 (the y-axis) extends transversely across the mid-line of the palate, in the same manner as shown in FIG. 7A. As further shown in FIGS. 10C and 10D, the magnetic field at one end of the first magnetic array 26 points north, while the magnetic field at the other end points south. That is, the direction of the magnetic field is along the y-axis.

Figures 10A, 10B:
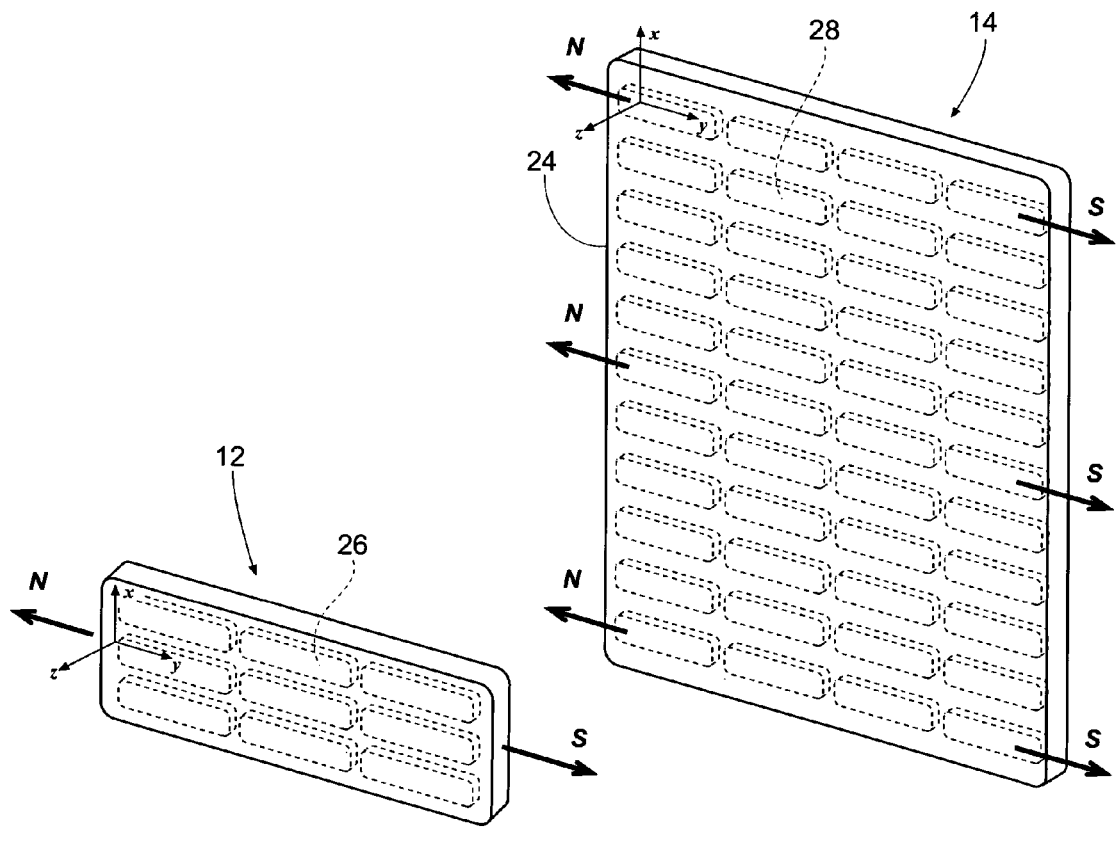
FIGS. 10A to 10D are, respectively, a front perspective view of a magnetic implant sized and configured for implantation in a soft palate, a front perspective view of a magnetic implant sized and configured for implantation in a posterior pharyngeal wall, and an anatomic anterior view and superior section view of the implants shown in FIGS. 10A and 10B comprising a representative magnetic force system of a type shown in FIG. 4, comprising magnetic materials in a soft palate and a pharyngeal wall arranged in a repelling orientation.
Figure 10C:
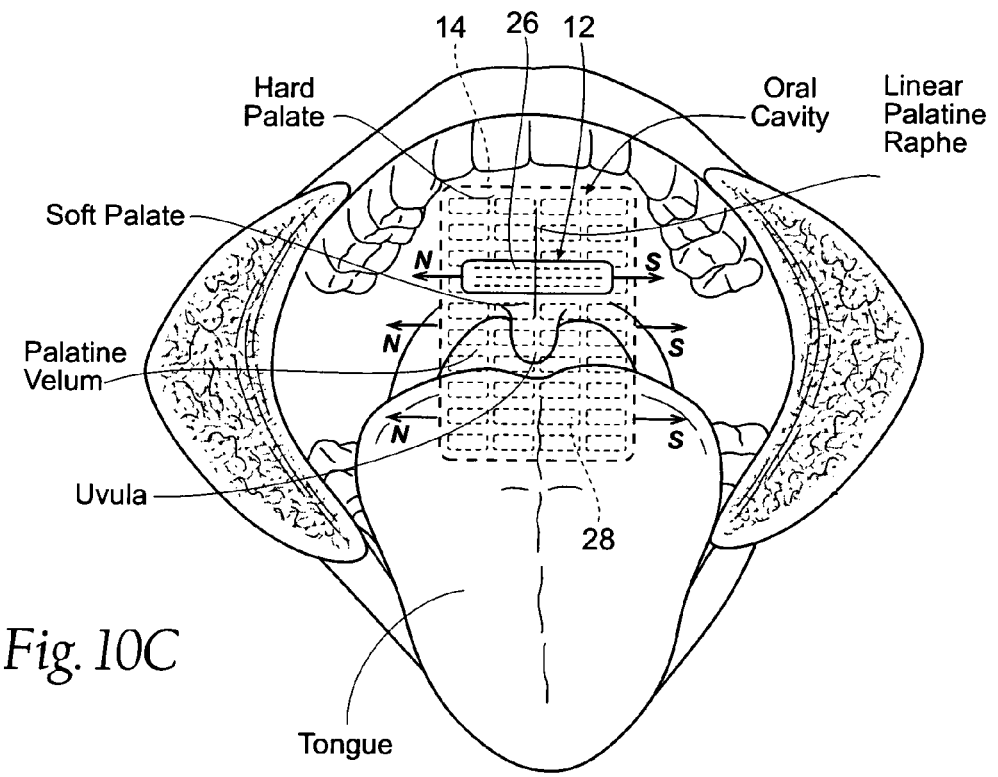
Figure 10D:
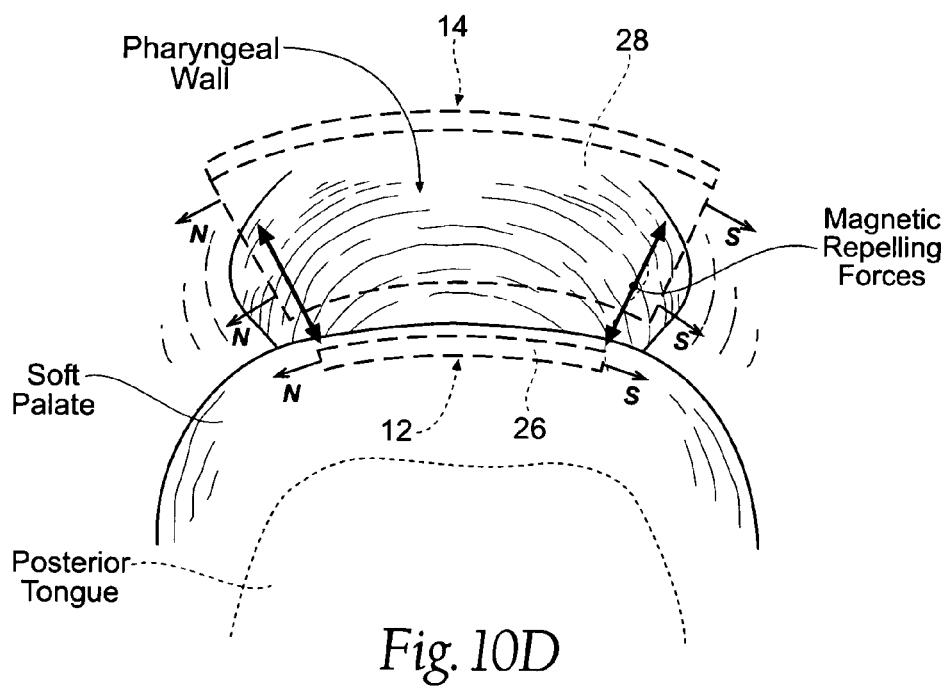

The second magnetic structure or magnetic component 14 (see FIG. 10B) is sized and configured for implantation in the posterior pharyngeal wall (see FIGS. 10C and 10D). The second magnetic structure or magnetic component 14 comprises a magnetic array 28 arranged on a generally flat rectangular carrier 24 having a long axis, as FIG. 10B shows. When implanted (as FIGS. 10C and 10D show), the long axis of the array 26 (the x-axis) extends along the superior-inferior axis of the posterior pharyngeal wall. As further shown in FIGS. 10C and 10D, the magnetic field is (similar to the first soft palate array 26) arranged to point north along one side edge of the array 28 and south on the other side edge of the array 28, transverse to the longitudinal axis of the posterior pharyngeal wall. That is, the direction of the magnetic fields in also along the y-axis.

As FIGS. 10C and 10D show, the individual magnetic materials 18 of the second array 28 are implanted so their N-S side edge poles are generally aligned with like N-S end poles of the magnetic material 16 of the first array 26 across the airway. When implanted across the pharyngeal airway (see FIG. 10D), the north end pole of the soft palate array 26 is aligned with and repels the north edge pole of the pharyngeal wall array 28 across the airway. Similarly the south end pole of the soft palate array 26 repels the south edge pole of the pharyngeal wall array 28 across the pharyngeal airway.

As a result, as in FIGS. 7A and 7B, the soft palate magnetic structure or magnetic component 12 interacts by repelling the pharyngeal wall magnetic structure or magnetic component 14. As best shown in FIG. 10D, as the soft palate collapses against the pharyngeal wall during sleep, the N-pointing end of magnetic implant 12 is repelled by the north-pointing edge of the pharyngeal wall magnetic structure or magnetic component 14, just as the S-pointing end of the magnetic structure or magnetic component 12 is repelled by the south-pointing edge of the pharyngeal wall magnetic structure or magnetic component 14. The soft palate is urged toward the tissue orientation shown in phantom lines in FIG. 10D. A patent airway is thereby maintained.

In the embodiments shown in FIGS. 7A/B, 8, 9A/B/C/D, and 10A/B/C/D, the pharyngeal wall magnetic structure or magnetic component 14 desirably provides one or more field direction(s) such that the pharyngeal magnetic structure or magnetic component 14 stays in repulsion when the palate changes its angular orientation and distance relationship to the posterior pharyngeal wall when the airway is both open and closed, e.g., during swallowing. However, the strength of the repelling force is desirably not enough to interfere with the normal processes of swallowing, speaking, etc.

Figure 11A:
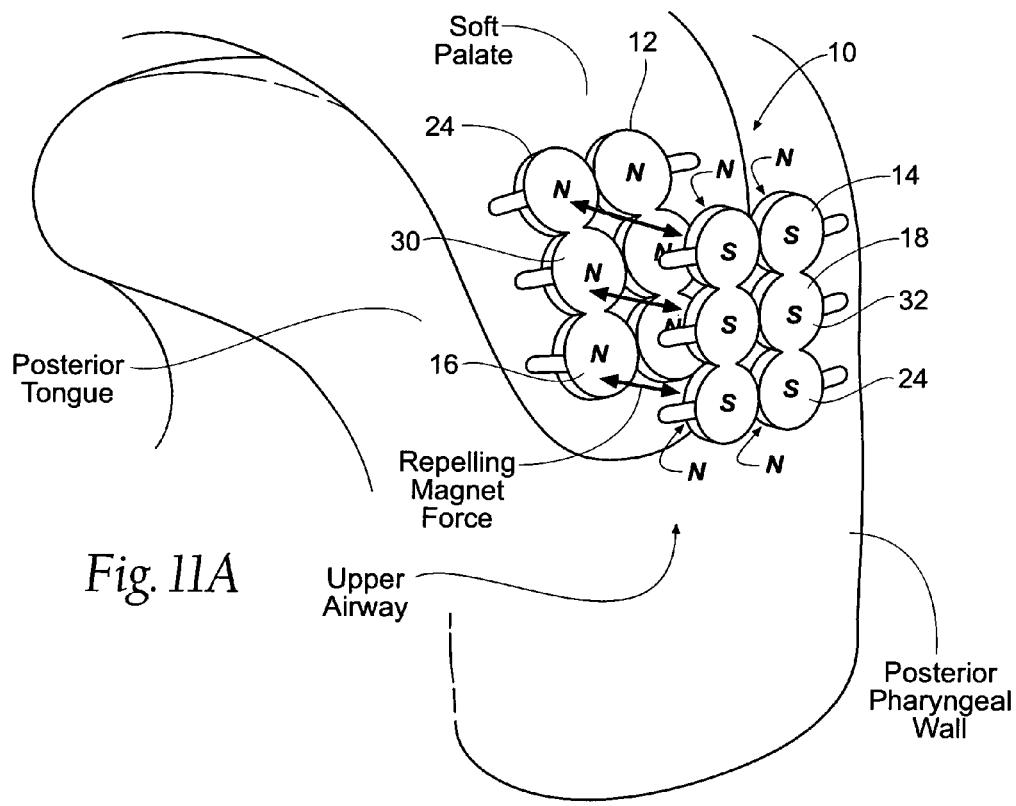
FIGS. 11A and 11B are, respectively, an anatomic posterior view and side section view of a representative magnetic force system of a type shown in FIG. 4, comprising magnetic materials in a soft palate and a pharyngeal wall arranged in a repelling orientation.
Figure 11B:
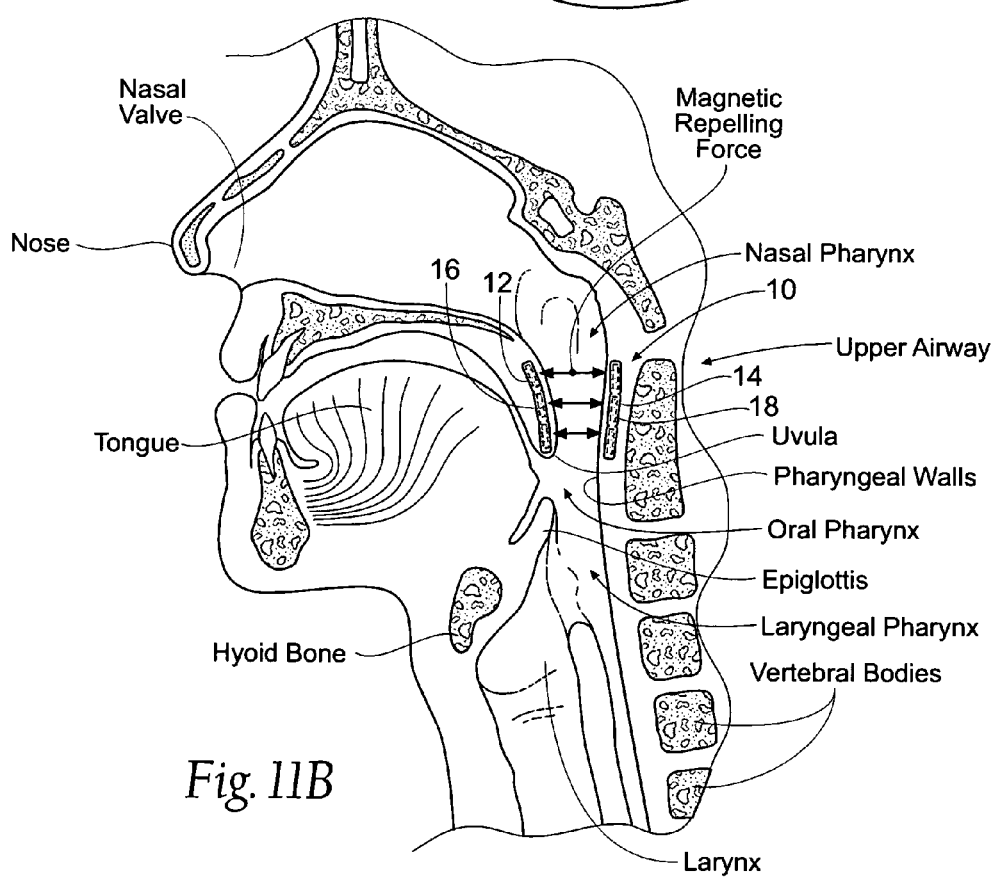

FIGS. 11A and 11B show another representative alternative embodiment of a magnetic force system 10. In FIGS. 11A and 11B, the magnetic force system 10 includes a first magnetic structure or magnetic component 12 comprising a first magnetic array 30 implanted in the soft palate (or in the uvula) and a second magnetic structure or magnetic component 14 comprising a second magnetic array 32 implanted in a posterior pharyngeal wall. As shown in FIGS. 11A and 11B, the arrays 30 and 32 each comprise a carrier 24 that is formed along a longitudinal axis to have a length that is longer than its width. In FIGS. 11A and 11B, the longitudinal arrays 30 and 32 are implanted in a superior-inferior orientation along the axis of the airway.

In FIGS. 11A and 11B, each array 30 and 32 includes a plurality of magnetic materials, respectively 16 and 18, not merely in the end regions of the implant but in the intermediate region as well. Array 30 may be flat or may include a curvature which would prevent the soft palate from collapsing during sleep. On each array 30 and 32, the N-S poles of the magnetic materials 16 and 18 are oriented in the same direction, normal to the longitudinal axis. When implanted, the poles of the magnetic material 16 of the first magnetic structure or magnetic component 12 are oriented generally in alignment with like poles of the magnetic material 18 of the second magnetic structure or magnetic component 14 across the airway, that is, either N-N or S-S poles are generally aligned across the airway (in both, the direction of the magnetic fields is along the z-axis). In FIGS. 11A and 11B, the N-N poles are generally aligned. As a result, the soft palate magnetic structure or magnetic component 12 interacts by repelling the pharyngeal wall magnetic structure or magnetic component 14.

Figure 11C:
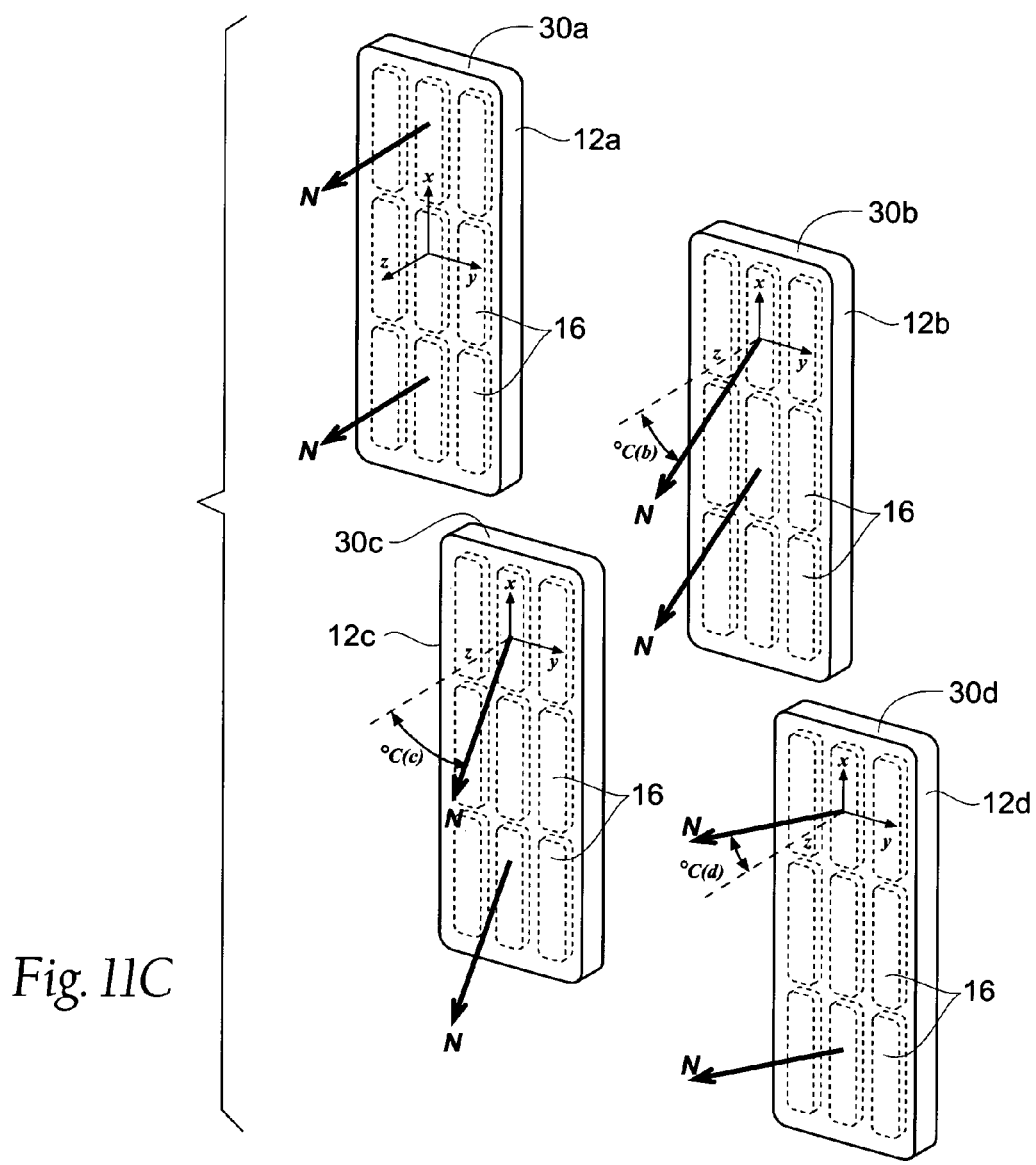
FIGS. 11C and 11D show perspective views of a family of implant devices having different magnetic field orientations sized and configured to be implanted in a soft palate in a manner that permits selection of a desired magnetic field orientation that provides the desired therapeutic result.

The orientation between the soft palate and the pharyngeal wall varies among individuals. It also varies for a given individual from point to point along the airway. For a given soft palate implant and a corresponding pharyngeal wall implant, the orientation of the magnetic fields can differ due to the differences in the anatomy of the airway among individuals. FIG. 11C, shows a family 200 of implant devices 12a, 12b, 12c, and 12d. The implant devices 12a, 12b, 12c, and 12d are each sized and configured for implantation in a soft palate in association with an implant in a posterior pharyngeal wall in the manner described. The implant devices 12a, 12b, 12c, and 12d are further configured to make possible an objective assessment, for a given individual, of an optimal orientation of magnetic fields to achieve the desired therapeutic effect.

As shown in FIG. 11C, each implant device 12a, 12b, 12c, and 12d comprises one or more magnetic materials 16 carried in support carrier 30a, 30b, 30c, and 30d. While all of the magnetic materials 16 in each support carrier 30a, 30b, 30c, and 30d are oriented in generally the same direction (i.e., generally in the direction of z-axis), the direction of the N-S poles of magnetic material 16 relative to the z-axis differs among devices 12a, 12b, 12c, and 12d. In the device 12a, the magnetic field is oriented parallel to the z-axis (normal to the x-axis and y-axis of the support carrier 30a). However, in the devices 12b, 12c, and 12d the magnetic fields are not oriented normal to the x-axis and y-axis of the support carrier 30b, 30c, and 30d (i.e., they are not all parallel to the z-axis). Instead, the magnetic fields of the magnetic material 16 in the support carriers 30b, 30c, and 30d have directions that are oriented at different angles ° C.(b), ° C.(c), and ° C.(d) from the z-axis.

In particular, as shown in FIG. 11C, there are at least first and second sources of magnetism 16 carried by each carrier structure 30b, 30c, and 30d. Each source generates a magnetic field having a direction. The directions are oriented at an angle ° C. from the z-axis, indicated angle ° C.(b) for device 12b, angle ° C.(c) for device 12c, and angle ° C.(d) for device 12d. In FIG. 11C, for a given structure 30b, 30c, and 30d, the respective angle ° C.(b), ° C.(c), ° C.(d) for all the sources of magnetism on the given carrier structure is essentially equal. However, the angle ° C.(b) on carrier 30b is different than the angle ° C.(c) on carrier 30c, and the angle ° C.(d) on carrier 30d is different than either angle ° C.(b) or ° C.(c). On the support carrier 30a, the magnetic field is parallel to the z-axis, that is, the angle is zero, and is therefore also different than any of the angles ° C.(b), ° C.(c), and ° C.(d).

The differing directions of magnetic fields provide the family 200 of implant devices 12a to 12d shown in FIG. 11C. Each device 12a to 12d comprises a source of magnetism having a magnetic field orientation, and the magnetic field orientations of the implant devices 12a to 12d differ among the devices in the family. Various embodiments of implant devices can be manufactured where the angle ° C.(n) varies from zero to 90° on either side of the z-axis (i.e., either superior or inferior of the z-axis—or, as expressed as an angle measured along the x-axis, from zero to 180°).

During the implantation surgery, one or more implants of the family can be separately placed in the surgical pockets in order to determine which angle between the N-S poles and the longitudinal carrier offers the best therapeutic effect.

Figure 11D:
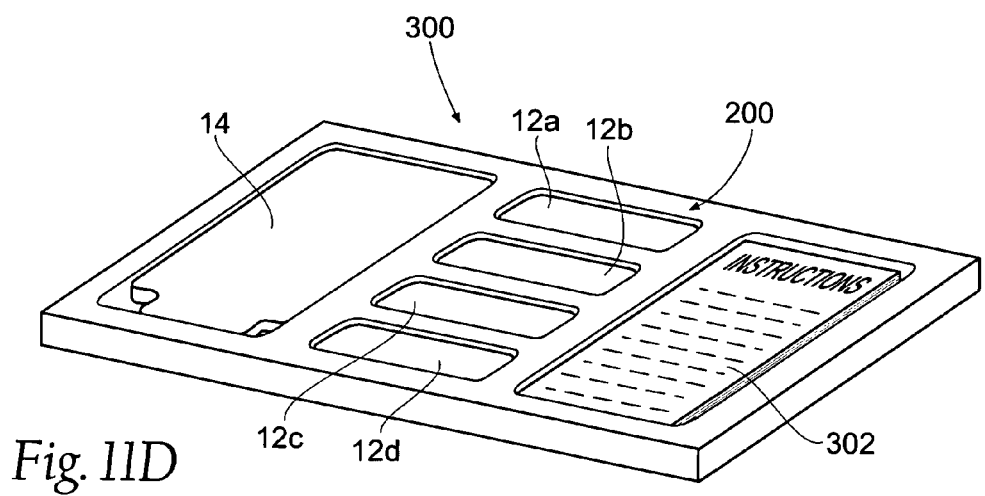

FIG. 11D shows a representative embodiment of an implant system 300, which can be provided to a clinician as a unitary form, e.g., in the form of a kit. The system or kit 300 includes an magnetic structure or magnetic component 14 for placement in or on one tissue region, e.g., a pharyngeal wall. The system or kit 300 also includes the family 200 of implant devices 12a to 12d, as just described, which are sized and configured for placement in or on another tissue region, e.g., a soft palate, for magnetic interaction with the magnetic structure or magnetic component 14. Each device 12a to 12d comprises a source of magnetism having a magnetic field orientation, and the magnetic field orientations of the implant devices 12a to 12d differ among the devices 12a to 12d in the family 200, as already described. The system or kit 300 can further include instructions 302 to the clinician for using the system or kit 300 to achieve a desired therapeutic effect.

In a representative embodiment, the instructions 302 can direct a clinician to separately place two or more of the implant devices 12a to 12d in or on tissue in a tissue region for interaction with a second magnetic structure or magnetic component 14, which is placed in or on another tissue region different than the first tissue region. The instructions 302 can also direct a clinician to assess, as a function of the magnetic field orientation for each device 12a to 12d of the family 200 that is implanted, a therapeutic effect, which is observed or measured based upon the nature of the interaction between each of the two or more implant devices 12a to 12d and the other magnetic structure or magnetic component 14. The instructions 302 can further direct the clinician to select based, at least in part, upon that assessment, a desired magnetic field orientation that provides a desired therapeutic effect. The clinician thereafter can permanently implant a device having the desired magnetic field orientation ascertained in this manner.

In the context of the system 10 already discussed, the instructions 302 can direct placing a magnetic structure or magnetic component 14 in or on tissue on a posterior pharyngeal wall to magnetically interact with a magnetic structure or magnetic component 12 in or on tissue in a soft palate. The magnetic structures or magnetic components 12 and 14 are sized and configured to interact to develop a magnetic force that maintains separation between the soft palate and the posterior pharyngeal wall.

In this arrangement, the instructions can direct placing, as the soft palate magnetic structure or magnetic component 12, an implant device having a desired magnetic field orientation by a purposeful selection process. The selection process separately places two or more candidate implant devices 12a to 12d from the family 200 in or on tissue in a soft palate in interaction with the magnetic structure or magnetic component 14. The instructions can direct assessing, as a function of the magnetic field orientation, a therapeutic effect of the interaction between each of the two or more candidate implant devices 12a to 12d and the magnetic structure or magnetic component 14 in the pharyngeal wall. The instructions can also direct selecting, as the desired magnetic field orientation, the magnetic field orientation that provides a desired therapeutic effect based, at least in part, upon that assessment. In this way, an implant device having the desired magnetic field orientation can be identified and selected for use. The clinician thereafter can permanently implant a magnetic structure or magnetic component 12 having the desired magnetic field orientation ascertained in this manner.

To minimize the possibility of extrusion or to provide stability to the unstable repelling implants, the soft palate magnetic structures or magnetic components 12 are implanted into pockets of soft palate tissue; and may be attached via sutures; attached to the connection tissue near the hard/soft palate junction; or anchored to the bony mass at the junction of the hard and soft palate.

The various magnetic force systems 10 as described provide an elegant, cost-effective treatment of sleep apnea. Placed in or on tissue in the soft palate and the pharyngeal wall, the magnetic structures or magnetic components 12 and 14 are well tolerated and are significantly more comfortable and user friendly than CPAP or the highly intrusive surgical treatment options. The magnetic system 10 offers a sophisticated, yet easy to use design, which can be shaped, configured, and magnetically titrated by adjusting the size of implant magnets or their angular magnetic field orientation to meet patients' individual needs, based upon specific anatomic requirements, as will be described in greater detail later.

III. Magnetic Structures for the Soft Palate

A. Magnetic Instability (Torque) in Repelling Magnetic Systems

As shown in FIG. 12A, the magnetic structures or magnetic components 12 and 14 are desirably generally aligned along the airway formed between the soft palate and posterior pharyngeal wall to create a repelling magnetic force field. However, in reality, there is never a theoretical "perfect" magnetic alignment between the repelling magnetic materials 16 and 18. This is due to the anatomy of this region of the airway, coupled with the dynamic nature of the soft palate itself. The orientation between the soft palate and the pharyngeal wall varies from point to point along the airway. There is rarely a geometrically "perfect," parallel relationship between the two tissue structures. Further, as FIGS. 12B and 12C show, when the soft palate moves, e.g., during swallowing, the movement can significantly alter the orientation and alignment between the repelling magnetic materials 16 and 18 from one moment to another.

From a purely physical standpoint, Earnshaw's theorem states that there is no possible static configuration in the absence of stabilizing forces, in which repelling magnetic materials can achieve a stable state. [Earnshaw S. On the nature of the molecular forces which regulate the constitution of the luminiferous ether. Trans Camb Phil Soc 1842, 7:97-112.] At the slightest misalignment from the "perfectly" magnetically aligned positions, two repelling magnets will start to move to position themselves in an attracting mode, because this is their lowest energy state. While torque is present in all imperfectly aligned systems, whether attracting or repelling, when repelling magnets are not in "perfect" alignment, where there is misalignment by angle or position, the torque can increase rapidly.

For a more scientifically rigorous presentation of the above-mentioned material, Earnshaw's theorem states that there is no possible static stable configuration of objects subject to a combination of inverse square law forces. Such forces include gravity and magnetism, as applied to our product, but do not include stabilizing forces provided by the palate. In essence, Earnshaw showed that inverse square law forces have no local minimum or maximum in their energy field, so they will always move, slide, and/or spin until they find a stabilizing force (generally when they are touching in attraction, which is the lowest energy state of a pair of magnets.) In our system, the palate and pharyngeal walls will provide stabilizing forces (which do not follow the inverse square law), to prevent this from happening. Variations in the force across an implant (or a magnet, or any other object) are interpreted as torques, and are present in any magnetic system that is not in perfect alignment.

Magnetic structures placed in or on mobile anatomic structures in the airway are seldom, if ever, orientated in a way that permits theoretically "perfect" alignment of repelling magnets. The alignment of the repelling magnetic materials is rarely "perfect," and it is subject to continuous change. It is by understanding and controlling the torque inherent in repelling magnetic systems, that the soft palate can be effectively manipulated for the therapeutic purposes disclosed herein.

B. Design Considerations

Any repelling magnetic system involving the soft palate desirably takes into account and balances two considerations: (i) one consideration is anatomic—it is the lack of perfect parallel alignment between the soft palate and the pharyngeal wall in the airway, which is compounded by the natural movement of the soft palate relative to the pharyngeal wall, and (ii) the other consideration is physical—it is the torque or decentering force that interaction of repelling magnetic forces creates in systems where less than perfect alignment occurs, as explained by Earnshaw's theorem.

A given repelling soft palate implant should desirably be maintained in a position of repulsion (and not attraction) as other structures, such as the soft palate, move in relation to the pharyngeal wall. For example, it should be recognized that during the process of chewing and swallowing, the soft palate undergoes a cyclical process of up and down motions and changes of angular orientation to the pharyngeal wall and comes into contact with the pharyngeal wall [Matsuo K, Hiiemae K M, and Palmer J B. 2005. Cyclic motion of the soft palate in feeding. J Dent Res 84(1):39-42.]. Such contact normally occurs during swallowing and not just during an abnormal apneic attack.

A given soft palate implant desirably includes features for maintaining the implant in its repelling state at all the angular alignments normally and abnormally encountered with respect to the pharyngeal wall but should still allow for closure of the soft palate during swallowing and speech. In addition a given repelling soft palate implant must take into account the varying anatomical angles, distances and features encountered in a diverse patient population. Not only is there variability from patient to patient, but also within a single patient C. The Edge Effect We have discovered that maintaining implants in a repelling position with respect to each other requires particular attention to magnetic forces that are generated at the edges of the implant. As FIGS. 12B and 12C demonstrate, as soon as the edges of the implants (initially repelling) start to misalign, the magnets at the edges of the implant may start to twist in an attempt to orient themselves to a more desired attracting arrangement. This can cause an implant to twist and flip.

For example, FIG. 12A shows the N-pole of the soft palate magnetic structure or magnetic component 12 initially oriented in an alignment with respect to the repelling N-pole of the pharyngeal wall magnetic structure or magnetic component 14 that is conducive to repelling. However, as FIGS. 12B and 12C show, as the soft palate naturally moves up and back, or when it abnormally collapses during an apneic episode, the N-pole of the magnets on an edge region of the soft palate magnetic structure or magnetic component 12 can come out of the existing beneficial alignment with the N-pole of the magnets on the pharyngeal wall magnetic structure or magnetic component 14. As alignment changes, the S-pole of magnets on the soft palate magnetic structure or magnetic component 12 can move progressively into attracting alignment with the N-pole of the magnets of the pharyngeal wall magnetic structure or magnetic component 14 (FIG. 10C). Torquing and attracting forces are generated by this misalignment (according to Earnshaw's theorem). As a result, the soft palate magnetic structure or magnetic component 12 may start to flip or further torque to move into a position of attraction with respect to the pharyngeal wall magnetic structure or magnetic component 14. This further torque can offset the repelling forces generated by the implants and, along with the attracting force from the closer proximity of the opposite S-pole, pull the palate closed.

To overcome and control these flipping and twisting tendencies, which also takes into account the anatomic and physical considerations described above, an implant desirably manipulates and adjusts the nature of the magnetic fields in certain regions of the implant, particularly along one or more edges of the implant. The manipulation and adjustment of the magnetic fields makes certain that, even though some of magnetic poles are not in or may fall out of "perfect" repelling alignment with another magnet, there will be at least some magnetic poles that are maintained in a repelling alignment sufficient to resist twisting or flipping the entire implant or pulling of the palate closed.

D. Angled Magnetic Fields

In one arrangement, the flipping and twisting tendencies can be overcome or at least controlled by the inclusion of magnetic fields that are mutually angled within the implant and/or along one or more edges of the implant. The angling of magnetic fields makes certain that even though some of magnetic poles may fall out of repelling alignment with another magnet, there will be at least some magnetic poles that are maintained in a repelling alignment with respect to repelling magnetic poles of the other magnet.

Figure 13:
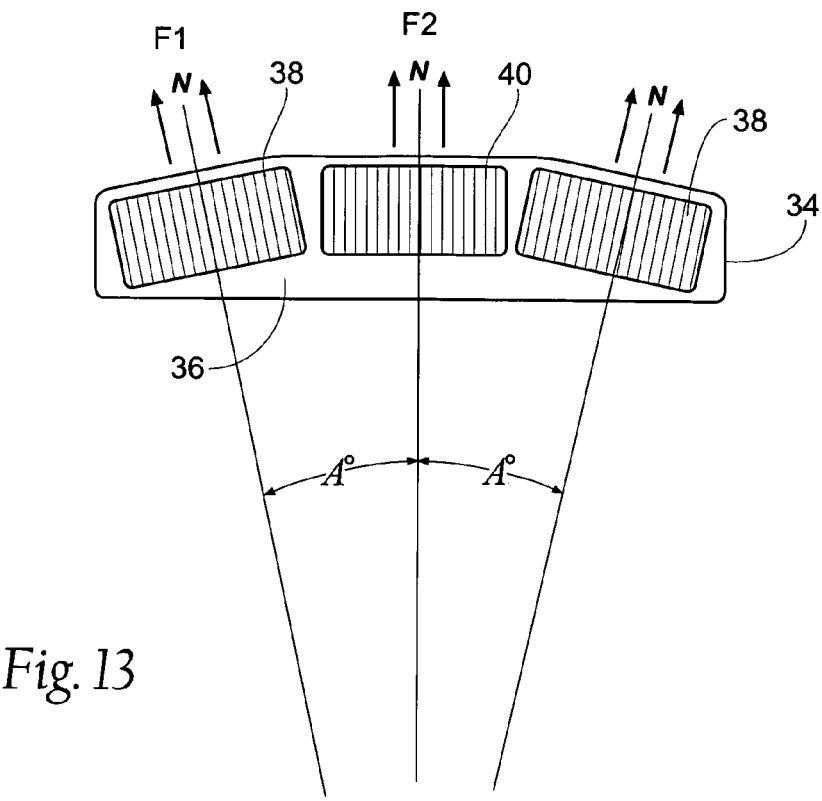
FIG. 13 shows a longitudinal cross-section view of a representative magnetic implant sized and configured in a generally planar carrier for implantation in a soft palate that includes magnetic fields that are mutually angled within the implant and/or along one or more edges of the implant.

FIG. 13 shows a representative magnetic implant 34 sized and configured for implantation in a soft palate that embodies this feature. The implant 34 comprises a carrier structure 36 sized and configured for placement in or on tissue. The implant 34 includes at least two sources 38 and 40 of magnetism carried by the carrier structure 36. Each source 38 and 40 generates a magnetic field, similar to that shown in FIG. 11 as a first force field F1 and a second force field F2, respectively. The sources 38 and 40 can each comprise a permanent magnet, as previously described.

As FIG. 13 shows, the first and second magnetic fields F1 and F2 have a direction. The magnetic fields F1 and F2 each comprises either a north polarity N or a south polarity S, as previously described. In FIG. 11, the fields comprise a north polarity N. The first and second fields F1 and F2 of the implant 34 have the same polarity; that is, they are either both N-poles or both S-poles. In FIG. 13, they are both N-poles. This arrangement is consistent with the configuration of implants previously described.

However, unlike the previously-discussed implants, in the implant 34 shown in FIG. 11, the direction of the first magnetic field F1 is orientated at an angle A from the direction of the second magnetic field F2. It is this angularity between or among the plurality of fields F1 and F2 of the implant 34, particularly when placed at one or more edges of the implant 34, that keeps the implant 34 from flipping or twisting in a repelling force field that is not in perfect alignment with another repelling implant and/or that is subject to change in alignment in response to the natural movement of anatomic structures.

The angularity (i.e., the magnitude of Angle A) can be selected empirically based upon general anatomic considerations for a population of individuals, or the angularity can be customized for a given implant according to the anatomic configuration of a particular individual's soft palate. In this arrangement, the individual undergoes fluoroscopy to image the individual's soft palate. Based upon the images of the soft palate, the clinician can assess the morphology of the soft palate and determine a desirable angularity of the magnetic fields of the soft palate implant 34. In this way, based on the individual's particular anatomical requirements, a magnetic soft palate implant with angled magnetic fields can be assembled and implanted. It has been discovered that, for a soft palate implant, the angle A is desirable to be at least 10 degrees.

In FIG. 13, the angularity between the fields F1 and F2 is achieved by physically orienting the pole direction of the source 38 to face a different direction than the pole of the source 40. In the arrangement, the carrier structure 36 possesses a generally planar configuration prior to implantation.

Figure 14:
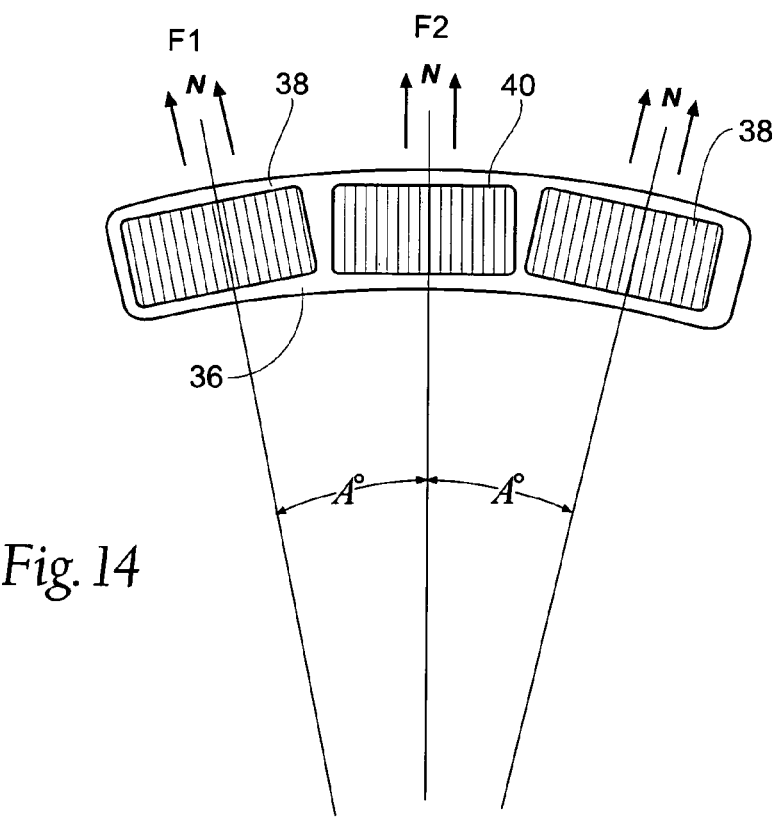
FIG. 14 shows a longitudinal cross-section view of a representative magnetic implant sized and configured in a generally curved or flexed carrier for implantation in a soft palate that includes magnetic fields that are mutually angled within the implant and/or along one or more edges of the implant.

In FIG. 14, the angularity between the fields F1 and F2 is achieved by physically orienting the pole direction of the source 38 to face the same direction as the pole of the source 40, and by flexing the carrier structure 36 to form the requisite angle A. The flexure can comprise a preformed curve, or the flexure can occur during implantation, as the carrier structure conforms to the curve morphology of the soft palate itself.

FIGS. 15A/B/C and 16A/B/C show embodiments of a magnetic force system 10, which includes a magnetic implant 34 of the type shown in FIGS. 13 and 14 (respectively). The magnetic implant 34 is implanted in the soft palate in an anterior-to-posterior direction. The magnetic implant 34 magnetically interacts with a repelling second magnetic implant 42, which is implanted in a posterior pharyngeal wall in a superior-to-inferior direction.

In FIGS. 15A/B/C and 16A/B/C, the implants 34 and 42 each includes a plurality of magnetic materials, respectively 38/40 (corresponding to what is shown in FIGS. 13 and 14) and 18. The N poles of the magnetic materials 38/40 and 18 are oriented to generally align with each other across the airway, forming an adequate repelling relationship, albeit not "perfect" in a physical sense.

Figure 16A:
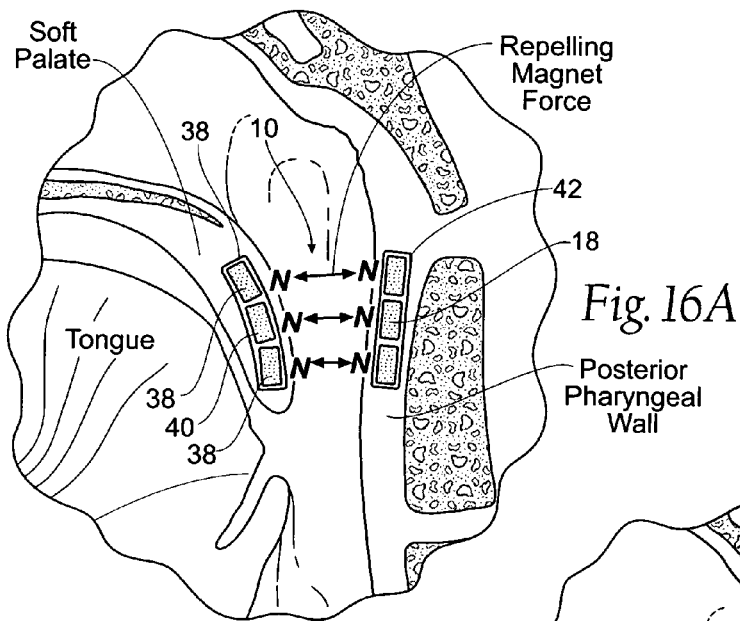
FIGS. 16A, 16B, and 16C are anatomic side section views of the implant shown in FIG. 14 implanted in a soft palate in alignment with a magnetic implant in a pharyngeal wall, showing that, as the soft palate moves, e.g., during swallowing, the repelling orientation and alignment between the magnetic implants is maintained.
Figure 16B:
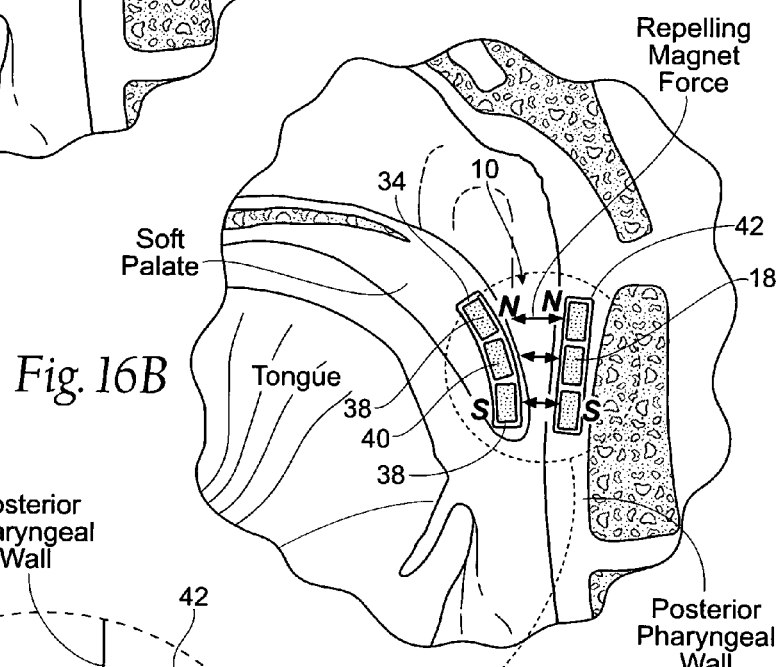
Figure 16C:
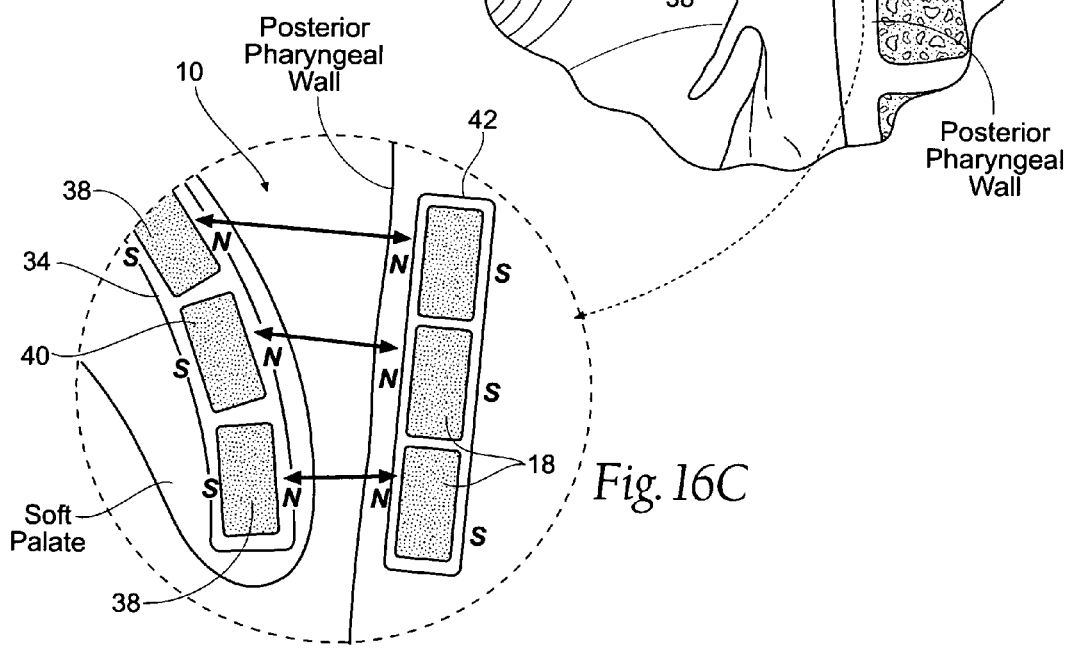

The directions of the magnetic fields of the N-poles of pharyngeal wall implant 42 are generally the same, being normal to the pharyngeal wall implant 42 and hence normal to the pharyngeal wall. However, the direction of at least one of the N-pole magnetic fields of the palate implant 34 is orientated at an angle of at least 10-degrees from the direction of another N-pole magnetic field on the palate implant 34. In FIGS. 15A/B/C, a generally planar implant as shown in FIG. 13 is implanted, in which the angularity is achieved by orienting the pole of at least one magnet 38 differently than the pole or poles of other magnets 40. In FIGS. 16A/B/C, a curved implant as shown in FIG. 14 is implanted, in which the angularity between the magnets 38 and 40 is achieved by virtue of the curve of the implant carrier.

Figures 17A, 17B, 17C, 17D:
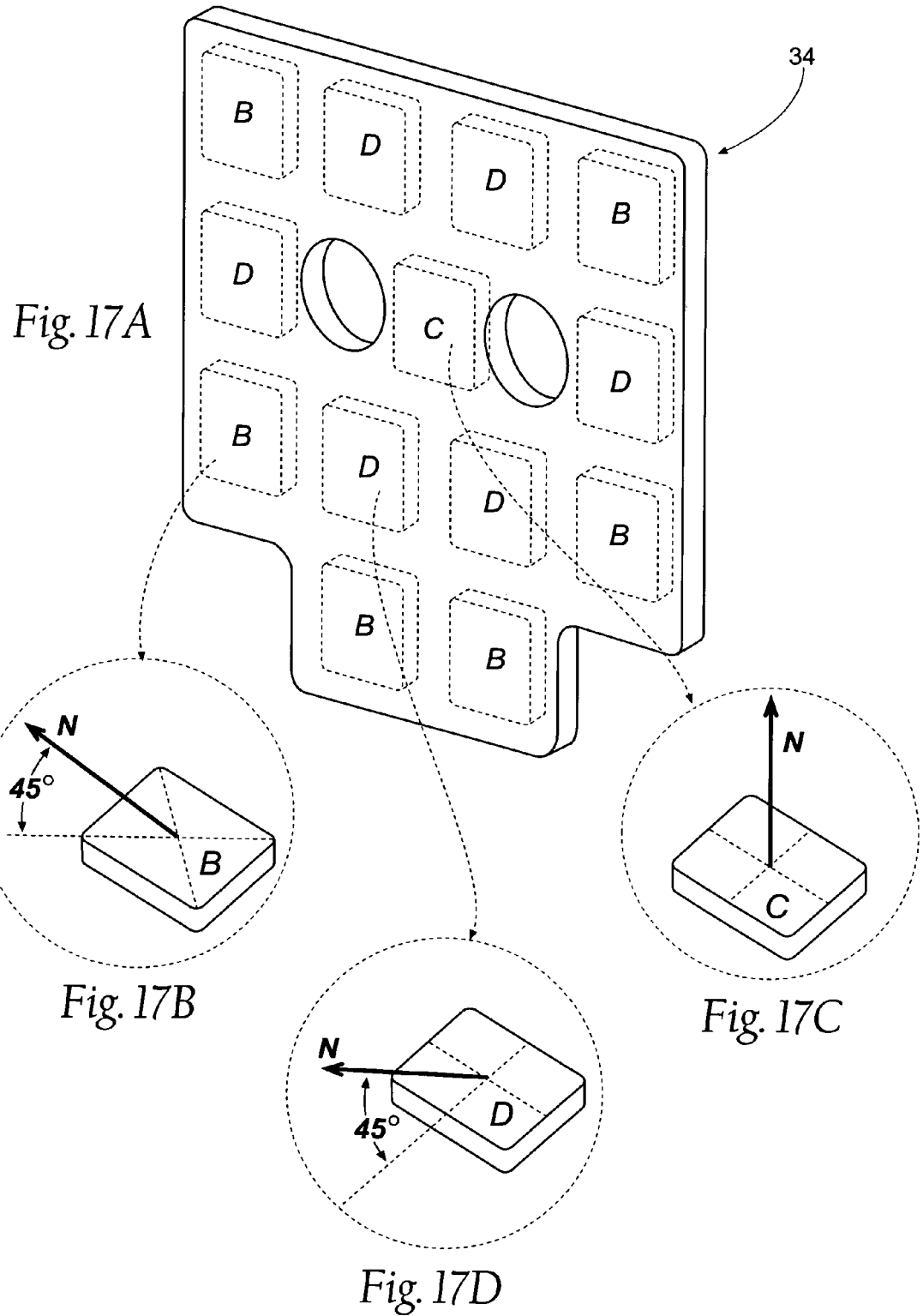
FIG. 17A is a perspective front view of a magnetic implant that includes a plurality of magnetic materials, shown in FIGS. 17B, 17C, and 17D, respectively, having magnetic fields that are angled in different directions.

FIGS. 17A to 17D show an alternative embodiment. In this embodiment, the implant 34 includes a variety of magnetic materials, designed B, C, and D in FIG. 17A and as shown in FIGS. 17B, 17C, and 17D, respectively, having magnetic fields that are angled in different directions. Thus, the angularity can be achieved not just by physically angling magnets relative to one another (as shown in FIGS. 15A/B/C and 16A/B/C, but also by creating fields within a magnet that are angled as part of the magnet. This result can be achieved in different ways. In the representative embodiment shown in FIGS. 17A to 17D, the N-poles of the magnetic materials D are oriented at a 45° angle with respect to the outer edge of the magnets. The N-poles of the magnetic materials B of the corner magnets, are oriented at a 45° angle with respect to the line starting at the intersection of magnetic material D's diagonals and continuing to the outer corner. The N pole of the magnetic material C is oriented normal to the surface of the magnet. This particular configuration allows the soft palate implant to be repelled from the pharyngeal wall implant from a variety of angles.

Angling the magnetic field of at least one magnet in the soft palate implant 34, using an angle A that is either determined empirically or according to the particular anatomical configuration of an individual's soft palate, allows at least one magnet of the magnetic soft palate implant 34 to remain in repelling alignment with at least one magnet in the magnetic pharyngeal wall implant 42, regardless of any particular anatomic misalignment due to the configuration of the soft palate and changes in the angular alignment between the soft palate and pharyngeal wall during natural movement. The implant 34 therefore enhances the intended function of the implant 34 in keeping the pharyngeal airway open. Even should the soft palate collapse during sleep, the angling of the magnetic field(s) of the soft palate magnet(s) maintains the repelling interaction of the soft palate implant 20 and the pharyngeal wall implant 22, thus preventing apneic events.

E. Radial Magnetic Fields

A radial magnet is a magnet whose internal magnetic polarization changes direction along one of more of its dimensions. More generally, magnets may be constructed with variable or multiple (magnetic) field directions.

Figure 18:
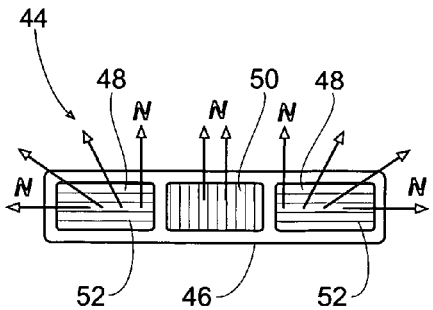
FIG. 18 is a longitudinal cross-section view of a magnetic implant having a carrier structure that is sized and configured for placement in or on tissue in a soft palate, and that includes at least one source of magnetism that comprises a permanent magnet with radial magnetization.

FIG. 18 shows a magnetic soft palate implant 44 comprising a carrier structure 46 sized and configured for placement in or on tissue. The implant 44 includes at least two sources 48 and 50 of magnetism carried by the carrier structure 46. At least one of the sources 48 and 50 comprises a permanent magnet 52 with radial magnetization. The magnetic flux field of the radial magnet 52 extends radially from the center of the magnet, as shown by arrows in FIG. 18. The permanent radial magnet 52 presents the same magnetic pole (north or south) about its entire outer surface. The presence of the radial magnet 52 may be desirable, particularly on the lower edge of a soft palate implant 44, because the radial flux field can overcome problems associated with attraction at the edges of the implants.

Alternatively, at least one of the sources 48 and 50 comprises a permanent magnet 52 with variable magnetic field direction. The magnetic flux field of the variable field direction magnet 52 extends in variable directions from the center of the magnet, as shown by arrows in FIG. 15. The permanent variable field direction magnet 52 presents a varying magnetic pole (north or south) about its outer surface. The presence of the variable field direction magnet 52 may be desirable, particularly on the lower edge of a soft palate implant 44, because the variable direction flux field can overcome problems associated with attraction at the edges of the implants.

Figure 19A:
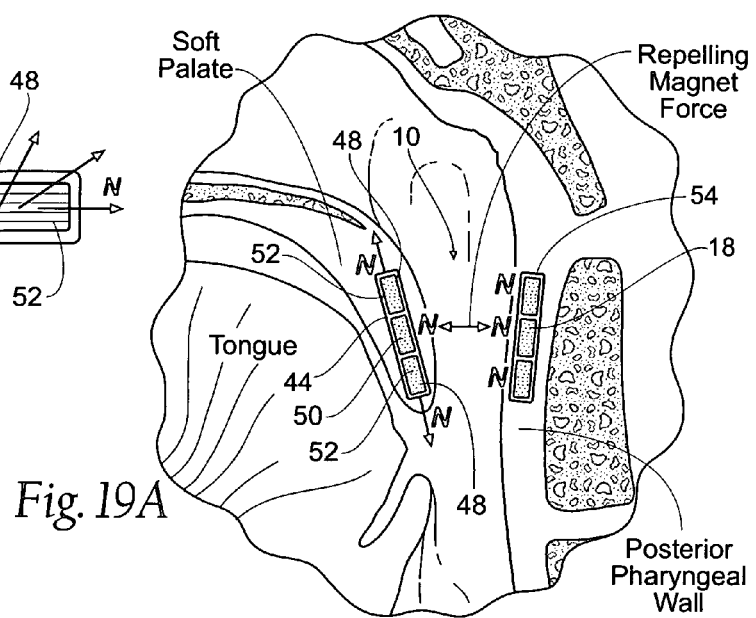
FIGS. 19A, 19B, and 19C are anatomic side section views of the implant shown in FIG. 18 implanted in a soft palate in alignment with a magnetic implant in a pharyngeal wall, showing that, as the soft palate moves, e.g., during swallowing, the repelling orientation and alignment between the magnetic implants is maintained.

FIGS. 19A/B/C show a magnetic force system 10 comprising the magnetic soft palate implant 44 shown in FIG. 18 used in association with magnetic pharyngeal wall implant 54. The poles of the magnet 50 on the magnetic soft palate implant 44 and the magnets 18 of the pharyngeal wall implant 54 are alike across the airway (N-N or S-S), thus repelling each other. As before described, a soft palate implant 44 can undergo extensive bending in the process of swallowing. Thus the magnets along the lower edge of the soft palate implant 44 are prone to come out of alignment with respect to the magnets in the pharyngeal wall implant 54. Implant 54 also keeps the edges of the implant in repulsion at various palate-to-pharyngeal wall orientations. As before described, absent the presence of a radial or variable field direction magnet 52, the lower edge magnets may try to twist to redirect themselves into an attracting position.

Figure 19B:
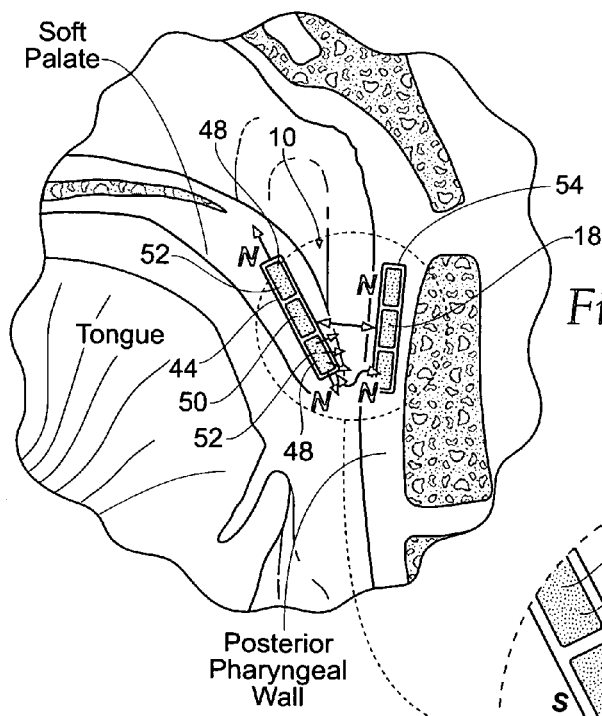
Figure 19C:
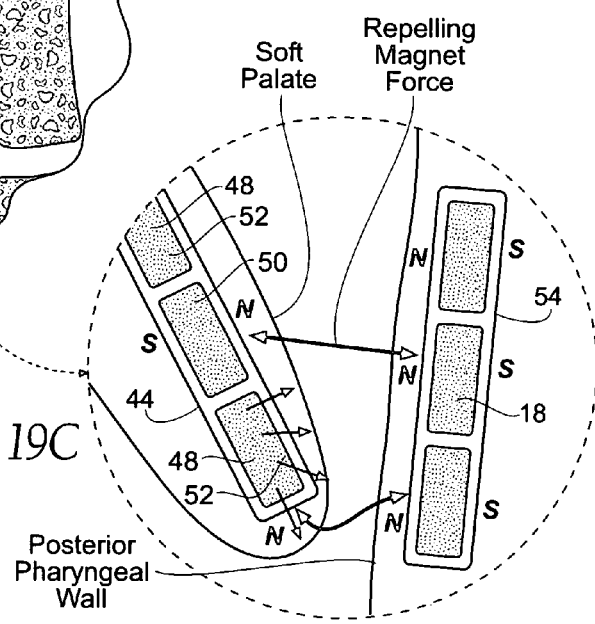

As shown in FIGS. 19B/C, the presence of the radial or variable field direction magnet 52 in the implant 44 resists this effect. As seen in FIGS. 19B/C, when the soft palate bends during the process of swallowing, the magnetic field generated by radial or variable field direction magnet 52 keeps the lower edge of magnetic soft palate implant 44 from twisting and re-directing itself into an attracting position with respect to magnetic pharyngeal wall implant 54. The magnetic field generated by radial or variable field direction magnet 52 maintains magnetic soft palate implant 30 in a repelling position even as the soft palate moves.

IV. Magnetic Structures for the Pharyngeal Wall

As previously described, the different embodiments of the magnetic force system 10 have included a magnetic structure or magnetic component 14 sized and configured to be placed on or in the pharyngeal wall in repelling magnetic alignment with the soft palate magnetic structure or magnetic component 12. Alternatively or additionally, the magnetic structure or magnetic component 14 may be sized and configured to be placed in the pharyngeal wall so as to place a torque on the soft palate magnetic component or magnetic structure 12.

Figure 20A:
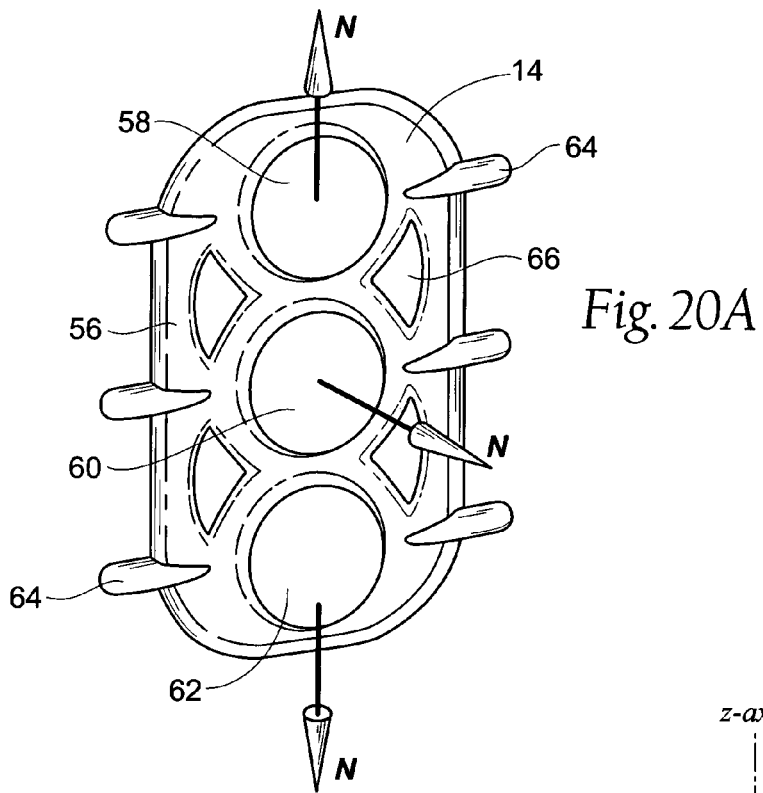
FIGS. 20A, 20B, and 20C are, respectively a perspective front view and cross-sectional views of a magnetic implant comprising permanent magnets arranged in a side-by-side relationship on a support structure sized and configured to be implanted along the midline of the posterior pharyngeal wall, across from a selected soft palate or tongue implant, having magnetic fields that are mutually angled within the implant and/or along one or more edges of the implant.

FIGS. 20A/B show a representative embodiment of a magnetic structure or magnetic component 14 sized and configured for implantation in a pharyngeal wall in association with a magnetic structure or magnetic component 12 implanted in a soft palate, or another tissue mass facing the pharyngeal wall across the airway, e.g., the tongue. The magnetic structure or magnetic component 14 comprises a support structure 56 that carries an array of magnetic components 18.

As before described, the support structure 56 can comprise a flexible or compliant material, for example, a woven, formed, or molded structure made, e.g., from a polymer or fiber or fabric or non-ferrous metallic material. The support structure 56 can be variously shaped, sized, and configured for implantation in the pharyngeal wall. The support structure 56 desirably includes features to impart stability and comfort while implanted. For example, the support structure 56 can include integrated fixation tabs 64 that extend outward from the main body of the structure 56 to engage adjacent tissue and provide enhanced fixation and stabilization. The structure 56 also desirably includes holes 66 for tissue in-growth or the placement of a tissue in-growth promoting material or bio-adhesive.

In FIGS. 20A/B, the magnetic components 18 comprise three permanent magnets 58, 60, and 62, arranged in a side-by-side relationship on the support structure 56. In this arrangement, the magnet 60 is placed in a middle region of the structure 56, and the magnets 58 and 60 are placed in opposite side regions of the structure 56. In use, as FIG. 18 shows, when implanted, the structure 56 is intended to be implanted along the midline of the posterior pharyngeal wall, across from the selected soft palate magnetic structure or magnetic component 12. As before described, the facing implant can be implanted in a tongue instead of a soft palate, depending upon type of the apneic event being treated.

Figure 21A:
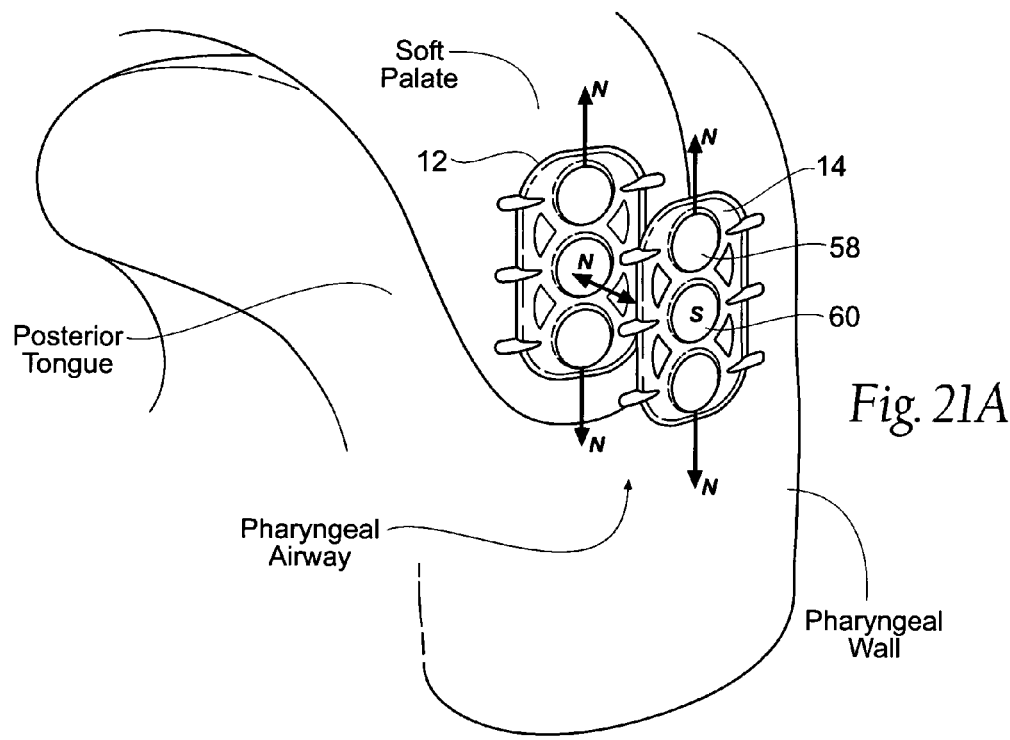
FIGS. 21A and 21B are, respectively, anatomic posterior and side section views of the implant shown in FIGS. 20A, 20B, and 20C implanted in a posterior pharyngeal wall in repelling orientation with an implant implanted in a soft palate.
Figure 21B:
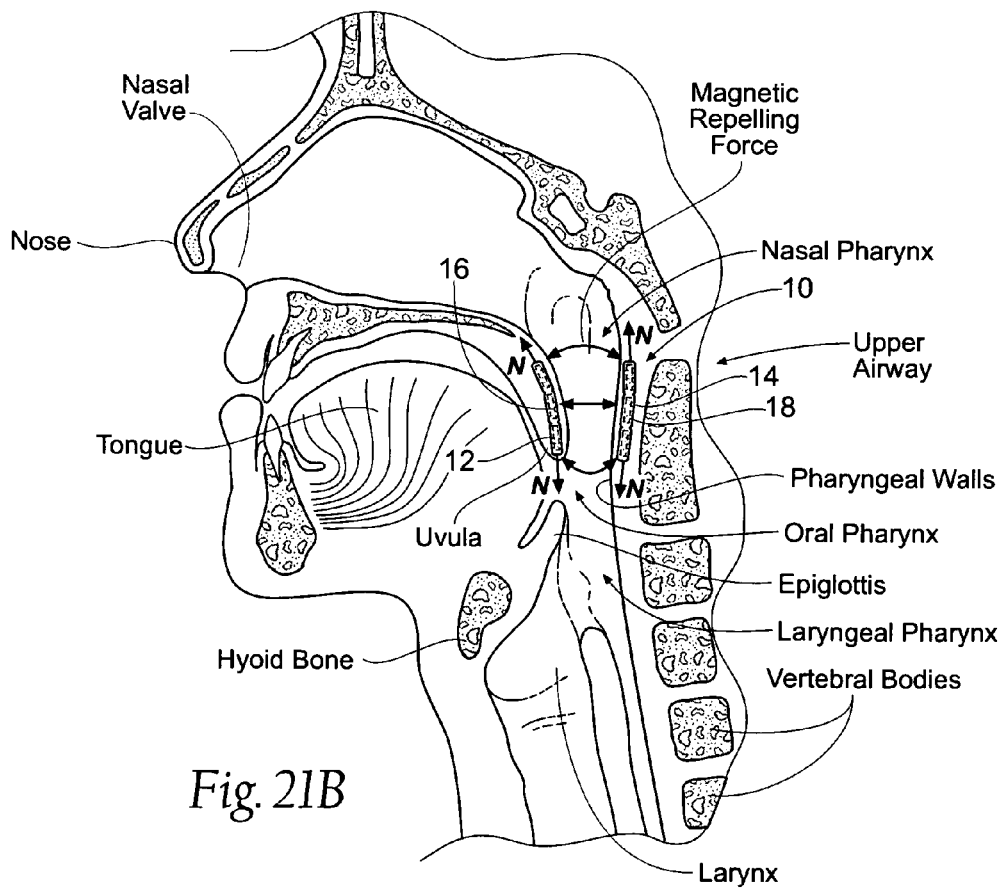

As shown in FIGS. 20A/B, the magnetic field of the N-pole of the middle magnet 60 is directed normal to the plane of the support structure 56. When implanted, the magnetic field of the N-pole is oriented in the direction of the airway. Accordingly, the magnetic field of the N-pole of the facing magnetic structure or magnetic component 12 (see FIGS. 21A and 21B) is generally aligned with the N-pole of the center magnet 60, to create the intended repelling magnetic field effect, which resists collapse of the soft palate against the pharyngeal wall, as previously described.

Figure 20B:
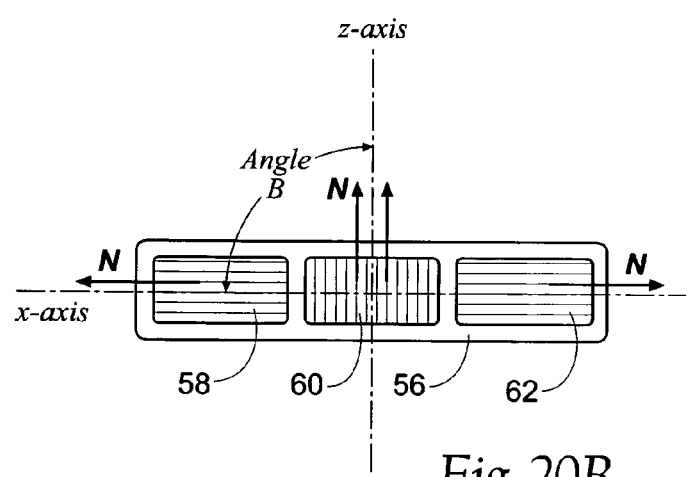
Figure 20C:
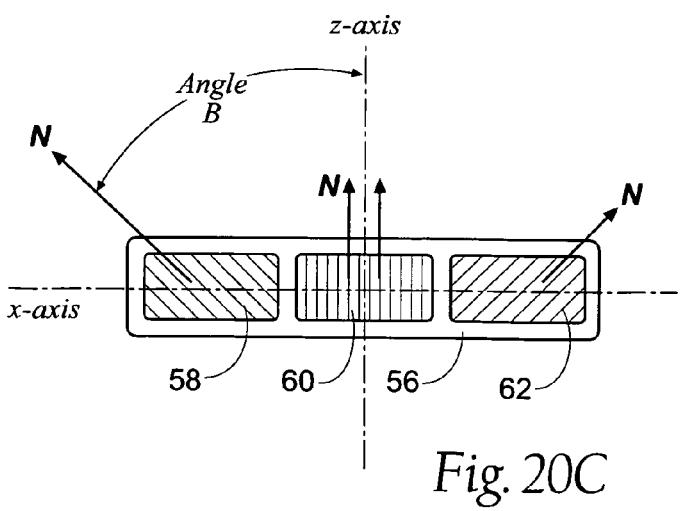

As FIGS. 20A/B show, the directions of the magnetic fields of the N-poles of the end region magnets 58 and 62 are oriented at an angle B relative to the direction of the magnetic field of the N-Pole of the center magnet 60. The magnitude of the angle B can range between about 90-degrees (see FIGS. 20A/B) and about 45-degrees (as shown in FIG. 20C). Stated differently (as FIG. 20B or 20C best show), designating the direction of the magnetic field of the N-pole of the center magnet 60 as the z-axis, and designating the end regions as being spaced with the center magnet 60 along the x-axis, the magnetic fields of the N-poles of the end region magnets 58 and 62 project an angle B in opposite directions along the x-axis.

Figure 22:
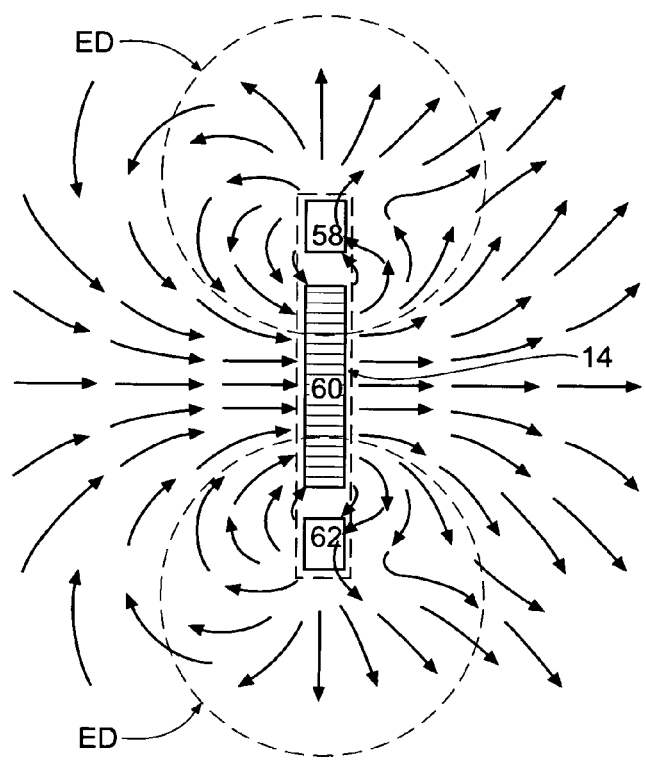
FIG. 22 shows, somewhat diagrammatically based upon finite element analysis, the flux distribution of the z-axis field component of the implant of a type shown in FIGS. 20A/B/C and 21A/B, in which the directions of the magnetic fields of the N-poles of the end region magnets are oriented at an angle B relative to the direction of the magnetic field of the N-pole of the center magnet.
Figure 23:
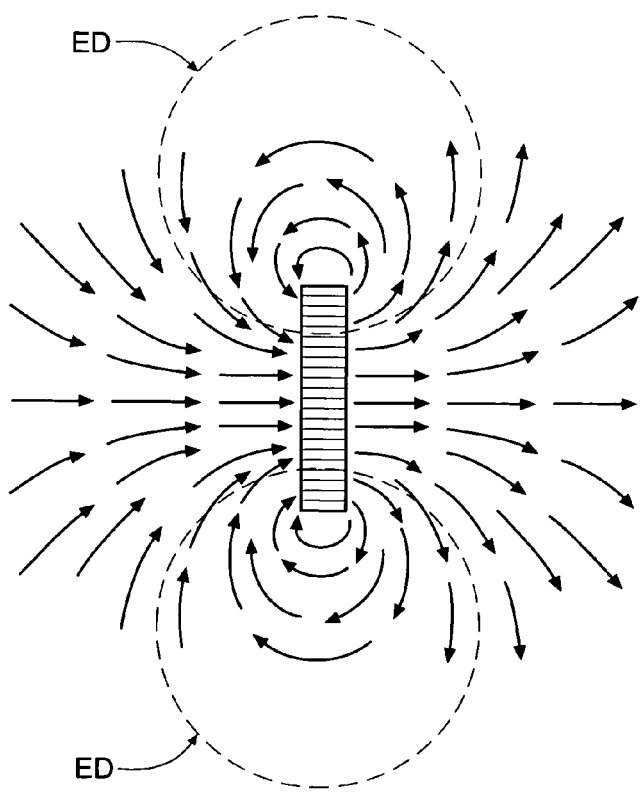
FIG. 23 shows, in comparison to FIG. 22, the flux distribution of the z-axis field component of an implant like that shown in FIGS. 20A/B/C and 21A/B, but in which the direction of the N-pole magnetic field of all magnets is parallel along the z-axis.

FIG. 22 shows, somewhat diagrammatically based upon finite element analysis, the flux distribution of the z-axis field component of the magnetic structure or magnetic component 14 shown in FIGS. 20A/B/C and 21A/B, in which the directions of the magnetic fields of the N-poles of the end region magnets 58 and 62 are oriented at an angle B relative to the direction of the magnetic field of the N-Pole of the center magnet 60. It is the z-axis field component that projects across the airway and magnetically interacts (by repelling) with the facing soft palate (or tongue) implant. FIG. 23 shows, in comparison, the flux distribution of the z-axis field component of an implant like that shown in FIGS. 20A/B/C and 21A/B, but in which the direction of the N-pole magnetic field of all magnets 58, 60, and 62 are parallel along the z-axis. It can be seen by comparing FIGS. 22 and 23, that the flux distribution of the magnetic array shown in FIGS. 20A/B/C and 21A/B more uniformly projects the repelling z-axis field component across the airway, moderating the edge discontinuities indicated by ED in FIGS. 22 and 23. Non-uniform magnetic flux distribution of the type shown in FIG. 23 can lead to misalignment of the repelling magnetic fields and lead to undesirable torque effects, as described above.

Figure 24:
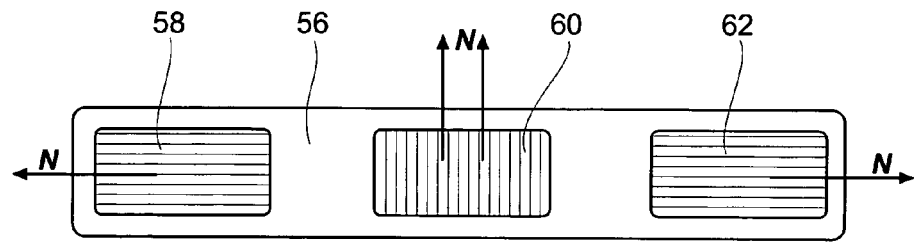
FIG. 24 is a cross-sectional view of a representative embodiment of an implant having magnetic fields that are mutually angled within the implant and/or along one or more edges of the implant.

An implant having a more uniform magnetic flux distribution as shown in FIG. 22 can be manufactured in various ways. For example, as shown in FIG. 24, permanent magnets 58, 60, and 62 can be physically mounted and affixed, after magnetization, on a carrier support structure 56.

Figure 25A:
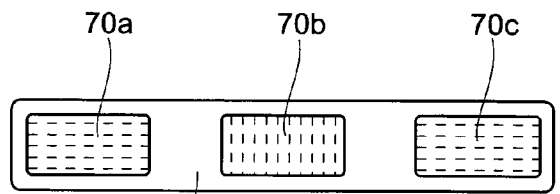
FIGS. 25A, 25B, and 25C show in diagrammatic form a representative method of manufacturing the implant shown in FIG. 24.
Figure 25B:
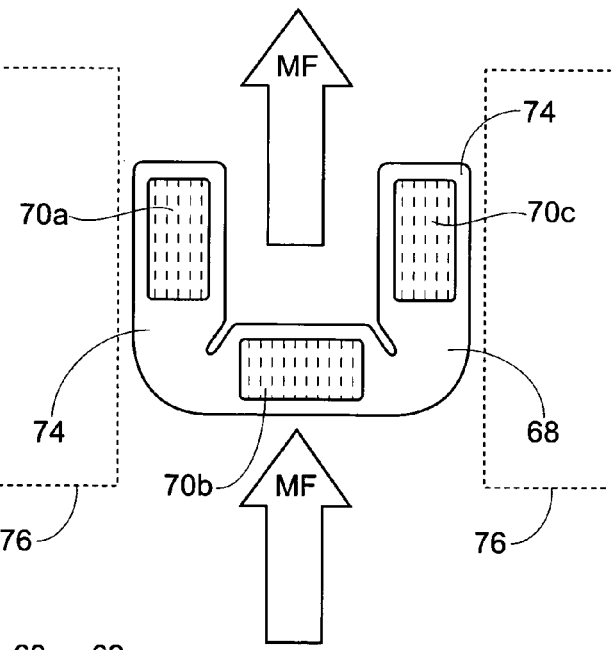
Figure 25C:
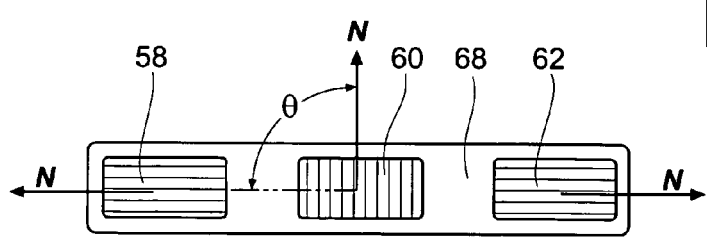

Alternatively, as FIGS. 25A, 25B, and 25C show, material 70a, 70b, and 70c that can be permanently magnetized (e.g., an alloy of Neodymium-Iron-Boron) and placed on a foldable carrier support 68, prior to undergoing magnetization, while the carrier support 68 is in a flat condition (see FIG. 25A). The grain directions of the material 70a, 70b, and 70c (indicated by dashed lines in FIG. 25A) are oriented and fixed prior to magnetization on the support carrier 68 to align with the intended direction of N-pole magnetic field following magnetization (i.e., the material 70b, after magnetization, is to become the center magnet 60, and the materials 70a and 70c are, after magnetization, to become the edge region magnets, respectively 58 and 62). The grain directions among the materials 70a, 70b, and 70c (designated by angle θ in FIG. 25C) may also be varied in alternative ways, symmetrically and/or asymmetrically. The angle θ shown in FIG. 25C can vary from 0° to 90°.

The carrier support 68 is folded along two fold lines (see FIG. 25B), with the material 70b occupying the middle 72 of the folded structure, and the materials 70a and 70c on up-folded wings 74 of the structure. The structure 68 is placed in a conventional magnetizer 76 in this folded orientation (FIG. 25B), and the field of the magnetizer applied (as shown by the arrow MF in FIG. 25B) to magnetize the materials 70a, 70b, and 70c along their grains. Removed from the magnetizer 76 and unfolded (FIG. 25C), the result provides on the support carrier 68 permanent magnets 58, 60, and 62 having magnetic fields that provide the uniform magnetic flux distribution as shown in FIG. 22.

Figure 26A:
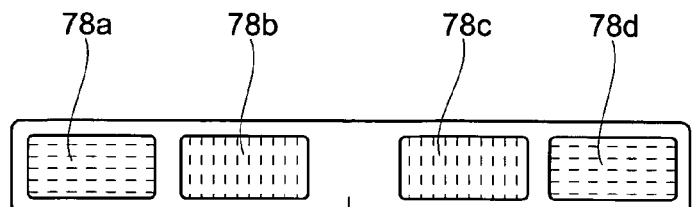
FIGS. 26A, 26B, and 26C are views of another representative embodiment of an implant having magnetic fields that are mutually angled within the implant and/or along one or more edges of the implant, including (in FIGS. 26A and 26B) a representative method of manufacturing the implant.
Figure 26B:
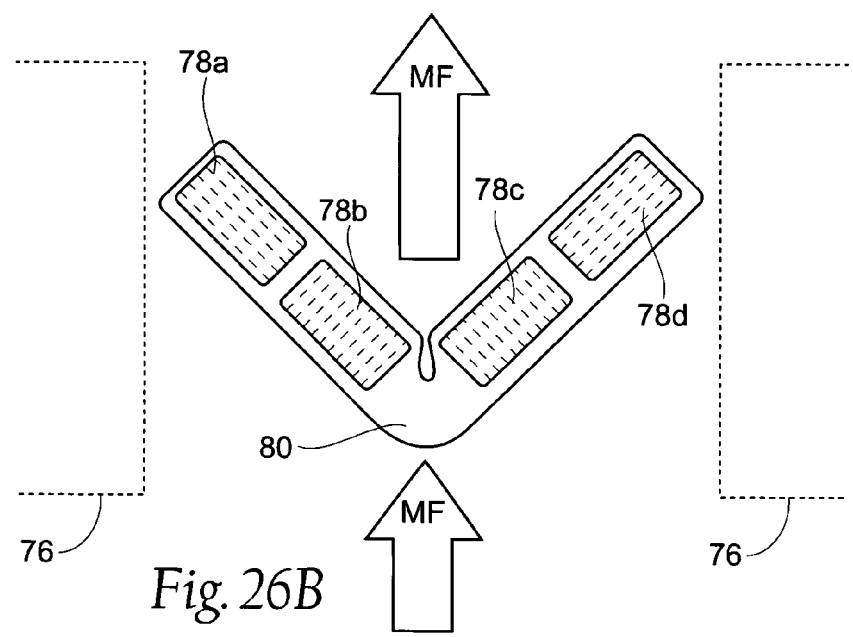
Figure 26C:
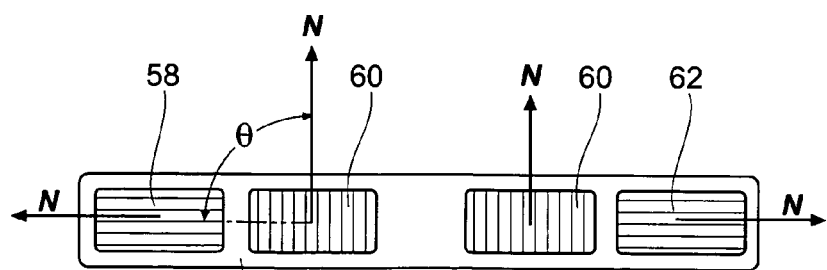

As shown in FIGS. 26A, 26B, and 26C, material 78a, 78b, 78c, and 78d that can be permanently magnetized (e.g., an alloy of Neodymium-Iron-Boron) and be placed on a foldable carrier support 80, prior to undergoing magnetization, while the carrier support 80 is in a flat condition (see FIG. 26A). The grain directions of the material 78*a*, 78*b*, 78*c*, and 70*d* (indicated by dashed lines in FIG. 26A) are oriented and fixed prior to magnetization on the support carrier 68 to align with the intended direction of N-pole magnetic field following magnetization (i.e., the materials 78*b* and 78*c*, after magnetization, are to become the center magnets 60, and the materials 78*a* and 78*d* are, after magnetization, to become the edge region magnets, respectively 58 and 62). The grain directions among the materials 78*a*, 78*b*, and 78*c* (designated by angle θ in FIG. 26C) may also be varied in alternative ways, symmetrically and/or asymmetrically. The angle θ shown in FIG. 26C can vary from 0° to 90°. The carrier support 80 is folded along one fold line in half (see FIG. 26B), with the materials 78*a* and 78*b* occupying one side of the fold line and the materials 78*c* and 78*d* occupying the other side of the fold line. The structure 80 is placed in a conventional magnetizer 76 in this folded condition (FIG. 26B), and the fold oriented to assure that the grain direction is within 45-degrees and 60-degrees of the magnetizing field (as shown by the arrow MF in FIG. 26B). The field MF magnetizes the materials 78*a*, 78*b*, 78C, and 78*d* along their grains. It has been determined that the desired orientation of magnetic fields can be achieved provided that the grain direction, when folded within the magnetizer, is aligned to within 45-degrees (60-degrees maximum) of the field of magnetization. Removed from the magnetizer 76 and unfolded (FIG. 26C), the result provides on the support carrier 80 permanent magnets 58, 60, and 62 having magnetic fields that provide the uniform magnetic flux distribution as shown in FIG. 22.

Figure 27A:
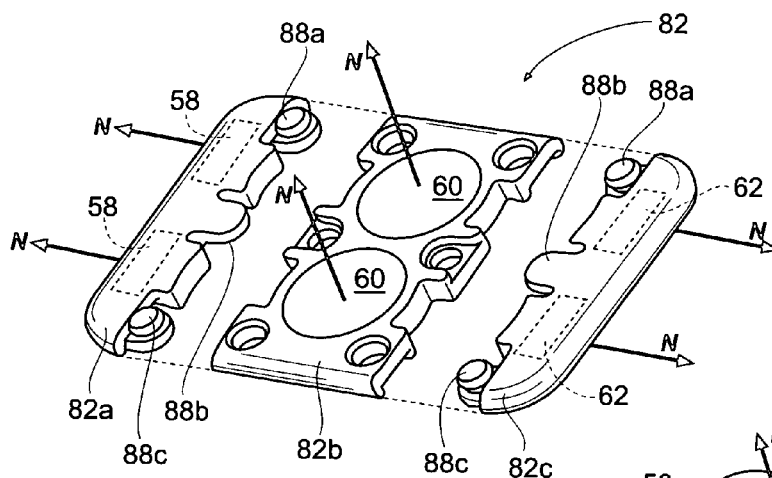
FIGS. 27A and 27B show, respectively, a perspective exploded and perspective assembled view of an implant having a three piece support carrier having magnetic fields that are mutually angled within the implant and/or along one or more edges of the implant.
Figure 27B:
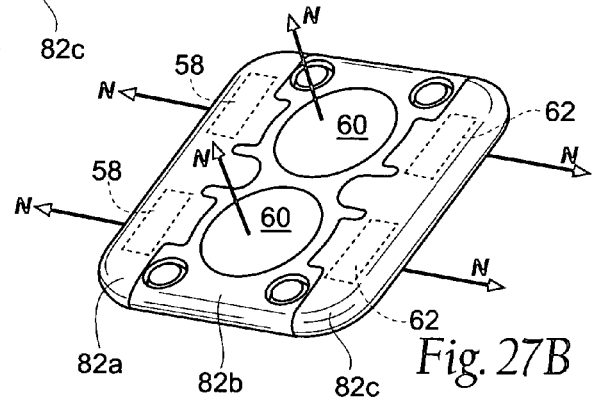

Alternatively, as FIGS. 27A and 27B show, a three piece support carrier 82 comprising components 82*a*, 82*b*, and 82*c* can be provided (see FIG. 27A). The component 82*b* carries the middle permanent magnet 60. The components 82*a* and 82*c* carry the end region magnets 58 and 62, respectively. The components 82*a*, 82*b*, and 82*c* are manufactured and magnetized as separate units, as FIG. 24A shows. At time of implantation, the components 82*a*, 82*b*, and 82*c* are assembled in situ (see FIG. 27B), to form a composite implant with the permanent magnets 58, 60, and 62 with magnetic fields that are oriented to provide the uniform magnetic flux distribution as shown in FIG. 22.

Figure 28A:
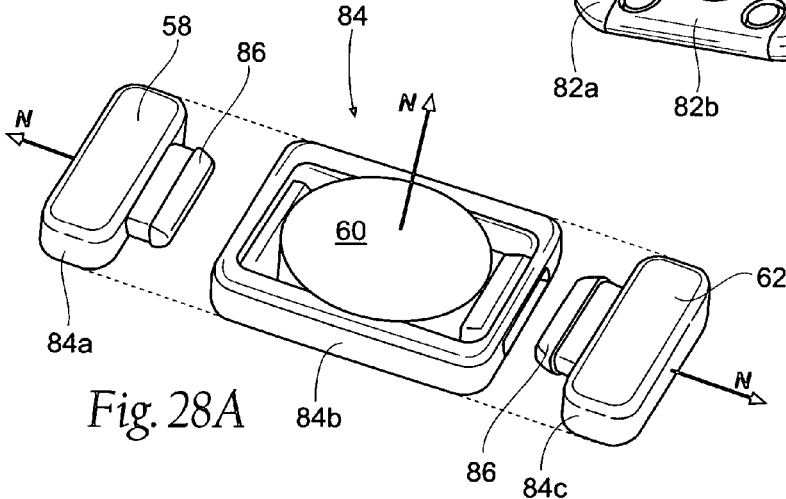
FIGS. 28A and 28B show, respectively, a perspective exploded and perspective assembled view of another embodiment of an implant having a three piece support carrier having magnetic fields that are mutually angled within the implant and/or along one or more edges of the implant.
Figure 28B:
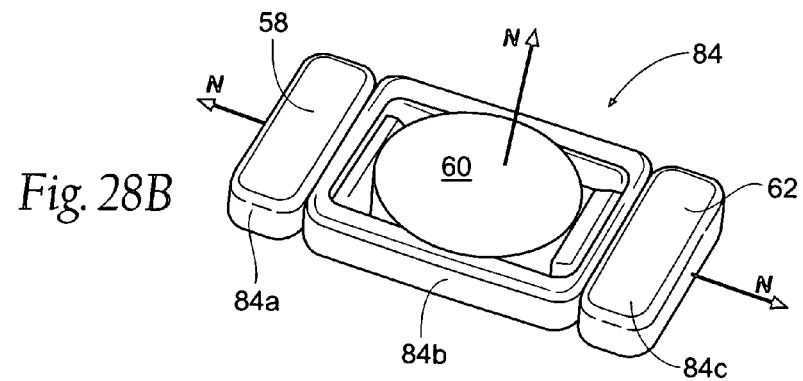

FIGS. 28A and 28B show an alternative embodiment of a three piece support carrier 84. In FIGS. 28A and 28B, the end region components 84*a* and 84*c* each couple to the middle component 84*b* by snap-fit that interlocks to the middle component 84*b* by a single end-on locking tab 86.

The size and configuration of the permanent magnets 58, 60, and 62 can differ. Each or any permanent magnet 58 or 60 or 62 can comprise a structure formed by single magnet (as FIGS. 25A/B/C and 28A/B show), or each or any permanent magnet 58 or 60 or 62 can comprise a structure formed by multiple magnets magnetized in the same direction (as FIGS. 26A/B/C and FIGS. 27A/B show).

V. Other Magnetic Structures

Other types and forms of magnetic structures can be sized and configured for positioning in or on the soft palate to achieve various desired therapeutic effects.

A. Implants that Curve in Response to a Magnetic Field

For example, FIGS. 29A to 29D show a magnetic component 100 that can be sized and configured for implantation in the soft palate. The soft palate implant 100 comprises at least three un-magnetized but polarized neodymium magnets 102 carried by a flexible structure 104. The flexible structure 104 can comprise a flexible or compliant material, for example, a woven, formed, or molded structure made, e.g., from a polymer or fiber or fabric or non-ferrous metallic material.

Figure 29A:
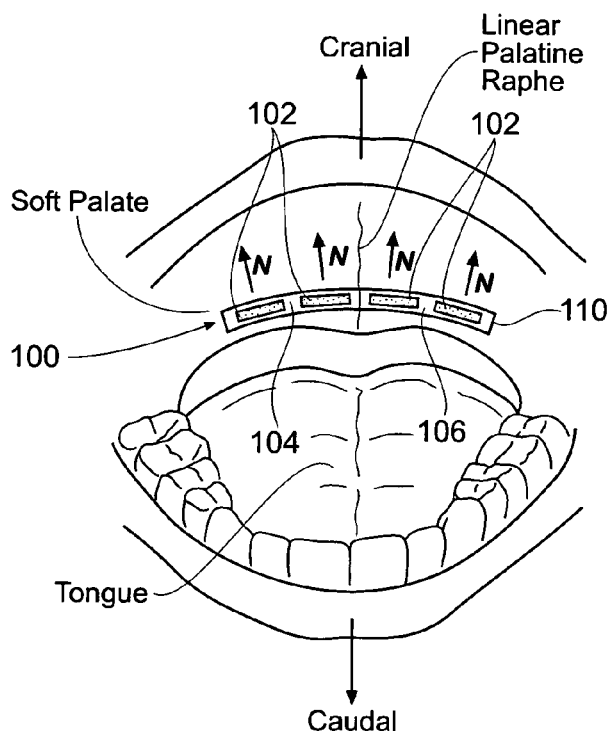
FIGS. 29A to 29D show anterior and posterior anatomic views of a magnetic component sized and configured for implantation in the soft palate and that bends within the soft tissue in response to an external magnetic force applied from within the oral cavity, FIGS. 29A and 29B showing the implant before bending, and FIGS. 29C and 29D showing the implant after bending.
Figure 29B:
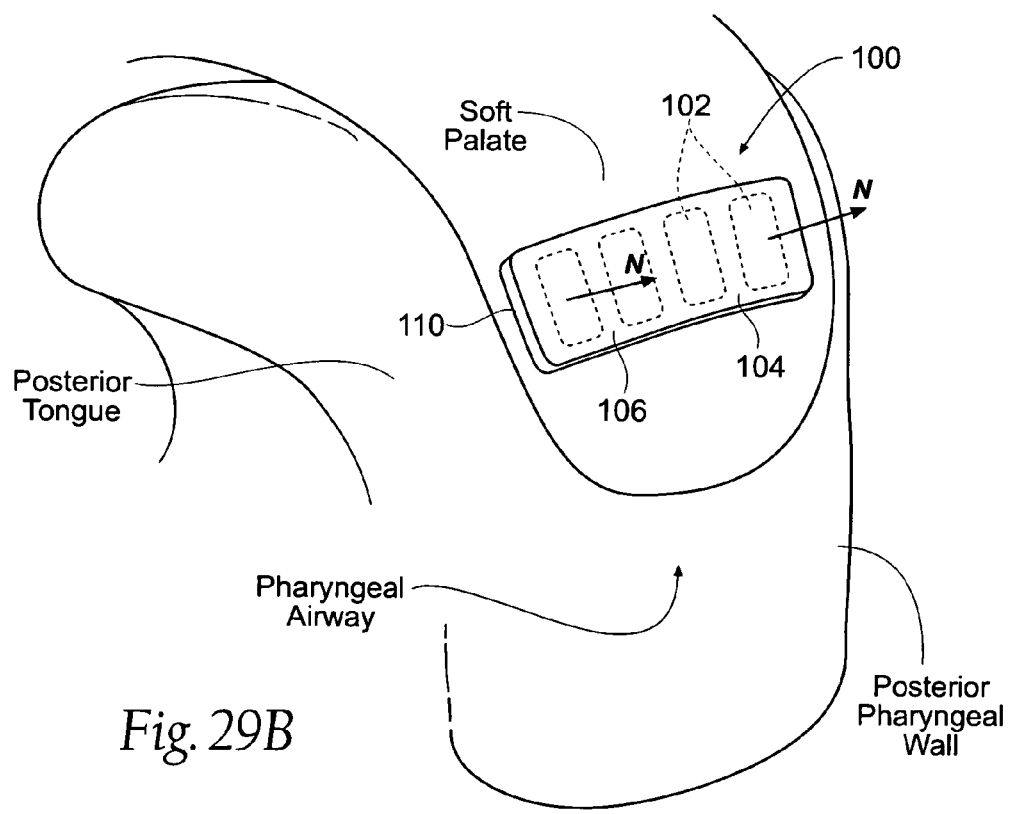

As FIGS. 29A and 29B show, the soft palate implant 100 is sized and configured to be implanted in the soft palate, perpendicular to the orientation of the raphé (which is shown in FIG. 2). The magnets 102 are polarized along a common N-pole oriented along a surface 106 of the flexible structure 104. When implanted, the surface 106 is position in the soft palate to face a cranial (superior) direction. In this arrangement, the opposite surface 110 of the component 104, facing a caudal (inferior) direction, presents a S-pole. Of course, it should be appreciated that the polarity orientation of the component 104, when implanted, can be reversed.

Figure 29C:
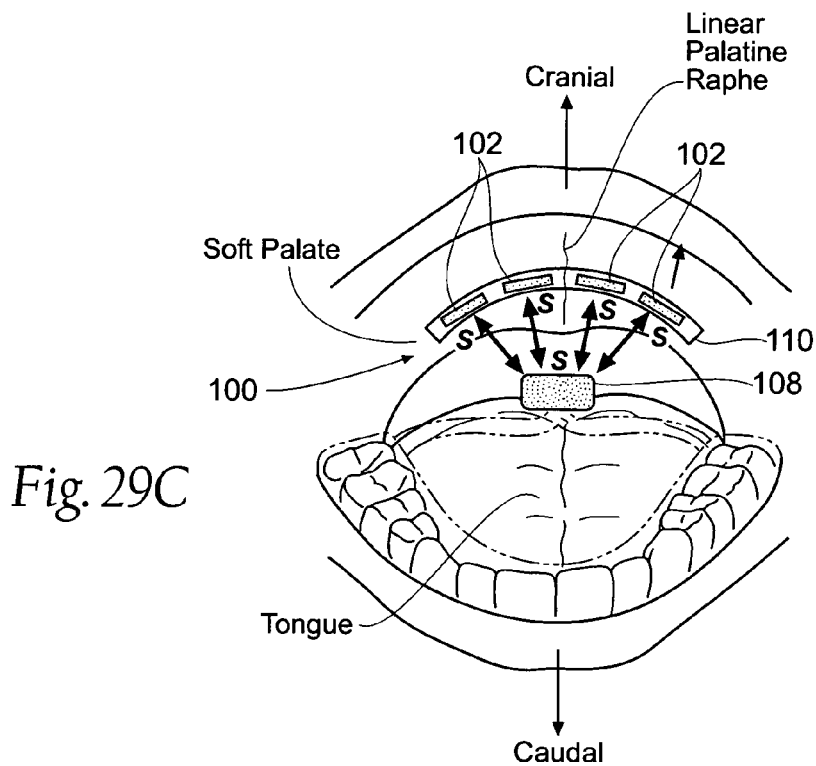
Figure 29D:
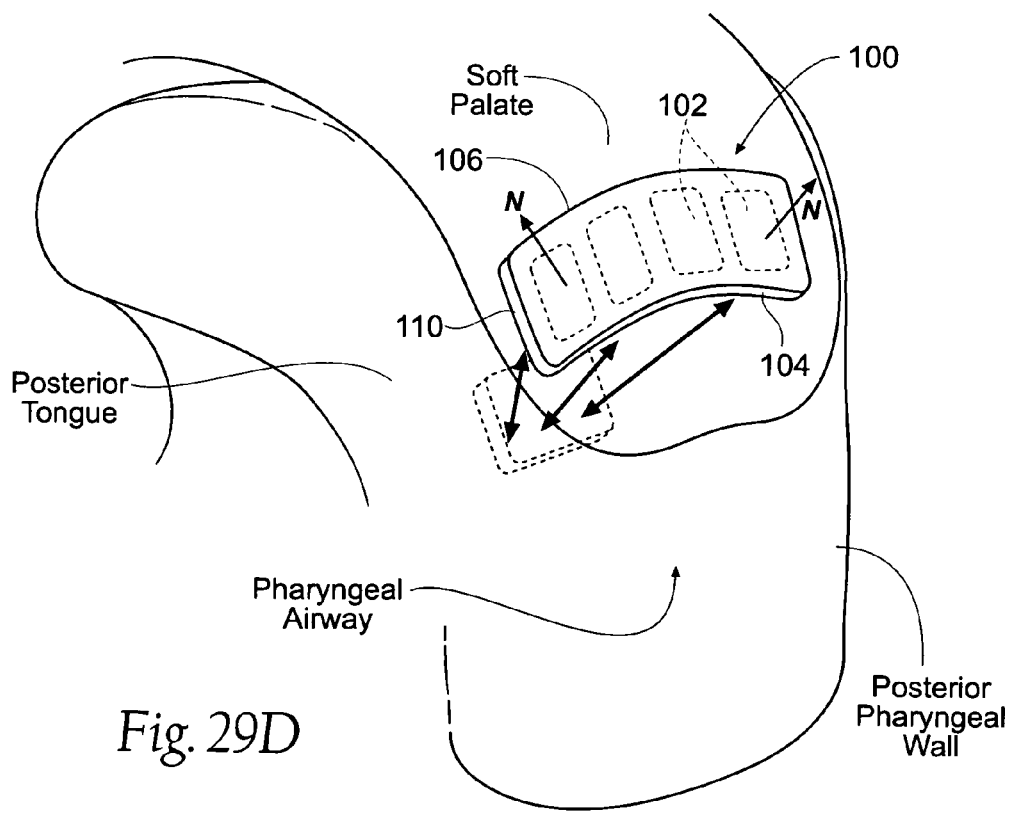

As FIGS. 29C and 29D show, the soft palate component 104, in use after implantation, magnetically interacts with a source 108 of magnetic force. The source 108 may comprise an external device, such as, but not limited to, an oral appliance placed into the oral cavity in alignment with the caudal surface 110 of the component 104 within the soft palate. Alternatively, the source 108 may comprise another magnetic implant, located in a nearby, but inferior, airway structure, to be in alignment with the caudal surface 110 of the soft palate component 104.

The source 108 projects a magnetic field toward the caudal surface 110 of the soft palate component 104. The magnetic field has a polarity that is the same as the polarity of the field projected by the caudal surface 110 of the soft palate component 104. In the illustrated embodiment, where the polarity of the caudal surface 110 is a S-pole, the polarity of the source 108 is likewise a S-pole. A repelling magnetic field is thereby generated.

The polarized neodymium magnets 102 are repelled along the caudal surface 110 of the soft palate component 104. The soft palate component 104 curves, conforming to the natural curved anatomy of the dome of the soft palate. In response to the applied repelling magnetic force field, the soft palate component 104 reinforces the natural domed curvature of the soft palate, buttressing it against sagging and collapse.

The features of the component 104 can be applied in any tissue region that is prone to sagging or collapse.

B Other Implants

Figure 30A:
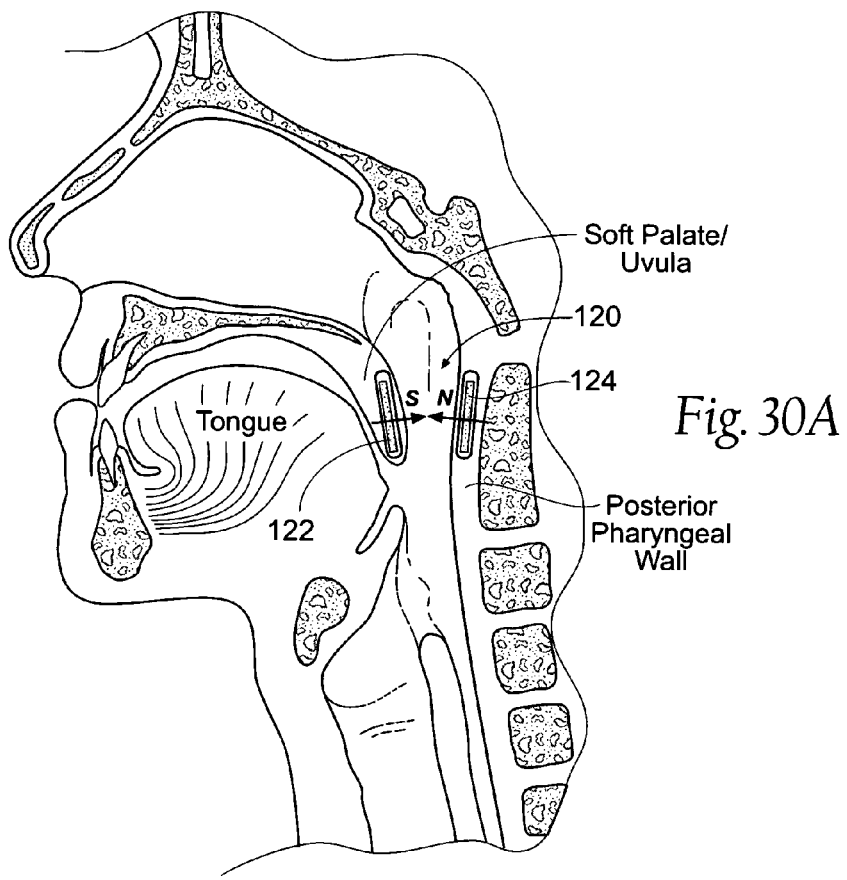
FIGS. 30A to 30F show anatomical views of a human airway and a magnetic force system installed in the airway comprising two magnetic components, one in a soft palate and the other in a pharyngeal wall, the soft palate implant including a flexible arm that accommodates concurrent attracting and repelling interaction to form an open air pocket and to give enough curvature to the soft palate as to keep the pharyngeal airway patent and prevent apneic events.

FIG. 30A shows an anatomical side view of a human airway and a magnetic force system 120 installed in the airway comprising two magnetic components 122 and 124.

Figure 30B:
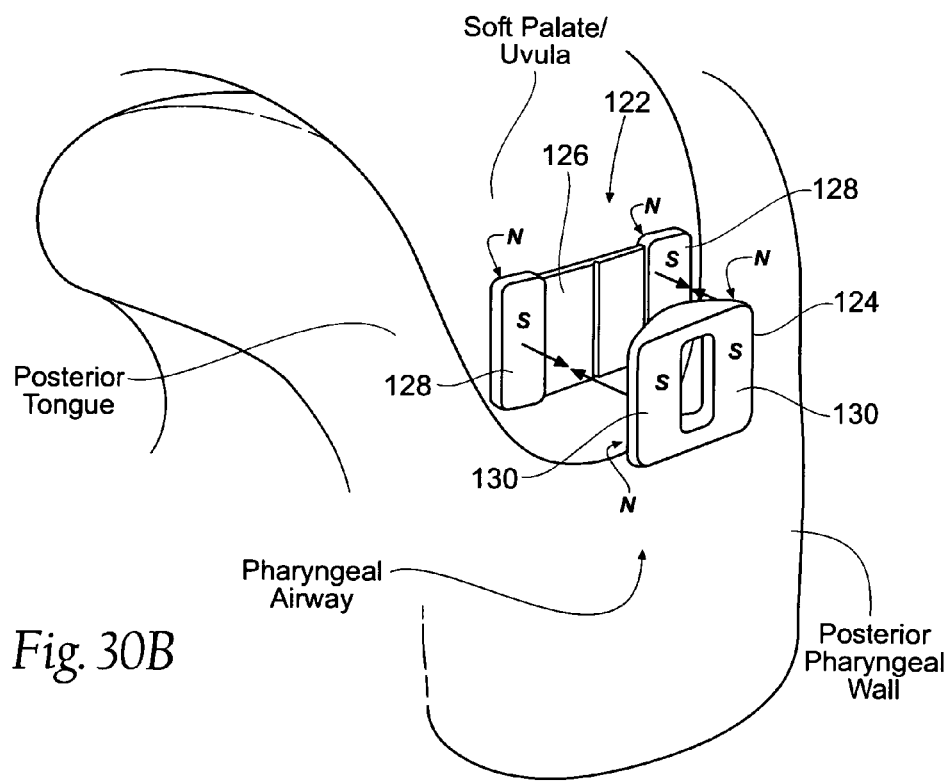
Figure 30C:
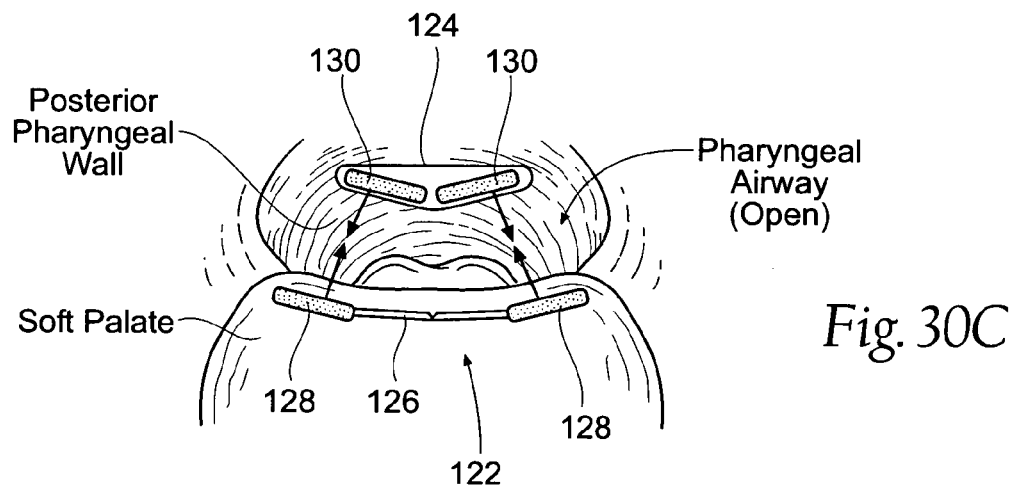

Magnetic component 122 comprises a magnetic soft palate implant. As seen in FIGS. 30B and 30C, soft palate implant 122 comprises a flexible arm 126 and magnets 128 attached to each end of the flexible arm 126. The two magnets 128 attached to the flexible arm are of like polarity. In the illustrated embodiment, the magnets 128 have a S-pole facing the airway.

Magnetic component 124 comprises a pharyngeal wall implant. As shown in FIGS. 30B and 30C, the pharyngeal wall implant 124 comprises magnets 130 that, when implanted, are generally aligned with the magnets 128 of the soft palate implant 122. The magnets 130 are polarized such that they have a polarity, when implanted, facing the airway that is opposite to the polarity of aligned the soft palate implant 122. In the illustrated embodiment, the polarity of the magnets 130 is a N-pole. The N-poles are capable of attracting the S-poles of the magnets 128 carried on the flexible arm 126 of the soft palate implant 122.

The strength of the magnets 128 and 130 is titrated such that, while the individual is awake, the soft palate muscles keep the magnetic soft palate implant 122 sufficiently spaced away from the pharyngeal wall implant 124, so that there is no magnetic interaction between them. This is shown in FIGS. 30A, B, and C.

Figure 30D:
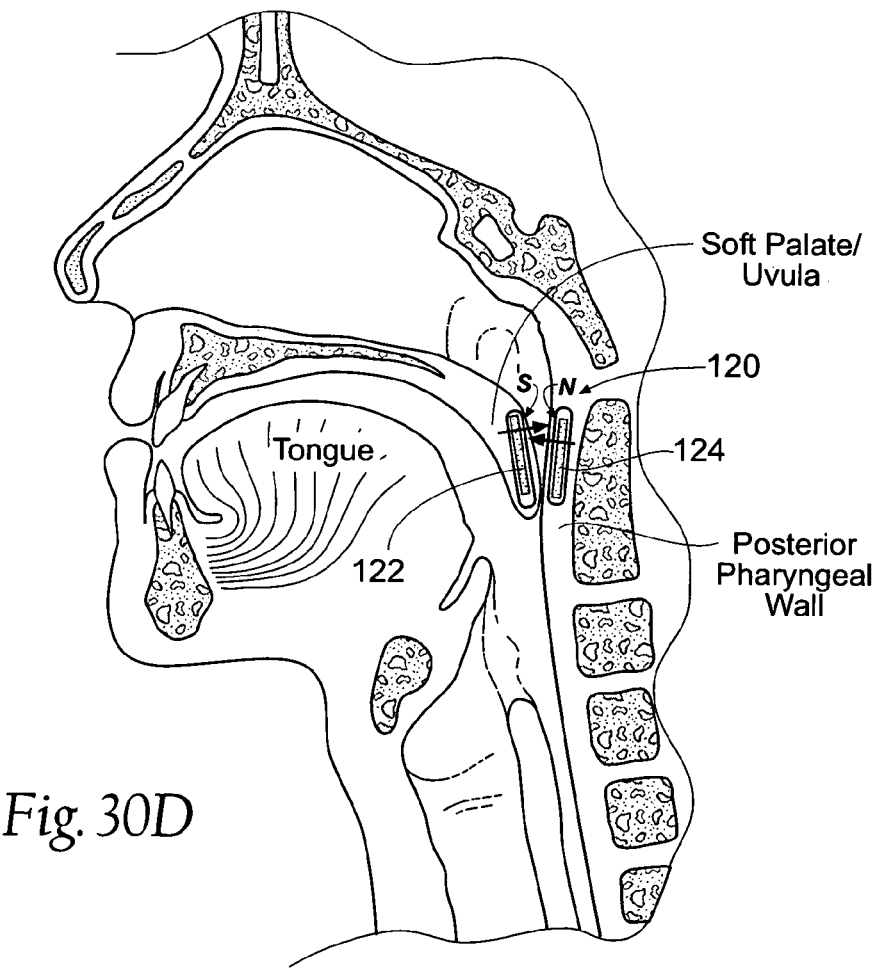

However, as shown in FIGS. 30D, E, and F, when the patient is asleep or in a situation when the soft palate otherwise collapses, the magnetic soft palate implant 122 is brought into close proximity to the pharyngeal wall implant 124. In close proximity, the soft palate implant 122 and the pharyngeal wall implant 124 magnetically interact. The magnets 128 of the soft palate implant 122 interact across the airway by attraction to the unlike poles of the magnets 130 of the pharyngeal wall implant 124. While attracted to the pharyngeal wall implant 124, the two magnets 128 on the flexible arm 126 of the soft palate implant 122 (which being aligned with like S-poles) interact by repelling each other.

Figure 30E:
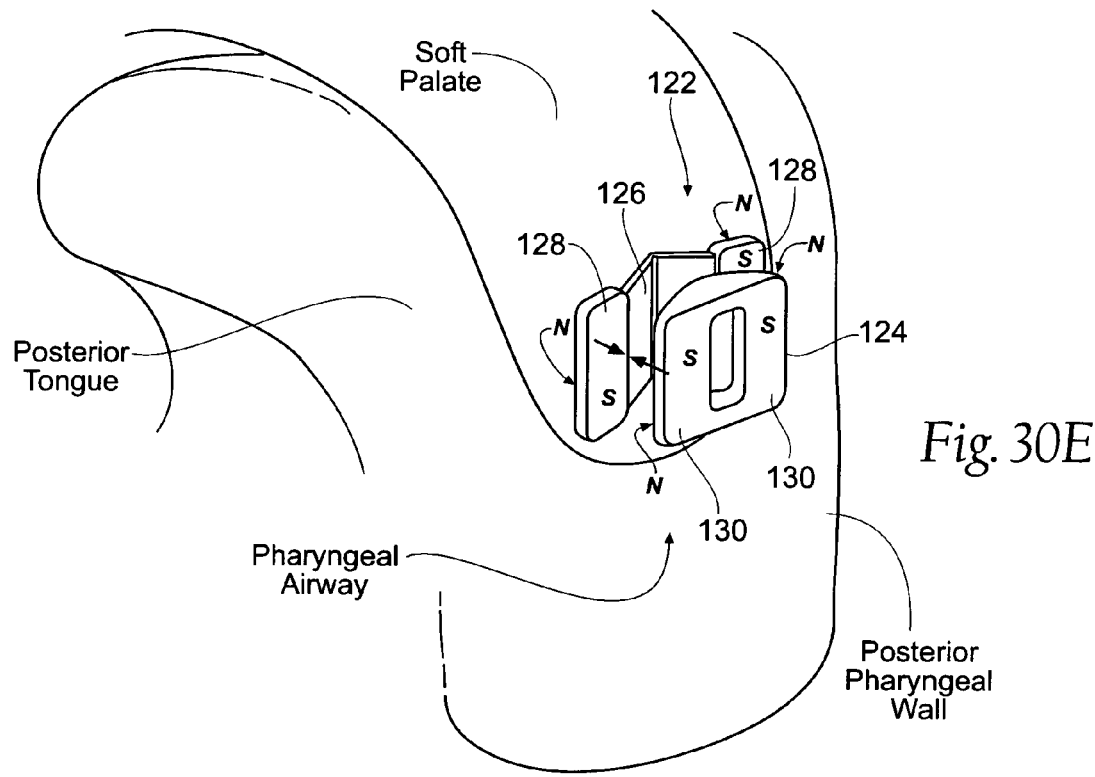
Figure 30F:
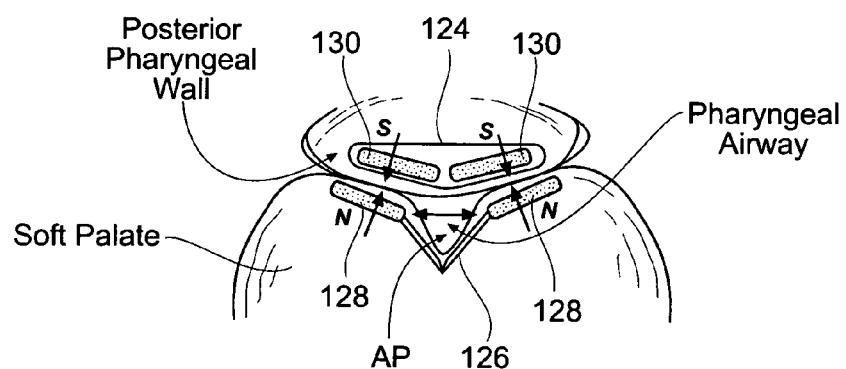

As FIG. 30E best shows, the concurrent attracting and repelling interaction among the magnets 128 and 130 allows the flexible arm 126 of the soft palate implant 122 to form an open air pocket and to give enough curvature to the soft palate as to keep the pharyngeal airway patent and prevent apneic events.

Figure 31A:
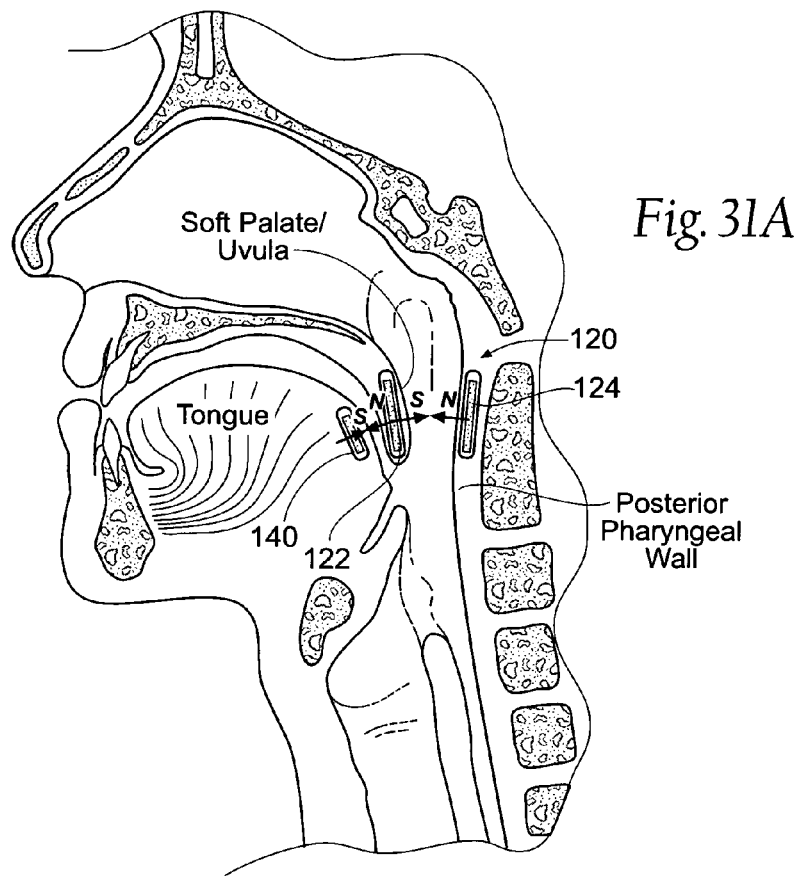
FIGS. 31A to 31F show anatomical views of a human airway and a magnetic force system of the type shown in FIGS. 30A to 30F, augmented by the inclusion of another implant in the tongue.
Figure 31B:
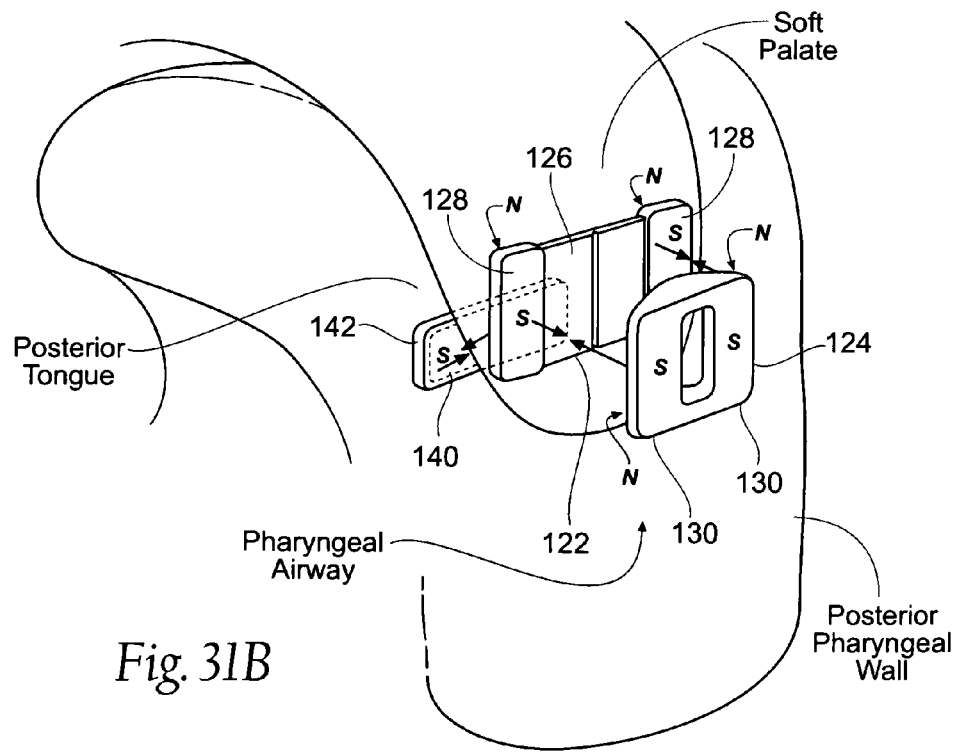

The magnetic force system 120 shown in FIGS. 30A to 30F can be augmented by the inclusion of an implant 140 in the tongue, as FIGS. 31A and 31B show. The tongue implant 140 includes magnets 142 that, when implanted, are generally aligned with the magnets 128 of the soft palate implant 122. The magnets 140, like the magnets 130 of the pharyngeal wall implant 124, are polarized such that they have a polarity, when implanted, facing the airway that is opposite to the polarity of the aligned soft palate implant 122. In the illustrated embodiment, the polarity of the magnets 130 is an N-pole. The aligned N-S poles are capable of attracting the magnets 128 carried on the flexible arm 126 of the soft palate implant 122. The magnets 128 carried on the flexible arm 126 of the soft palate implant 122 are therefore concurrently subject to attraction by either or both of the magnets 130 on the pharyngeal wall 124 or the magnets 142 on the tongue implant 140, depending upon their relative proximity.

Figure 31C:
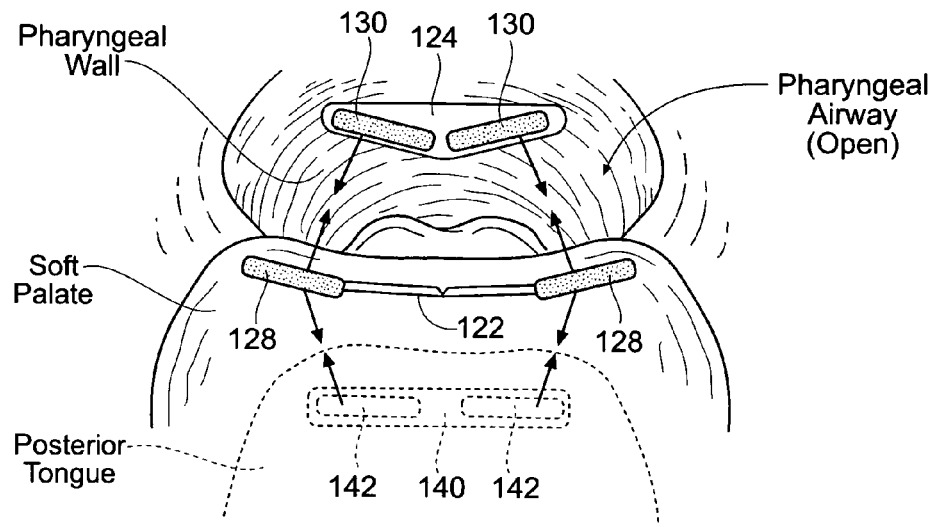

The strength of the magnets 128, 130, and 142 is titrated such that, while the individual is awake, the soft palate muscles keep the magnetic soft palate implant 122 sufficiently spaced away from the pharyngeal wall implant 124 and the tongue implant 140, so that there is no magnetic interaction among them. This is shown in FIGS. 31A, 31B, and 31C.

Figure 31D:
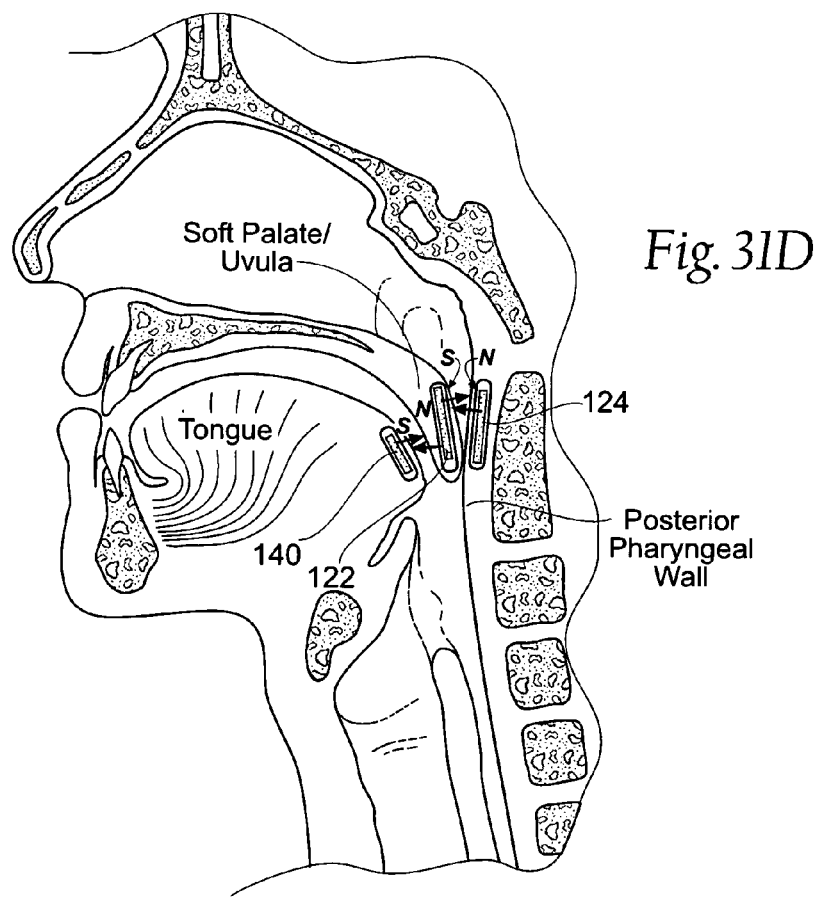
Figure 31E:
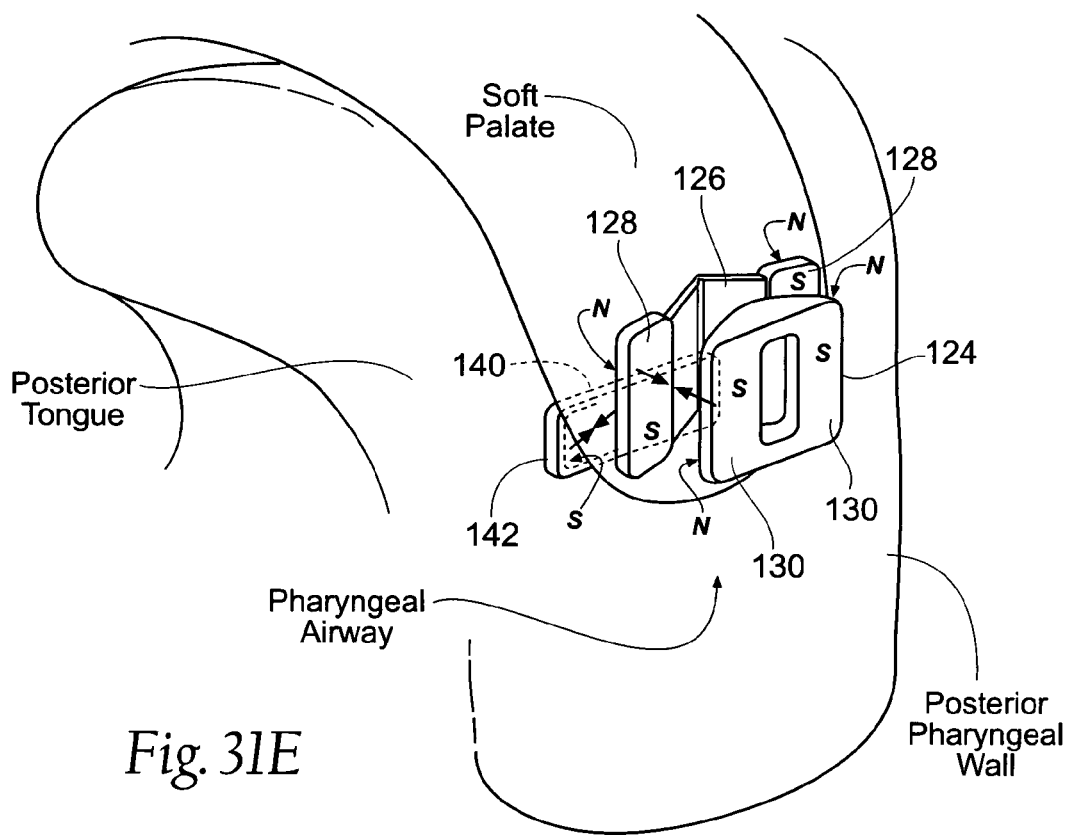
Figure 31F:
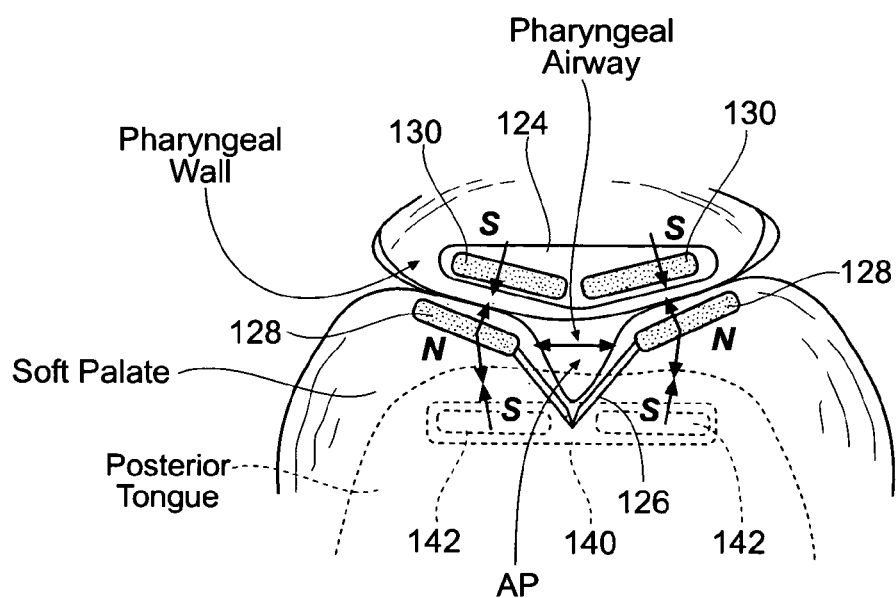

However, as shown in FIGS. 31D, 31E, and 31F when the patient is asleep or in a situation when the soft palate otherwise collapses, the magnetic soft palate implant 122 is brought into close proximity to either the pharyngeal wall implant 124 or the tongue implant 140, or both. In close proximity, the soft palate implant 122 and the pharyngeal wall implant 124 and/or the tongue implant 140 magnetically interact. The magnets 128 of the soft palate implant 122 interact across the airway by attraction to the unlike poles of the magnets 130 of the pharyngeal wall implant 124 and/or the tongue implant 140. While attracted to the pharyngeal wall implant 124 and/or the tongue implant 140, the two magnets 128 on the flexible arm 126 of the soft palate implant 122 (which being aligned with like poles) interact by repelling each other.

As FIG. 31F best shows, the concurrent attracting and repelling interaction among the magnets 128, 130, and 142 allows the flexible arm 126 of the soft palate implant 122 to form an open air pocket and to give enough curvature to the soft palate as to keep the pharyngeal airway patent and prevent apneic events.

C. Single Component Magnetic Soft Palate Implant Systems

Figure 32A:
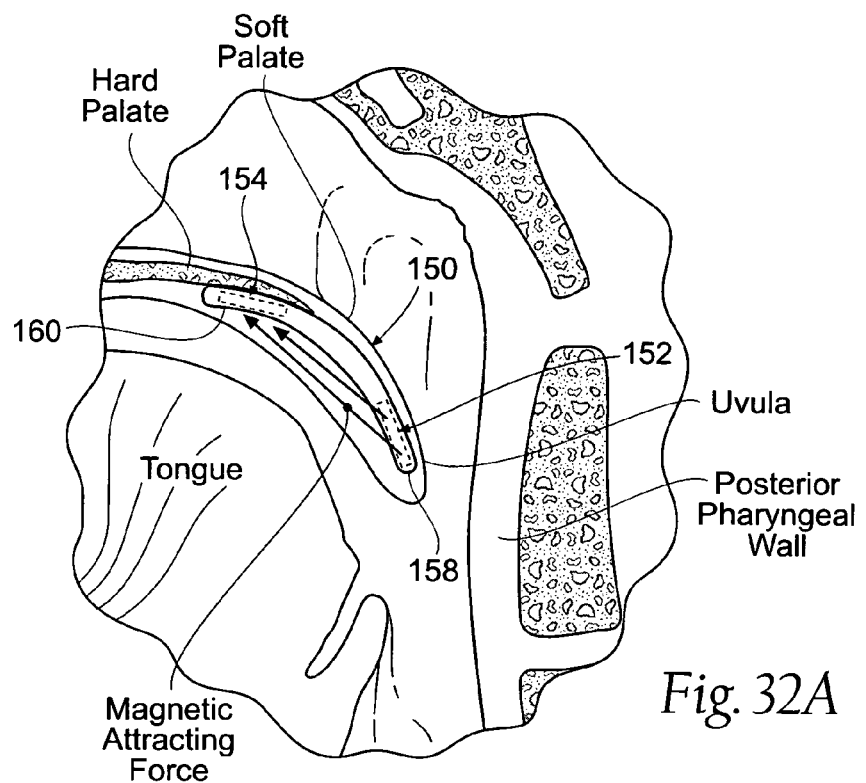
FIG. 32A is an anatomic side section view of an alternative embodiment of a magnetic implant that is sized and configured for implantation in a region of the soft palate, the implant having one end that can be placed or anchored to the bony part of the hard palate and the other end implanted in or attached to the soft palate, attracting interaction between magnets at the opposite ends urges the soft palate toward the hard palate, away from the pharyngeal wall, thus keeping the airway open.

FIG. 32A shows an alternative embodiment of a magnetic component 150 that is sized and configured for implantation in a region of the palate. The magnetic component 150 comprises a magnetic array 152, implanted so that one end 154 is anchored to the bony part of the hard palate or the connective tissue between the hard palate and the soft palate using either or a combination of bone screws or cements. Alternatively the attachment to the hard palate could also take place by creating an implant pocket without actual attachment to the bony part. The other end 156 of magnetic array 152 is implanted in or attached to the soft palate. Because this is a single component implant, the apneic patient will undergo less surgery and thus conceivably less trauma upon implantation.

Magnetic array 152 comprises at least two magnets 158 and 160. The array is designed so at least one of the magnets 158 at the soft palate end 156 is attracted to the other magnet(s) 160 at the hard palate end 154. The set-up causes a torque-like effect with the magnet at the hard palate end 154 acting as the moment arm lever point.

As FIG. 32A shows, the attracting interaction between the at least two magnets 158 and 160 urges the soft palate toward the hard palate, away from the pharyngeal wall, thus keeping the airway open. An implant of a type shown in FIG. 32A can be used alone, or in combination with a repelling system comprising interaction with magnets in the pharyngeal wall.

Figure 32B:
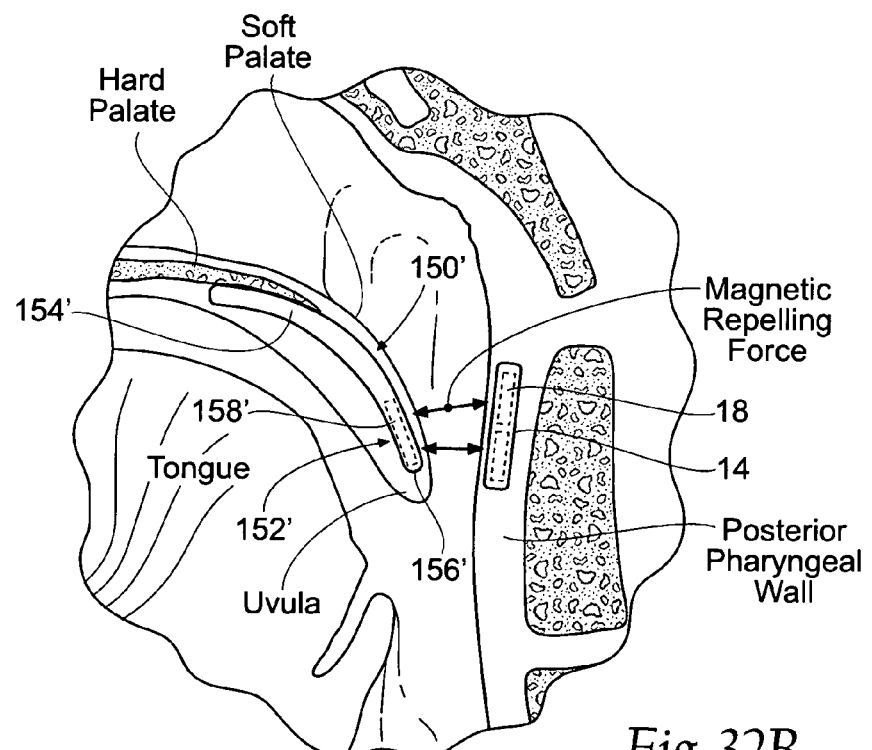
FIG. 32B is an anatomic side section view of another alternative embodiment of a magnetic implant that is sized and configured for implantation in a region of the soft palate, the implant having one end anchored to the bony part of the hard palate and the other end implanted in or attached to the soft palate with magnetic material placed only in the soft palate area; the repelling interaction between the palate implant and a pharyngeal wall implant maintains the airway open.

FIG. 32B is an anatomic side section view of an alternative embodiment of a magnetic implant that is sized and configured for implantation in a region of the palate, the implant having one end anchored to the bony part of the hard palate and the other end implanted in or attached to the soft palate with magnetic material placed only in the soft palate area.

FIG. 32B shows the alternative embodiment of a magnetic component 150' that is sized and configured for implantation in a region of the palate. The magnetic component 150' comprises a magnetic array 152'. One end 154' of the component 150' is anchored to the bony part of the hard palate or the connective tissue between the hard palate and the soft palate, using either or a combination of bone screws or cements may be used. Alternatively the attachment to the hard palate could also take place by creating an implant pocket without actual attachment to the bony part. In this embodiment, the end 154' does not contain any magnetic materials. The other end 156' of magnetic component 150' is implanted in or attached to the soft palate. It is this end 156' that contains the magnetic array 152'.

Magnetic array 152' comprises at least one magnet 158'. The array is designed so at least one of the magnets 158' at the soft palate end 156' interacts by repelling magnetic the at least one magnetic material 18 in magnetic component or magnetic structure 14 implanted across the airway in the posterior pharyngeal wall. The repelling interaction between the magnet(s) on the palate implant and a pharyngeal wall implant maintains the airway open.

Figure 34A:
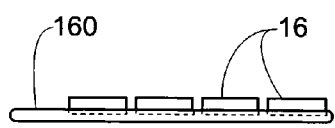
FIGS. 34A and 34B are side views of an alternative embodiment of an implant system sized and configured for implantation in a region of the soft palate, the implant having one end that can be placed or anchored to the bony part of the hard palate and the other end implanted in or attached to the soft palate, where the magnetic materials are unmagnetized and magnetized, respectively.
Figure 34B:
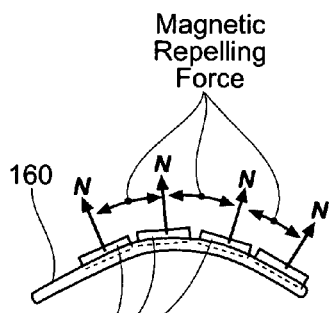
Figure 34C:
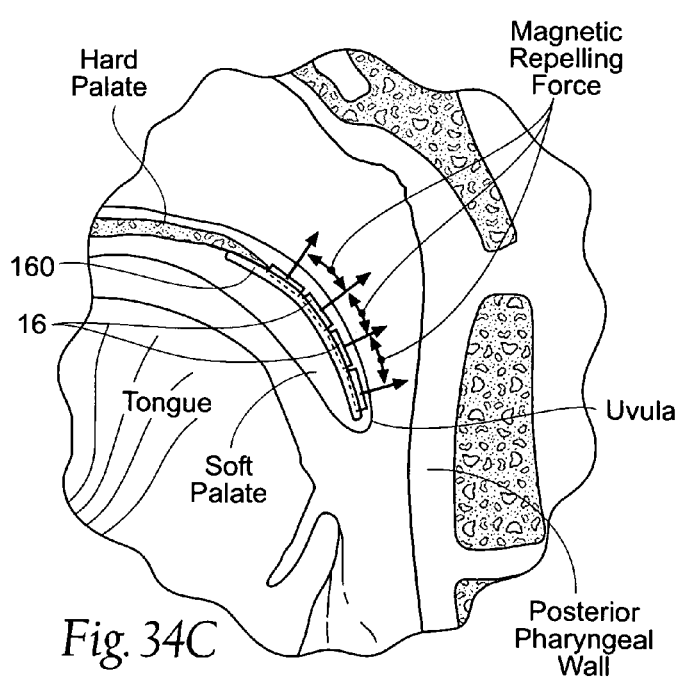
FIG. 34C is an anatomical side view of the implant system shown in FIG. 34B, showing a repelling interaction among the magnetized magnetic materials that maintains the airway open.

FIGS. 34A/B/C show another single component magnetic soft palate system. FIG. 34A shows an array comprising at least 3 initially un-magnetized magnetic materials 16 partially embedded (before being magnetized) on one side in a flexible elongated carrier 160. FIG. 34B shows the array after the at least 3 magnetic materials 16 have become magnetized in the same magnetic field direction. As can best be seen in FIG. 34B, once magnetized in the same magnetic field direction, the at least 3 magnetic materials 16 start to repel each other on the sides that are not embedded in the carrier structure 160. When implanted in the soft palate (see FIG. 34C) so that the longitudinal axis of the carrier 160 runs parallel to the midline of the palate, the repelling interaction among the magnetized magnetic materials 16 prevents the soft palate from collapsing against the pharyngeal wall, thus maintaining the patency of the airway.

VI. Force Required to Maintain a Patent Airway

Figure 33:
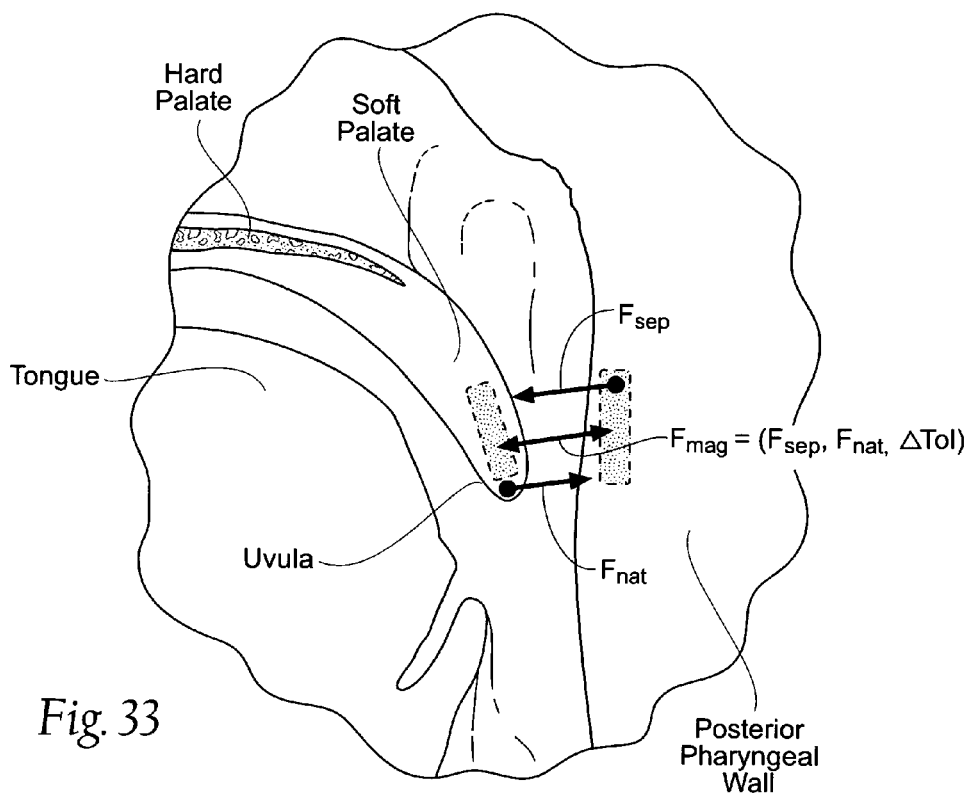
FIG. 33 is an anatomic side section view of the soft palate and pharyngeal wall, showing the resolution of forces F-sep and F-nat to provide an optimal therapeutic force F-mag that, at night, resists collapse of the soft palate and uvula against the pharyngeal wall during sleep, yet does not affect speech, swallowing or drinking during normal activities awake or asleep.

As just described, and as FIG. 33 shows in a diagrammatic way, for a given individual, a magnitude can be assigned to a force required to separate soft palate tissue from the posterior pharyngeal wall, to thereby resist the collapse of an airway during an apneic episode. This force, designated F-sep in FIG. 33, can be obtained by physical measurement of a given individual, or it can based upon measurements taken during a cadaver study, or it can be selected empirically based upon general anatomic considerations for a population of individuals, or a combination of these and other considerations.

For a given individual, a magnitude can also be assigned to a counterbalancing force (designated F-nat in FIG. 33), which represents the force exerted by natural muscular activity upon the soft palate, to enable swallowing or speech during normal airway function. The force F-nat can be also obtained by physical measurement of a given individual, or it can be selected empirically based upon general anatomic considerations for a population of individuals, or a combination of these and other considerations.

As shown in FIG. 33, the magnetic force (F-mag) that a system 10 develops can be expressed as a function of F-sep and F-nat, or F-mag=f(F-sep, F-nat). The magnetic force can comprise a repelling force (i.e., a force in essentially an anterior-posterior direction between the soft palate and posterior pharyngeal wall), and/or a torquing force (i.e., a force or moment of a force that tends to rotate the soft palate about an axis), and/or decentering force (i.e., a force in essentially a medial or side-to-side direction that tends to offset the soft palate left or right), or a combination of two or more of these forces. The magnetic force F-mag maintains separation between the soft palate and the posterior pharyngeal wall, which is the desired therapeutic effect. The function desirably incorporates the premise that F-sep≦F-nat, such that F-nat can overcome F-sep to preserve normal airway function. The function also desirably incorporates the premise that F-mag≧F-sep, so that the desired separation between the soft palate and the posterior pharyngeal wall is maintained. The function resolves F-sep and F-nat to provide an optimal therapeutic force that, at night, resists collapse of the soft palate and uvula against the pharyngeal wall during sleep, yet does not affect speech, swallowing or drinking during normal activities awake or asleep. Since it is only used at night, CPAP can be removed, thus eliminating any effect on speech or swallowing during daytime hours or non-treatment. An implanted palate system is "turned on" all the time as the magnets cannot be easily removed and therefore must deal with the issue of preserving normal airway function while treating OSA or snoring.

The function also desirably includes a tolerance factor ΔTol, which takes into account that F-nat can increase with time after implantation, as an individual develops tolerance to F-mag. F-nat can thereby increase with time after implantation, as the individual trains his or herself to exert more force during swallowing or speech in the presence of F-mag to maintain normal airway function. The nature of the tolerance factor ΔTol can be ascertained by physical measurement of a given individual, or it can be selected empirically based upon general anatomic considerations for a population of individuals, or a combination of these and other considerations.

It is believed that F-mag for a magnetic force system that operates by magnetic force repulsion and/or torque and/or decentering acting on the palate should be no more than 200 g. More specifically, it is believed that a force F-mag of about 3 to about 80 g will provide therapeutic benefits without adversely affecting normal functioning of the airway.

VII. Conclusion

Although the disclosure hereof is detailed and exact to enable those skilled in the art to practice the invention, the physical embodiments herein disclosed merely exemplify the invention, which may be embodied in other specific structure. While the preferred embodiment has been described, the details may be changed without departing from the invention, which is defined by the claims.

The above-described embodiments of this invention are merely descriptive of its principles and are not to be limited. The scope of this invention instead shall be determined from the scope of the following claims, including their equivalents.

We claim:

1. An implant system comprising
   a first implant device comprising
      a carrier structure for placement in or on tissue in an airway, and
      at least a first and second source of magnetism carried by the carrier structure, each source generating a magnetic field having a direction, the direction of the magnetic field of the first source of magnetism being oriented at an angle from the direction of the magnetic field of the second source of magnetism, and
   a second implant device for implantation in or on a second tissue region in the airway,
   the second implant device including a third source of magnetism that interacts with at least one of the first and second sources of magnetism to develop a magnetic force between the first and second implant devices.

2. An implant system according to claim 1 wherein the carrier structure of the first implant device comprises a generally planar configuration prior to implantation.

3. An implant system according to claim 2 wherein the angle is formed by orienting a pole direction of one of the first and second sources to face a different direction than a pole direction of the other one of the first and second sources.

4. An implant system according to claim 1 wherein the carrier structure of the first implant device comprises a generally flexed configuration prior to implantation.

5. An implant system according to claim 4 wherein the angle is formed by flexure of the carrier structure.

6. An implant system according to claim 1 wherein the carrier structure of the first implant device flexes to conform to a curved tissue morphology after implantation.

7. An implant system according to claim 6 wherein the angle is formed by flexure of the carrier.

8. An implant system according to claim 1 wherein the angle is formed by a magnet having an angled field.

9. An implant system according to claim 1 wherein at least one of the first and second sources of magnetism comprises a permanent magnet.

10. An implant system according to claim 1 wherein at least one of the first and second sources of magnetism comprises a radial magnet.

11. An implant system according to claim 1 wherein the carrier structure of the first implant device includes an edge region, and
   wherein one of the first and second sources of magnetism is carried in the edge region.

12. An implant system comprising
   a first implant device comprising
      a carrier structure for placement in or on tissue in an airway, and at least a first and second source of magnetism carried by the carrier structure, each source generating a magnetic field having a direction, and means for orienting the direction of the magnetic field of the first source of magnetism at an angle from the direction of the magnetic field of the second source of magnetism, and a second implant device for implantation in or on a second tissue region in the airway, the second implant device including a third source of magnetism that interacts with at least one of the first and second sources of magnetism to develop a magnetic force between the first and second implant devices.

13. An implant system according to claim 1 or 12 wherein the angle is 90-degrees or less.

14. An implant system according to claim 1 wherein the magnetic force includes at least one of a repelling force, a torquing force, and a decentering force.

15. An implant system according to claim 1 wherein the angle for all sources of magnetism on the carrier structure is essentially equal.

16. An implant system according to claim 1 wherein the carrier structure is sized and configured for implantation in a tongue and/or a soft palate.

17. An implant system as defined in claim 1, further comprising instructions comprising (i) separately placing two or more of the implant devices in or on tissue in a first tissue region in association with a second magnetic structure, which is placed in or on a second tissue region different than the first tissue region, the magnetic filed orientation of the implant devices magnetically interacting with the second magnetic structure; (ii) assessing, as a function of the magnetic field orientation, a therapeutic effect that results from the interaction between each of the two or more implant devices and the second magnetic structure; and (iii) selecting as a desired magnetic field orientation, the magnetic field orientation that provides a desired therapeutic effect based, at least in part, upon the assessment of (ii).

18. A method comprising providing an implant device comprising a carrier structure for placement in or on tissue in an airway, and at least a first and second source of magnetism carried by the carrier structure, each source generating a magnetic field having a direction, the direction of the magnetic field of the first source of magnetism being oriented at an angle from the direction of the magnetic field of the second source of magnetism, implanting the implant device in or on a first tissue region in an airway, and implanting a second implant device in or on second tissue region in an airway, the second implant device including a third source of magnetism that interacts with at least one of the first and second sources of magnetism to develop a magnetic force between the first and second implant devices.

19. A method according to claim 18 wherein the first tissue region comprises one of a soft palate, a pharyngeal wall, and a tongue.

20. A method according to claim 18 wherein the magnetic force stabilizes a desired tissue orientation in an airway.

21. A method according to claim 18 wherein the magnetic force includes a repelling force.

22. A method according to claim 18 wherein the magnetic force includes at least one of a repelling force, a torquing force, and a decentering force.

23. A method according to claim 18 further comprising placing, as the second source of magnetism, an implant device having a desired magnetic field orientation by (i) providing a family of candidate implant devices, each comprising a source of magnetism having a magnetic field orientation, the magnetic field orientations of the candidate implant devices differing within the family; (iii) separately placing two or more of the candidate implant devices in or on tissue in a soft palate in interaction with the first source of magnetism; (iv) assessing, as a function of the magnetic field orientation, a therapeutic effect of the interaction between each of the two or more candidate implant device and the first source of magnetism; and (v) selecting as the desired magnetic field orientation, the magnetic field orientation that provides a desired therapeutic effect based, at least in part, upon the assessment of (iv); and (v) providing an implant device having the desired magnetic field orientation.

24. An implant system according to claim 1 or 12 wherein the angle is at least 10-degrees.

25. An implant system according to claim 12 wherein the magnetic force includes at least one of a repelling force, a torquing force, and a decentering force.

26. A method comprising providing an implant device comprising a carrier structure for placement in or on tissue in an airway, and at least a first and second source of magnetism carried by the carrier structure, each source generating a magnetic field having a direction, and means for orienting the direction of the magnetic field of the first source of magnetism at an angle from the direction of the magnetic field of the second source of magnetism, implanting the implant device in or on a first tissue region in an airway, and implanting a second implant device in or on second tissue region in an airway, the second implant device including a third source of magnetism that interacts with at least one of the first and second sources of magnetism to develop a magnetic force between the first and second implant devices.

27. A method according to claim 26 wherein the magnetic force stabilizes a desired tissue orientation in an airway.

28. A method according to claim 26 wherein the magnetic force includes a repelling force.

29. A method according to claim 26 wherein the magnetic force includes at least one of a repelling force, a torquing force, and a decentering force.

\* \* \* \* \*